US011085928B2

(12) United States Patent
Tamura et al.

(10) Patent No.: US 11,085,928 B2
(45) Date of Patent: Aug. 10, 2021

(54) MICROORGANISM IDENTIFICATION METHOD

(71) Applicants: SHIMADZU CORPORATION, Kyoto (JP); MEIJO UNIVERSITY, Nagoya (JP)

(72) Inventors: Hiroto Tamura, Kani (JP); Naomi Yamamoto, Nagoya (JP); Teruyo Kato, Aisai (JP); Keisuke Shima, Kyoto (JP); Shinji Funatsu, Kyoto (JP)

(73) Assignees: SHIMADZU CORPORATION, Kyoto (JP); MEIJO UNIVERSITY, Nagoya (JP)

( * ) Notice: Subject to any disclaimer, the term of this patent is extended or adjusted under 35 U.S.C. 154(b) by 197 days.

(21) Appl. No.: 16/089,858

(22) PCT Filed: Mar. 31, 2016

(86) PCT No.: PCT/JP2016/060866
§ 371 (c)(1),
(2) Date: Sep. 28, 2018

(87) PCT Pub. No.: WO2017/168741
PCT Pub. Date: Oct. 5, 2017

(65) Prior Publication Data
US 2019/0120851 A1 Apr. 25, 2019

(51) Int. Cl.
G01N 27/62 (2021.01)
G01N 33/68 (2006.01)
C12Q 1/04 (2006.01)
G01N 33/569 (2006.01)

(52) U.S. Cl.
CPC .......... *G01N 33/6851* (2013.01); *C12Q 1/04* (2013.01); *G01N 27/62* (2013.01); *G01N 33/56922* (2013.01); *G01N 33/6848* (2013.01); *G01N 2333/205* (2013.01); *G01N 2560/00* (2013.01); *Y02A 50/30* (2018.01)

(58) Field of Classification Search
CPC combination set(s) only.
See application file for complete search history.

(56) References Cited

U.S. PATENT DOCUMENTS

2014/0288852 A1 9/2014 Ojima et al.

FOREIGN PATENT DOCUMENTS

| JP | 2006-191922 A | 7/2006 |
| JP | 2013-085517 A | 5/2013 |
| JP | 2015-184020 A | 10/2015 |
| WO | 2010022400 A2 | 2/2010 |

OTHER PUBLICATIONS

Mandrell, R. et al Appl. Environ. Microbiol. 2005 vol. 71, pp. 6292-6307.*
Mandrell, R.E. et al., Appl. Environ. Microbiol. 2005 vol. 71, pp. 6292-6307.*
Communication issued Nov. 25, 2019 by the European Patent Office in application No. 16896958.2.
Fagerquist, "Amino Acid Sequence Determination of Protein Biomarkers of Campylobacter upsaliensis and C. helveticus by "Composite" Sequence Proteomic Analysis", Journal of research articles proteome research, 2007, vol. 6, No. 7, pp. 2539-2549 with Supplementary information, (75 pages total).
List of prokaryotic names with standing in nomenclature, (Internet search on Mar. 25, 2016; URL:http://www.bacterio.net/), 16 pages total.
Rosenquist et al., "Quantitative risk assessment of human campylobacteriosis associated with thermophilic *Campylobacter* species in chickens", International Journal of Food Microbiology 83 (2003), pp. 87-103 (17 pages total).
Corry et al., "Poultry as a source of *Campylobacter* and related organisms", Journal of Applied Microbiology 2001, vol. 90, pp. 96S-114S (19 pages total).
Hald et al., "*Campylobacter jejuni* and *Campylobacter coli* in wild birds on Danish livestock farms", Acta Vet Scand (2016), vol. 58, No. 11, pp. 1-10 (10 pages total).
Newell et al., "Poultry Infections and Their Control at the Farm Level", ASM press, 2000, pp. 497-509 (7 pages total).
Penner et al., "Passive Hemagglutination Technique for Serotyping *Campylobacter fetus* subsp. *jejuni* on the Basis of Soluble Heat-Stable Antigens", Journal of Clinical Microbiology, Dec. 1980, vol. 12, No. 6, pp. 732-737 (6 pages total).
Lior et al., "Serotyping of *Campylobacter jejuni* by Slide Agglutination Based on Heat-Labile Antigenic Factors", Journal of Clinical Microbiology, May 1982, vol. 15, No. 5, pp. 761-768 (8 pages total).

(Continued)

Primary Examiner — Heidi Reese
(74) Attorney, Agent, or Firm — Sughrue Mion, PLLC

(57) ABSTRACT

A microorganism identification method includes steps of: obtaining a mass spectrum through mass spectrometry of a sample including microorganisms; reading, from the mass spectrum, a mass-to-charge ratio m/z of a peak associated with a marker protein; and identifying which bacterial species of the genus *Campylobacter* are included in the microorganisms in the sample based on the mass-to-charge ratio m/z. The microorganism identification method is further characterized in that at least one of the following 18 marker proteins is used as the marker protein, S10, L23, S19, L22, L16, L29, S17, L14, L24, S14, L18, L15, L36, S13, S11 (Me), L32, and L7/L12.

18 Claims, 13 Drawing Sheets
Specification includes a Sequence Listing.

(56) References Cited

OTHER PUBLICATIONS

Samosornsuk et al., "Evaluation of a Cytolethal Distending Toxin (cdt) Gene-Based Species-Specific Multiplex PCR Assay for the Identification of *Campylobacter* Strains Isolated from Poultry in Thailand", Microbiol. Immunol., 2007, vol. 51, No. 9, pp. 909-917 (9 pages total).
Asakura et al., "Comparative analysis of cytolethal distending toxin (cdt) genes among *Campylobacter jejuni*, *C. coli* and *C. fetus* strains", Microbial Pathogenesis 42 (2007), pp. 174-183 (10 pages total).
Gibson et al., "Inhibition of DNAse activity in PFGE analysis of DNA from *Campylobacter jejuni*", Letters in Applied Microbiology, 1994, vol. 19, pp. 357-358 (2 pages total).
Behringer et al., "Typing of *Campylobacter jejuni* and *Campylobacter coli* isolated from live broilers and retail broiler meat by flaA-RFLP, MLST, PFGE and REP-PCR", Journal of Microbiological Methods 84 (2011), pp. 194-201 (8 pages total).
Zautner et al., "Epidemiological Association of Different *Campylobacter jejuni* Groups with Metabolism-Associated Genetic Markers", Applied and Environmental Microbiology, Apr. 2011, vol. 77, No. 7, pp. 2359-2365 (7 pages total).
Mandrell et al., "Speciation of *Campylobacter coli, C. jejuni, C. helveticus, C. lari, C. sputorum*, and *C. upsaliensis* by Matrix-Assisted Laser Desorption Ionization-Time of Flight Mass Spectrometry", Applied and Environmental Microbiology, Oct. 2005, vol. 71, No. 10, pp. 6292-6307 (16 pages total).
Fagerquist et al., "Genomic and Proteomic Identification of a DNA-Binding Protein Used in the "Fingerprinting" of *Campylobacter* Species and Strains by MALDI-TOF-MS Protein Biomarker Analysis", Anal. Chem., Aug. 1, 2005, vol. 77, No. 15, pp. 4897-4907 (11 pages total).
Alispahic et al., "Species-specific identification and differentiation of *Arcobacter, Helicobacter* and *Campylobacter* by full-spectral matrix-associated laser desorption/ionization time of flight mass spectrometry analysis", Journal of Microbiology (2010), vol. 59, pp. 295-301 (7 pages total).
Bessede et al., "Identification of *Campylobacter* species and related organisms by matrix assisted laser desorption ionization-time of flight (MALDI-TOF) mass spectrometry", Clinical Microbiology and Infection, Nov. 2011, vol. 17, No. 11, pp. 1735-1739 (5 pages total).
Zautner et al., "Discrimination of multilocus sequence typing-based *Campylobacter jejuni* subgroups by MALDI-TOF mass spectrometry", BMC Microbiology 2013, vol. 13:247, 1-8 pages.
Fagerquist et al., "Composite sequence proteomic analysis of protein biomarkers of *Campylobacter coli, C. lari* and *C. concisus* for bacterial identification", The Royal Society of Chemistry, Analyst., 2007, vol. 132, No. 10, pp. 1010-1023 (15 pages total).
Fagerquist et al., "Sub-Speciating *Campylobacter jejuni* by Proteomic Analysis of its Protein Biomarkers and Their Post-Translational Modifications", Journal of research articles proteome research, 2006, vol. 5, No. 10, pp. 2527-2538 (12 pages total).
Fagerquist, "Amino Acid Sequence Determination of Protein Biomarkers of *Campylobacter upsaliensis* and *C. helveticus* by "Composite" Sequence Proteomic Analysis", Journal of research articles proteome research, 2007, vol. 6, No. 7, pp. 2539-2549 (11 pages total).
Tamura et al., "Rapid Bacterial Discrimination by MALDI-TOF MS Based on Ribosomal Proteins as Biomarkers: Rapid Bacterial Discrimination by S10-GERMS Method", Shimadzu Review, 2013, vol. 70, Nos. 3-4, pp. 157-170 (16 pages total), ISSN: 0371-005X.
Ojima-Kato et al., "Discrimination of *Escherichia coli* 0157, 026 and 0111 from Other Serovars by MALDI-TOF MS Based on the S10-GERMS Method", Plos One, Nov. 2014, vol. 9, Issue 11, e113458, pp. 1-11.
Ojima-Kato et al., "Assessing the performance of novel software Strain Solution on automated discrimination of *Escherichia coli* serotypes and their mixtures using matrix-assisted laser desorption ionization-time of flight mass spectrometry", Journal of Microbiological Methods 119 (2015), pp. 233-238 (6 pages total).
Tamura et al., "Novel Accurate Bacterial Discrimination by MADI-Time-of-Flight MS Based on Ribosomal Proteins Coding in S10-spc-alpha Operon at Strain Level S10-GERMS", J. Am. Soc. Mass Spectrom. (2013), vol. 24, pp. 1185-1193 (9 pages total).
Newell, "The ecology of *Campylobacter jejuni* in avian and human hosts and in the environment", Int. J. Infect. Dis., 2002, vol. 6, pp. 3S13-3S21 (6 pages total).
Penner et al., "The Serotype and Biotype Distribution of Clinical Isolates of *Campylobacter jejuni* and *Campylobacter coli* over a Three-Year Period", The Journal of Infectious Diseases, Feb. 1983, vol. 147, No. 2, pp. 243-246 (4 pages total).
International Search Report dated Jun. 28, 2016, issued by the International Searching Authority in application No. PCT/JP2016/060866.
International Preliminary Report on Patentability with translation of the Written Opinion dated Oct. 2, 2018, issued by the International Bureau in application No. PCT/JP2016/060866.
Written Opinion dated Jun. 28, 2016, issued by the International Searching Authority in application No. PCT/JP2016/060866.
Communication dated Jun. 9, 2021 by the Chinese Patent Office in Application No. 201680084073.0.

\* cited by examiner

Fig. 3

| No. | Genus | Species | Subspecies | Strain | serovar(Penner) | Obtained from |
|---|---|---|---|---|---|---|
| 2 | Campylobacter | jejuni | doylei | ATCC 49349 | D | ATCC |
| 3 | Campylobacter | jejuni | doylei | ATCC 49350 | D,F complex | ATCC |
| 4 | Campylobacter | jejuni | jejuni | ATCC 29428 | A | ATCC |
| 5 | Campylobacter | jejuni | jejuni | ATCC 33291 | U | ATCC |
| 15 | Campylobacter | jejuni | jejuni | ATCC 33560 | R | ATCC |
| 16 | Campylobacter | jejuni | jejuni | ATCC 700819 | B | ATCC |
| 7 | Campylobacter | fetus | fetus | JCM 2527 | | JCM |
| 8 | Campylobacter | fetus | venerealis | JCM 2528 | | JCM |
| 10 | Campylobacter | lari | lari | JCM 14870 | | JCM |
| 14 | Campylobacter | coli | | JCM 2529 | | JCM |

* Weak antigen agglutination exhibited in agglutination test
ATCC: American Type Culture Collection
JCM: RIKEN, Japan, Bioresource Center, Microbe Division

Fig. 4

| Name | Sequencing (5'-3') | Used for |
|---|---|---|
| Cam-S10-F | GGAAAGAATYAGGCTTAAGCTAAAAGCTTA | Sequencing for and amplification of S10 region |
| Cam-S10-R | TCCGGTGCWAGWGAWACRATYTTCATA | Sequencing for and amplification of S10 region |
| Cam-S10-1 | GGAATAYATYGTAGAAAAAATHGGHATGAG | Sequencing for S10 region |
| Cam-S10-2r | TACCTGGYTGAACRCGACCTG | Sequencing for S10 region |
| Cam-S10-3 | GTGGTGGTAAAAARCCWGGAGACAA | Sequencing for S10 region |
| Cam-S10-4 | GGACCAAADGCWACHGCRCC | Sequencing for S10 region |
| Cam-S10-5 | ATATACTCCAAGYAGAAGATWTATBACAGG | Sequencing for S10 region |
| Cam-S10-6 | CCVGTTTATRTHACWGAAAATCAYATMGG | Sequencing for S10 region |
| Cam-S10-7r | TCTWGCYTTWGTTGGAGATARTCTTATGAA | Sequencing for S10 region |
| Cam-S10-8 | ATAGAAAYTGGGARTCWAGATGGTTTCC | Sequencing for S10 region |
| Cam-S10-9 | CTTATGGHAAYATAGGDRTWAAAGTDTGGAT | Sequencing for S11 region |
| Cam-S10-10 | AAAAGCTAAAAACWATGCARCTWACTAAYCC | Sequencing for S12 region |
| Cam-spc-F | ATGTGTATYAARGTTTTAGGBGGTAGYAAA | Sequencing for and amplification of spc region |
| Cam-spc-R | AATTTGAGCYTCDATYTTTCTCATYGTRTC | Sequencing for and amplification of spc region |
| Cam-spc-1 | GARTTTGATATHAAAAAYCCTATGCTTATMCC | Sequencing for spc region |
| Cam-spc-2 | CAATGATWGCAAAAGCDGCMCGCAA | Sequencing for spc region |
| Cam-spc-3 | GGWTATTGGGGAACTTAYAGAGCTTTA | Sequencing for spc region |
| Cam-spc-4r | TTAGATGTYTTRCCRGCTTTGCGKAT | Sequencing for spc region |
| Cam-spc-5 | AATTTGAAGAAGTAATCGTCGAYATCGG | Sequencing for spc region |
| Cam-spc-6r | ATTRACSCCMGGWACTGGMACATAA | Sequencing for spc region |
| Cam-alpha-F | AAAGTHGAACTHACRCCHTATAGYCTTGA | Sequencing for and amplification of alpha region |
| Cam-alpha-R | AGCCRCCCATRCTATCRAATTCATG | Sequencing for and amplification of alpha region |
| Cam-alpha-1 | TAAGYGAAGATGARGCHGCDGCTAT | Sequencing for alpha region |
| Camp-alpha-2r | CCTTTTCTRTGTCTTAAGCCTCTAWAGC | Sequencing for alpha region |
| Camp-alpha-3 | GAGGACGAGTWGARAAATTAGAAAGACG | Sequencing for alpha region |

Fig. 5

| Amino acid | Mass |
|---|---|
| A | 71.079 |
| R | 156.188 |
| N | 114.103 |
| D | 115.088 |
| C | 103.145 |
| Q | 128.13 |
| E | 129.114 |
| G | 57.052 |
| H | 137.141 |
| I | 113.159 |
| L | 113.159 |
| K | 128.174 |
| M | 131.198 |
| F | 147.176 |
| P | 97.116 |
| S | 87.078 |
| T | 101.104 |
| W | 186.213 |
| Y | 163.175 |
| V | 99.132 |

Fig. 6

Fig. 11A
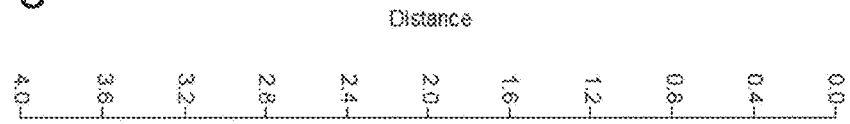
Fig. 11B
| | L32 | L7/L12 | L23 | L24 | S14 | L36 |
|---|---|---|---|---|---|---|
| 1 | 5483.43 | 12886.7 | 10424.1 | 8152.7 | 6826.3 | 4365.4 |
| 2 | 5497.46 | 12900.7 | 10437.1 | 8179.7 | 6812.2 | 4332.3 |
| 3 | 5513.5 | 12869.7 | 10394.0 | 8042.6 | 6785.2 | |
| 4 | 5510.46 | 12894.7 | 10466.2 | 8027.3 | 6729. | |
| 5 | 5537.57 | 12942.8 | 10375.0 | | | |
| 6 | | 12966.8 | 10480.1 | | | |
Fig. 11C
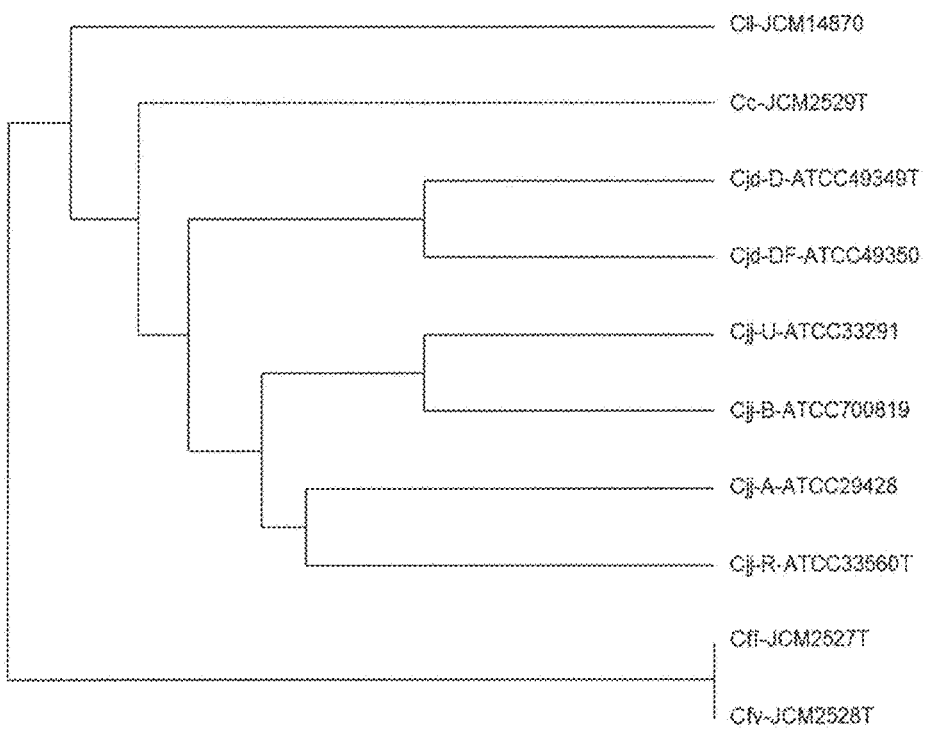

| Species | Subspecies | Serotype | Strain No. | L32 | L7/L12 | L23 | S11 |
|---|---|---|---|---|---|---|---|
| C. jejuni | jejuni | R | ATCC 33560T | 1 | 1 | 1 | 1 |
| C. jejuni | jejuni | A | ATCC 29428 | 2 | 1 | 4 | 1 |
| C. jejuni | jejuni | U | ATCC 33291 | 2 | 2 | 2 | 1 |
| C. jejuni | jejuni | B | ATCC 700819 | 2 | 5 | 2 | 6 |
| C. jejuni | doylei | D | ATCC 49349T | 1 | 1 | 3 | 3 |
| C. jejuni | doylei | D,F complex | ATCC 49350 | 4 | 1 | 3 | 3 |
| C. coli | | | JCM 2529 | 3 | 4 | 3 | 1 |
| C. fetus | fetus | | JCM 2527 | 5 | 3 | 5 | 4 |
| C. fetus | venerealis | | JCM 2528 | 5 | 3 | 5 | 5 |
| C. lari | lari | | JCM 14870 | 6 | 6 | 6 | 2 |

| | L32 | L7/L12 | L23 | S11 |
|---|---|---|---|---|
| 1 | 5483.43 | 12886.70 | 10424.11 | 13777.11 |
| 2 | 5497.46 | 12900.73 | 10437.15 | 13763.11 |
| 3 | 5510.46 | 12869.70 | 10394.08 | 13807.14 |
| 4 | 5513.50 | 12865.70 | 10465.20 | 13819.16 |
| 5 | 5531.48 | 12942.80 | 10375.08 | 13833.16 |
| 6 | 5537.57 | 12968.80 | 10480.13 | |

| Species | Subspecies | Serotype | Strain No. | L32 | L7/L12 | L24 | S11 |
|---|---|---|---|---|---|---|---|
| C. jejuni | jejuni | R | ATCC 33560T | 1 | 1 | 1 | 1 |
| C. jejuni | jejuni | A | ATCC 29428 | 2 | 1 | 1 | 1 |
| C. jejuni | jejuni | U | ATCC 33291 | 2 | 2 | 1 | 1 |
| C. jejuni | jejuni | B | ATCC 700819 | 2 | 5 | 1 | 3 |
| C. jejuni | doylei | D | ATCC 49349T | 1 | 1 | 2 | 3 |
| C. jejuni | doylei | D.Fcomplex | ATCC 49350 | 4 | 1 | 2 | 3 |
| C. coli | | | JCM 2529 | 3 | 4 | 1 | 1 |
| C. fetus | fetus | | JCM 2527 | 5 | 3 | 4 | 4 |
| C. fetus | venerealis | | JCM 2528 | 5 | 3 | 4 | 5 |
| C. lari | lari | | JCM 14870 | 6 | 6 | 3 | 2 |

| | L32 | L7/L12 | L24 | S11 |
|---|---|---|---|---|
| 1 | 5483.43 | 12886.70 | 8152.70 | 13777.11 |
| 2 | 5497.46 | 12900.73 | 8179.70 | 13763.11 |
| 3 | 5510.46 | 12869.70 | 8042.60 | 13807.14 |
| 4 | 5513.60 | 12864.70 | 8027.60 | 13819.16 |
| 5 | 5531.48 | 12942.80 | | 13833.18 |
| 6 | 5537.57 | 12969.80 | | |

| Species | Subspecies | Serotype | Strain No. | L24 | S14 | S11 |
|---|---|---|---|---|---|---|
| C. jejuni | jejuni | R | ATCC 33560T | 1 | 1 | 1 |
| C. jejuni | jejuni | A | ATCC 29428 | 1 | 1 | 1 |
| C. jejuni | jejuni | U | ATCC 33291 | 1 | 1 | 1 |
| C. jejuni | jejuni | B | ATCC 700819 | 1 | 1 | |
| C. jejuni | doylei | D | ATCC 49349T | 2 | 1 | 3 |
| C. jejuni | doylei | D.Fcomplex | ATCC 49350 | 2 | 1 | 3 |
| C. coli | | | JCM 2529 | 1 | 2 | 1 |
| C. fetus | fetus | | JCM 2527 | 4 | 4 | 4 |
| C. fetus | venerealis | | JCM 2528 | 4 | 4 | 5 |
| C. lari | lari | | JCM 14870 | 3 | 3 | 2 |

| | L24 | S14 | S11 |
|---|---|---|---|
| 1 | 8152.70 | 6826.31 | 13777.11 |
| 2 | 8179.70 | 6812.28 | 13763.11 |
| 3 | 8042.60 | 6785.22 | 13807.14 |
| 4 | 8027.50 | 6729.15 | 13819.18 |
| 5 | | | 13833.18 |
| 6 | | | |

Fig. 15A
| Species/Subspecies | Strain No. | L24 | S14 | L36 |
|---|---|---|---|---|
| C.jejuni.sp.jejuni | ATCC 33560T | 1 | 1 | 1 |
| C.jejuni.sp.jejuni | ATCC 29428 | 1 | 1 | 1 |
| C.jejuni.sp.jejuni | ATCC 33291 | 1 | 1 | 1 |
| C.jejuni.sp.jejuni | ATCC 700819 | 1 | 1 | 1 |
| C.jejuni.sp.doylei | ATCC 49349T | 2 | 1 | 1 |
| C.jejuni.sp.doylei | ATCC 49350 | 2 | 1 | 1 |
| C.coli | JCM 2529 | 1 | 2 | 1 |
| C.fetus.sp.fetus | JCM 2527 | 4 | 4 | 2 |
| C.fetus.sp.venerealis | JCM 2528 | 4 | 4 | 2 |
| C.lari.sp.lari | JCM 14870 | 3 | 3 | 1 |
Fig. 15B
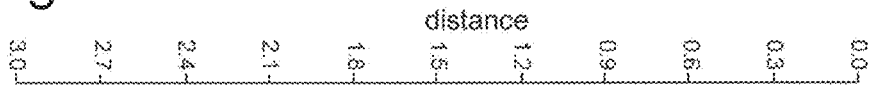
|   | L24 | S14 | L36 |
|---|---|---|---|
| 1 | 8152.7 | 6826.3 | 4365.4 |
| 2 | 8179.7 | 6812.2 | 4332.3 |
| 3 | 8042.6 | 6785.2 |   |
| 4 | 8021.6 | 6726.1 |   |
| 5 | 7923.6 |   |   |
| 6 |   |   |   |
| 7 |   |   |   |
Fig. 15C
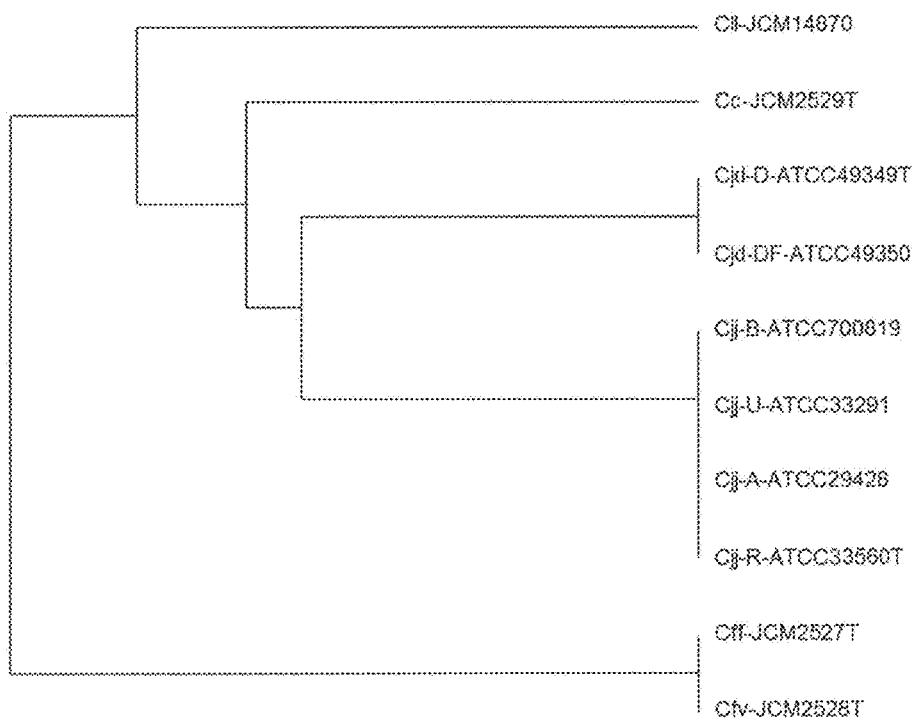

MICROORGANISM IDENTIFICATION METHOD

CROSS REFERENCE TO RELATED APPLICATIONS

This application is a National Stage of International Application No. PCT/JP2016/060866 filed on Mar. 31, 2016.

TECHNICAL FIELD

The present invention relates to a microorganism identification method that utilizes mass spectrometry.

BACKGROUND ART

Bacteria of the genus *Campylobacter* are asporogenous, microaerophilic, gram-negative helical bacteria, among which 33 bacterial species have so far been identified and reported (Non Patent literature 1). Of the bacterial species of this genus. *Campylobacter fetus* has been known for about 100 years to cause miscarriage in livestock. Today, *Campylobacter jejuni* and *Campylobacter coli* are drawing attention as pathogens for *Campylobacter* infections in humans. *Campylobacter* infections are currently on the increase in a number of advanced countries (Non Patent literature 2) and are often fraught with complications which are peripheral nerve disorders including Guillain-Barré syndrome and Fisher syndrome.

The growth of *Campylobacter* bacteria is slow, taking time approximately twice as long as typical bacteria. Bacteria of this genus grow in 40 to 50 minutes at 37° C. and at pH 5.5 to 8.0, and perish in two to three days at room temperature under aerobic conditions. These bacteria, however, may survive over an appreciable length of time at 10° C. or below under aerobic conditions, and may survive for more than a month in raw meat frozen at minus 20° C. or below and in raw meat packed by vacuum packaging or gas replacement packaging. While the optimum temperature for growth may be 30° C. to 37° C. in many of the *Campylobacter* bacteria, some species may grow at 25° C. or 42° C. Bacterial species of this genus that grow at 42° C. are called "thermophilic *Campylobacter*", which include species associated with food poisoning.

*Campylobacter* bacteria are often widely distributed in the intestinal canal of livestock, poultry, pets, and wild animals, and bacteria of this genus deemed to derive from these animals were isolated from river water, lake water, and sewage water (Non Patent Literature 3). The source of infection of the gravest concern in the advanced countries is fowl, and meat of fowl was found to be more contaminated with these bacteria than meat of any other domestic animals (Non Patent Literature 5). According to the reports of past researches in Japan and other countries, the infection fowl is not vertical but is horizontal, which spreads in short time. Transmission of these bacteria from migratory birds to poultry was also reported (Non Patent Literatures 4 and 5).

While two serotyping methods (Penner method, Lior method) are typically used in the epidemiological surveys on *Campylobacter jejuni* and *Campylobacter coli* (Non Patent Literatures 6 and 7), only a limited number of institutions are equipped with diagnostic serums for the Penner serotyping method, while the Lior serotyping method is a time-consuming diagnostic approach.

Under the circumstances. *Campylobacter jejuni* and *Campylobacter coli* have to be monitored and controlled in the food and medical industries as food-poisoning bacteria, and identification of these bacteria.

The methods so far proposed and reported are, for example, m-PCR (Non Patent Literatures 8 and 9), Pulsed-field gel electrophoresis (Non Patent Literature 10), and Multilocus sequence typing (Non Patent Literatures 11 and 12). These methods, however, require complicated handling and investment of time.

In the meantime, the microorganism identification method using Matrix Assisted Laser Desorption-ionization/time-of-flight Mass Spectrometry (MALDI-TOF MS) has been introduced and is rapidly spreading in the clinical field and in the food industry. This microorganism identification method identifies microorganisms based on mass spectral patterns obtained with trace amounts of microbial samples. According to this method, an analysis result can be obtained in short time, and multiple samples can be continuously analyzed. This method is, therefore, expected to facilitate and accelerate identification of microorganisms.

Some study groups have attempted to identify bacteria of the genus *Campylobacter* using the MALDI-TOF MS (Non Patent Literatures, 13, 14, 15, 16, and 17). According to Non Patent Literature 13, six bacterial species of the genus *Campylobacter* are identified by different proteins, as follows. *Campylobacter coli* (hereinafter, "*Campylobacter*" may be abbreviated to "C.") is identified by ribosomal protein L7/L12 and the DNA binding protein HU, *C. jejuni* is identified by ribosomal protein S13 and the DNA binding protein HU, *C. lali* is identified by ribosomal protein L7/L12, chaperonin GroES, and unknown protein of 9651 Da, *C. spectorum* is identified by unknown proteins of 12786 Da and 9796 Da, *C. helveticus* is identified by unknown protein of 9404 Da and the DNA binding protein HU, and *C. upsaliensi* is identified by the DNA binding protein HU. This report, however, is not supported by any genetic evidences.

It is described in Non Patent Literature 13 that the DNA binding protein HU is used to identify, based on genetic evidences, six bacterial species of the genus *Campylobacter* (*C. coli, C. jejuni, C. lali, C. spectorum, C. helveticus*, and *C. upsaliensi*). In our reproducibility test, however, steady detection of the DNA binding protein HU was not possible with the MALDI-TOF MS.

According to Non Patent Literature 17, groups of *C. jejuni* according to the multilocus sequence typing were identified by the MALDI-TOF MS. This paper, however, failed to articulate the origins of biomarker peaks.

CITATION LIST

Patent Literature

Patent Literature 1: JP 2006-191922 A
Patent Literature 1: JP 2013-085517 A

Non Patent Literature

Non Patent Literature 1: List of prokaryotic names with standing in nomenclature, (Internet search on Mar. 25, 2016; URL:http://www.bacterio.net/)
Non Patent Literature 2: Rosenquist, H. et. al., int. J. Food Microbiol., 2003, 83(1), 87-103
Non Patent Literature 3: Corr J. et. al., Appl. Microbiol. 2011, 96S-114S
Non Patent Literature 4: Hald, B. et. al., Acta. Vet Scand, 2016, 58 (1), 1

Non Patent Literature 5: Newell G. et. al., ASM press, 2000, 497-509

Non Patent Literature 6: Penner, J. et. al., J. Clin. Microbiol. 1980, 12: 732-737

Non Patent Literature 7: Lior, H. et al. J. Clin. Microbiol. 1980, 15: 761-768

Non Patent Literature 8: Samosomsuk, W. et al. Microbiol. Immunol., 2007, 51 (9), 909-917

Non Patent Literature 9: Asakura, M., et al., Microb. Pathog., 2007, 42, 174-183

Non Patent Literature 10: Gibson, J. et al., Letters in Applied Microbiology, 1994, 19(5), 357-358

Non Patent Literature 11: Behringer, M., et al., Journal of Microbiological Methods, 2011, 84 (2), 194-201

Non Patent Literature 12: Zautner, A. E., et al., Applied and environmental microbiology, 2011, 77 (7), 2359-2365

Non Patent Literature 13: Mandrell, R. E., Harden, L. A., Bates, A., Miller, W. G, Haddon, W. F., & Fagerquist, C. K., Applied and environmental microbiology, 2005, 71 (10), 6292-6307

Non Patent Literature 14: Fagerquist, C. K., Miller, W. G., Harden, L. A., Bates, A. H., Vensel, W. H., Wang, G., & Mandrel, R. E., Analytical chemistry, 2005, 77 (15), 4897-4907

Non Patent Literature 15: Alispahic, M., et. al., Journal of medical microbiology, 2010, 59 (3), 295-301

Non Patent Literature 16: Bessede, E., et. al., 2011, Clinical Microbiology and Infection. 17 (11), 1735-1739

Non Patent Literature 17: Zautner, A. E., et al., BMC microbiology, 2013, 13:247

SUMMARY OF INVENTION

Technical Problem

While these different literatures have so far reported on identification and classification of the bacterial species of the genus *Campylobacter* using the MALDI-TOF MS, none of them refers to how to identify bacterial subspecies and/or strains of this genus, and few of them successfully determined Which ones of the proteins are the origins of biomarker peaks and peaks that appear on the obtained mass spectrum. Thus, most of the study results reported in these papers are unreproducible, which means that marker proteins showing high reliability and suitable for identification of bacterial subspecies and strains of the genus *Campylobacter* still remain unascertained today.

Patent Literature 1 describes an effective method which, based on the fact that about a half of peaks obtained through mass spectrometry of microbial bacteria is associated with ribosomal proteins, determines types of proteins which may be the origins of peaks obtained through mass spectrometry by associating mass-to-charge ratios of the peaks with calculated masses deduced from amino acid sequences translated from information on the base sequences of ribosomal protein genes (S10-GERMS). This method, by thus using the mass spectrometry and dedicated software, may enable very reliable identification of microorganisms supported by theoretical evidences (Patent Literature 2).

The present invention is directed to providing a genetic information-based biomarker that excels in reliability in order to identify bacterial subspecies of the genus *Campylobacter* and *C. jejuni* strains.

Solution to Problem

To this end, the inventors of the present invention were committed to various studies, experiments, and discussions, and were led to the following findings: the following 18 ribosomal proteins, S10, L23, S19, L22, L16, L29, S17, L14, L24, S14, L18, L15, L36, S13, S11 (Me), L32, and L7/L12 may be useful marker proteins for identifying, through mass spectrometry, which bacterial species of the genus *Campylobacter* are included in a sample and also identifying bacterial subspecies and strains (serotype) of this genus; bacterial species, subspecies and strains (serotype) of the genus *Campylobacter* may be identifiable by using at least one selected from the before-mentioned ribosomal proteins; and bacterial species, subspecies and strains (serotype) of the genus *Campylobacter* may be reproducibly and expeditiously identifiable by, among the before-mentioned ribosomal proteins, at least one of the following seven proteins, L23, L24, S14, L36, L32, L7/L12, and S11. Then, the inventors finally accomplished the present invention.

A microorganism identification method according to the present invention was made to address the issues of the known art. The microorganism identification method includes steps of:

a) obtaining a mass spectrum through mass spectrometry of a sample including microorganisms;

b) reading, from the mass spectrum, a mass-to-charge ratio m/z of a peak associated with a marker protein; and c) identifying which bacterial species of the genus *Campylobacter* are included in the microorganisms in the sample based on the mass-to-charge ratio m/z.

In this microorganism identification method, the marker protein is at least one of 18 ribosomal proteins, S10, L23, S19, L22, L16, L29, S17, L14, L24, S14, L18, L15, L36, S13, S11 (Me), L32, and L7/L12.

In this microorganism identification method, the marker protein is preferably at least one of seven marker proteins L23, L24, S14, L36, L32, L7/L12, and S11.

The microorganism identification method is suitably used to identify whether the bacterial species of the genus *Campylobacter* is any one of five species, *Campylobacter jejuni* subsp. *jejuni*, *Campylobacter jejuni* subsp. *doylei*, *Campylobacter coli*, *Campylobacter fetus*, and *Campylobacter lari*.

When the bacterial species of the genus *Campylobacter* is *Campylobacter jejuni* subsp. *jejuni*, the marker protein preferably includes at least L24, any one of L32, L23, S14, and L7/L12, and L23.

When the bacterial species of the genus *Campylobacter* is *Campylobacter jejuni* subsp. *doylei*, the marker protein preferably includes at least L24.

When the bacterial species of the genus *Campylobacter* is *Campylobacter coli*, the marker protein preferably includes at least any one selected from L32, S14, and a group consisting of L23 and L24.

When the bacterial species of the genus *Campylobacter* is *Campylobacter fetus*, the marker protein is at least one of L23, L24, S14, L36, L32, L7/L12, and S11.

When the bacterial species of the genus *Campylobacter* *Campylobacter lari*, the marker protein includes at least one of L23, L24, S14, L32, and L7/L12.

When the bacterial species of the genus *Campylobacter* is *Campylobacter jejuni*, the serotype of this species may be used in the microorganism identification method disclosed herein. Specifically, when the bacterial species of the genus *Campylobacter* is *Campylobacter jejuni* and is identified as having serotype R, the marker protein preferably includes at least L23.

When the bacterial species of the genus *Campylobacter* is *Campylobacter jejuni* and is identified as having serotype A, the marker protein preferably includes at least L23 or L32 and L7/L12.

When the bacterial species of the genus *Campylobacter* is *Campylobacter jejuni* and is identified as having serotype B, the marker protein preferably includes at least L7/L12.

When the bacterial species of the genus *Campylobacter* is *Campylobacter jejuni* and is identified as having serotype U, the marker protein preferably includes at least 1-7/L12.

When the bacterial species of the genus *Campylobacter* is *Campylobacter jejuni* and is identified as having serotype D, the marker protein preferably includes at least L32 and L23 or L32 and L24.

When the bacterial species of the genus *Campylobacter* is *Campylobacter jejuni* and is identified as having serotypes DF complex, the marker protein preferably includes at least L32.

In the microorganism identification method, cluster analysis using, as indicator, at least mass-to-charge ratios m/z associated with L24, S14, and S11 may be employed to accurately determine which bacterial species of the genus *Campylobacter* are included in the microorganisms in the sample.

In the cluster analysis, the indicator may further include at least mass-to-charge ratios m/z associated with L24, S14, and L36.

In this instance, the microorganism identification method may further include a step of generating a dendrogram that shows an identification result obtained by the cluster analysis.

In the microorganism identification method disclosed herein, the serotype when the bacterial species of the genus *Campylobacter* is *Campylobacter jejuni* may be determined by employing cluster analysis using, as indicator, at least mass-to-charge ratios m/z associated with L32, L7/L12, L23, and S11 or L32, L7/L12, L24, and S11.

In this instance, the indicator preferably further includes mass-to-charge ratios m/z associated with L23, L24, S14, L32, and L7/L12, and may further include m/z associated with L23, L24, S14, L36, L32, and L7/L12.

Advantageous Effects of the Invention

In the microorganism identification method according to the present invention described thus far, the *Campylobacter* bacterial species may be reproducibly and expeditiously identified by using the marker protein selected from the ribosomal proteins that exhibit mutations specific to the *Campylobacter* bacteria.

This microorganism identification method uses, as marker protein, the marker protein selected from the ribosomal proteins that exhibit mutations specific to the *Campylobacter* bacteria, and further employs cluster analysis using, as indicator, mass-to-charge ratios m/z of marker protein-associated peaks marked on the mass spectrum. This method thus advantageously characterized may collectively identify at once bacteria of the genus *Campylobacter* possibly included in different samples.

BRIEF DESCRIPTION OF DRAWINGS

FIG. 3 is a table showing a list of bacterial species, subspecies, and strains of the genus *Campylobacter* used in an example.

FIG. 4 is a table showing a list of primers used in the example.

FIG. 5 is a table showing masses of amino acids.

FIG. 6 is a table showing a list of theoretical masses and actual values measured by the MALDI-TOF-MS of ribosomal proteins in the *Campylobacter* bacteria used in the example.

FIG. 11A is a table showing the assignment result of six ribosomal proteins determined based on measured values.

FIG. 11B is a table showing a relationship between theoretical mass values and assignment numbers of FIG. 11A.

FIG. 11C is a dendrogram drawn by using the six ribosomal proteins of FIG. 11A.

FIG. 15A is a table showing the assignment result of another combination of three ribosomal proteins determined based on measured values (serotyping).

FIG. 15B is a table showing a relationship between theoretical mass values and assignment numbers of FIG. 15A.

FIG. 15C is a dendrogram drawn by using the three ribosomal proteins of FIG. 15A.

DESCRIPTION OF EMBODIMENTS

An embodiment of the microorganism identification method according to the present invention is hereinafter described in detail.

Figure 1:
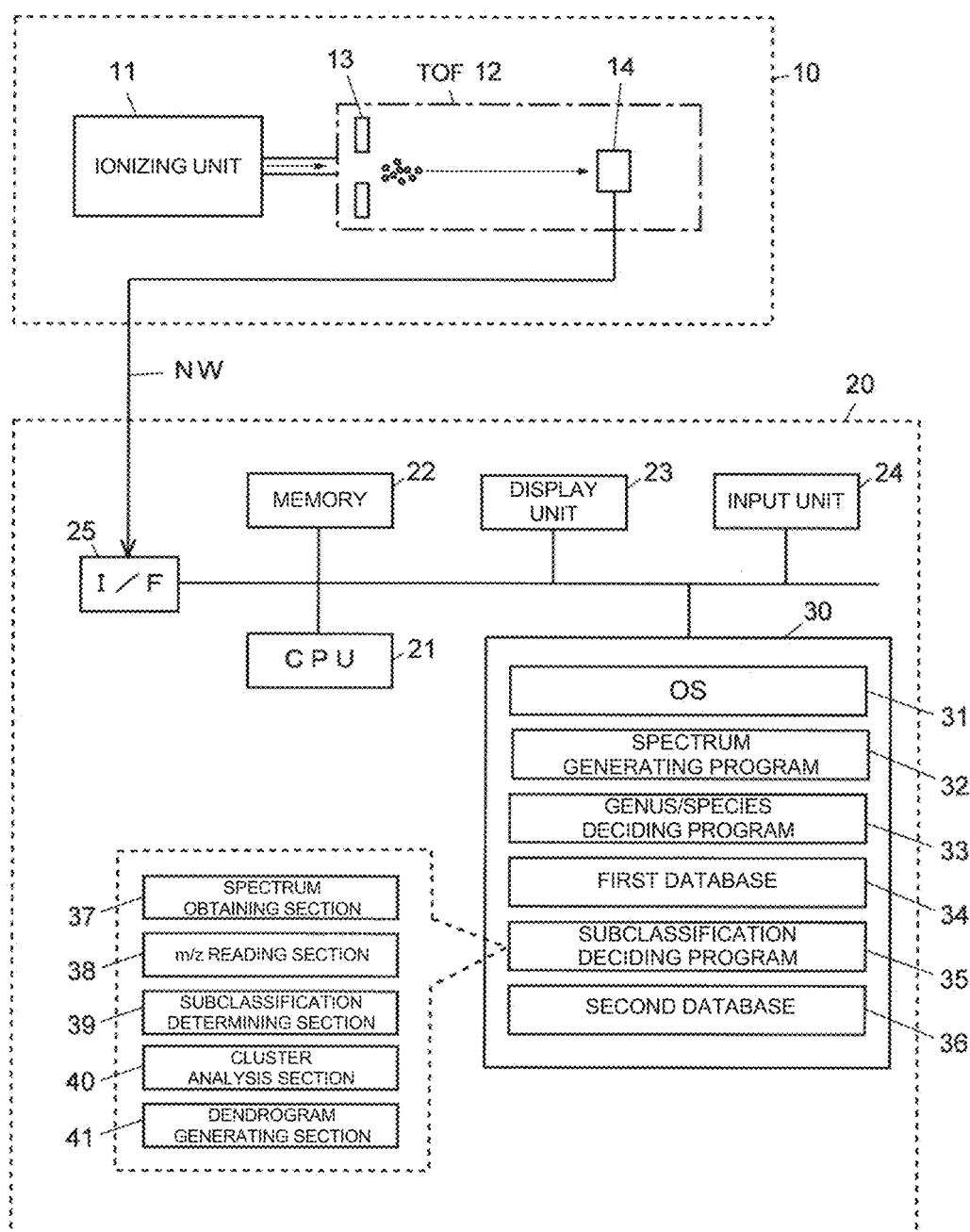
FIG. 1 is a block diagram illustrating principal structural elements of a microorganism identification system used with the microorganism identification method according to the present invention.
Figure 2:
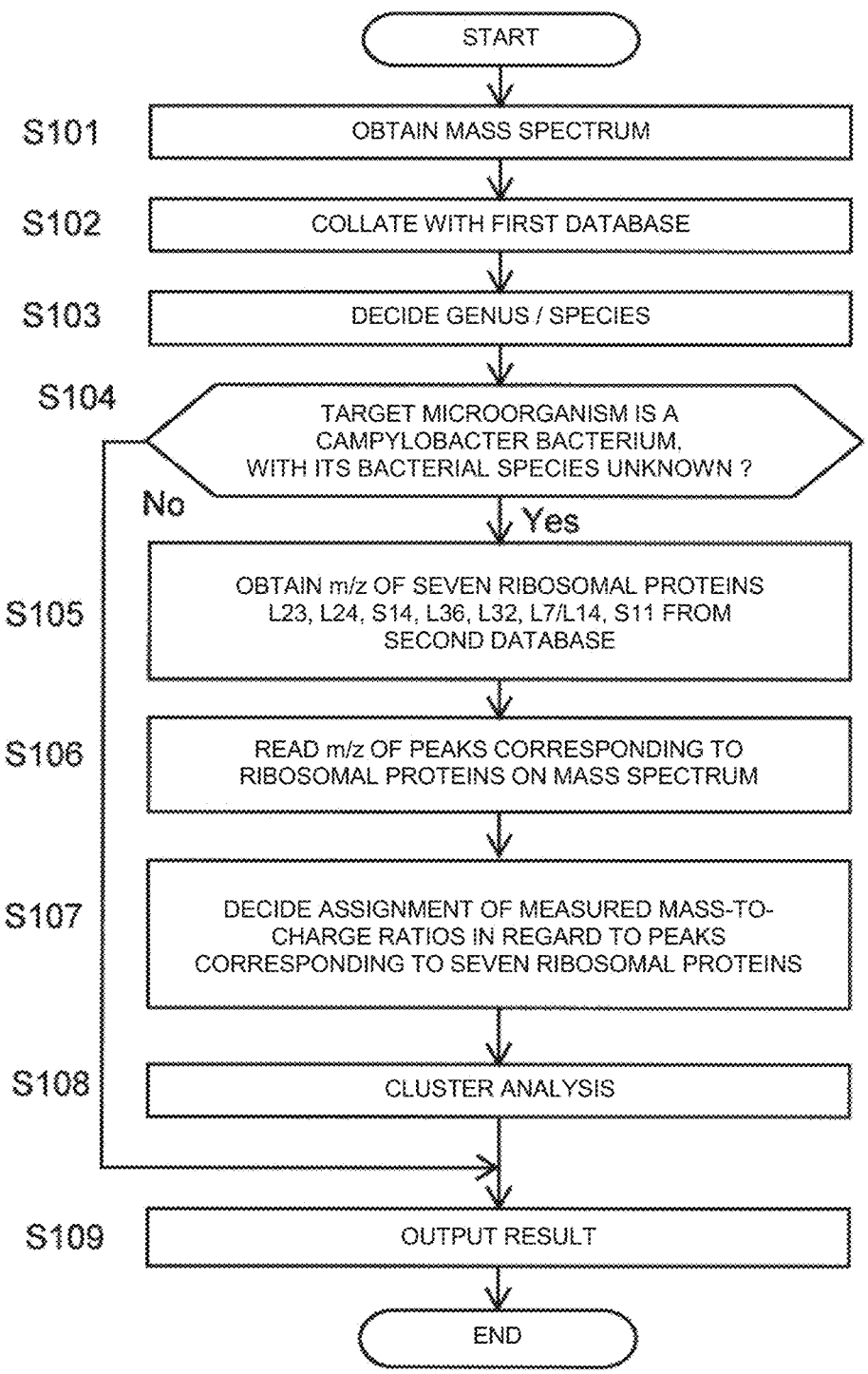
FIG. 2 is a flow chart of steps illustrated by way of an example, in the microorganism identification method according to the present invention.

FIG. 1 is a block diagram, illustrating the overall structure of a microorganism identification system used with the microorganism identification method according to the present invention. Main structural elements of this microorganism identification system are a mass spectrometric device 10 and a microorganism discriminating device 20. The mass spectrometric device 10 includes an ionizing unit 11 and a time-of-flight mass segregating unit (TOF) 12. The ionizing unit 11 ionizes molecules and atoms in a sample using the Matrix Assisted Laser Desorption-ionization (MALDI). The time-of-flight mass segregating unit 12 segregates various ions emitted from the ionizing unit 11 in accordance with mass-to-charge ratios.

The TOF 12 includes a feeder electrode 13 and a detector 14. The feeder electrode 13 draws ions out of the ionizing unit 11 and guides the ions into an ion-flying space formed in the TOF 12. The detector 14 detects the ions subjected to mass segregation in the ion-flying space.

A computer such as a work station or a personal computer constitutes the microorganism discriminating device 20. The microorganism discriminating device 20 includes a Central Processing Unit (CPU) 21, a memory 22, a display unit 23 including, for example, Liquid Crystal Display (LCD), an input unit 24 including, for example, a keyboard and a mouse, and a storage unit 30 including a mass storage device such as a hard disc and/or a Solid State Drive (SSD). The memory 22, display unit 23, input unit 24, and storage unit 30 are interconnected and coupled to the CPU 21. The storage unit 30 is a storage for an Operating System (OS) 31, a spectrum generating program 32, a genus/species deciding program 33, a subclassification deciding program 35 (program according to the present invention), a first database 34, and a second database 36. The microorganism discriminating device 20 is further equipped with an interface (I/F) 25 that allows for direct connection with an external device and indirect connection with an external device through a network such as Local Area Network (LAN). The microorganism discriminating device 20 is coupled through the interface 25 to the mass spectrometric device 10 with a network cable NW (or through wireless LAN).

Referring to FIG. 1, a spectrum obtaining section 37, an m/z reading section 38, a subclassification determining section 39, a cluster analysis section 40, and a dendrogram (genealogical chart) generating section 41 are illustrated in the form of a tree view expanded from the subclassification deciding program 35. These sections are essentially functional means implemented in a software-based manner when the CPU 21 runs the subclassification deciding program 35. The subclassification deciding program 35 is not necessarily an independent program. The subclassification deciding program 35 may be configured otherwise, for example, as a function embedded in part of a genus/species deciding program 33 or a program run to control the mass spectrometric device 10. The genus/species deciding program 33 may be selected from, for example, programs configured to identify microorganisms using the known finger print method.

In FIG. 1, the spectrum generating program 32, genus/species deciding program 33, subclassification deciding program 35, first database 34, and second database 36 are installed in a terminal operated by a user. Instead, at least some of these programs and databases or all of them may be installed in a different apparatus coupled to the terminal through a computer network. In this instance, the databases and/or the programs installed in the apparatus may be accessed and/or processed under instructions transmitted from the terminal.

The first database 34 of the storage unit 30 contains a vast number of mass lists registered relating to the known microorganisms. The mass lists each contain a list of mass-to-charge ratios of ions detected in the mass spectrometry of a microbial cell, and further contain, in addition to the mass-to-charge ratio information, at least information on a taxonomic group (taxonomic information) that the microbial cell belongs to (for example, family, genus, species). Such mass lists may desirably be generated based on real data obtained through mass spectrometry of microbial cells by using similarionization and mass segregation methods to the methods employed by the mass spectrometric device 10 (actually measured data).

To generate the mass list from actually measured data, first, peaks that appear in a predetermined range of mass-to-charge ratios are extracted from a mass spectrum obtained as the measured data. At the time, peaks associated with proteins may be mostly extracted by setting the predetermined range of mass-to-charge ratios to approximately 2,000 to 35,000, and undesired peaks (noise) may be removed by selectively extracting any peak of a height (relative intensity) greater than or equal to a predetermined threshold. Because of abundant ribosomal proteins being expressed in cells, when an appropriate value is set as the threshold, most of the mass-to-charge ratios recited in the mass lists may be associated with ribosomal proteins. Then, a list of mass-to-charge ratios (m/z) of the peaks thus extracted is registered per cell, with the taxonomic information appended thereto, in the first database 34. Importantly, culturing conditions for microbial cells used to obtain the measured data may desirably be standardized beforehand to minimize possible variability of gene expression under different culturing conditions.

In the second database 36 of the storage unit 30 is registered information relating to marker proteins used to identify the known microorganisms to the level of a lower taxonomic rank than species (for example, subspecies, pathotype, serotype, strain). The marker protein-related information includes at least information on mass-to-charge ratios (m/z) of the marker proteins in the known microorganisms. In the second database 36 according to this embodiment is stored information relating to marker proteins used to determine whether a test target microorganism is any one of bacteria of the genus *Campylobacter*. This information stored in the second database 36 specifically contains values of mass-to-charge ratios of at least the following ribosomal proteins, S10, L23, S19, L22, L16, 129, S17, L14, L24, S14, L18, L15, L36, S13, S11 (Me), L32, and L7/L12. The values of these mass-to-charge ratios of the ribosomal proteins will be described later in detail.

The values of the mass-to-charge ratios of the marker proteins stored in the second database 36 may desirably be selected and decided through comparison of mass-to-charge ratios actually measured to calculated masses obtained by translating base sequences of the respective ribosomal proteins into amino acid sequences. The base sequences of the marker proteins may be decided by sequencing or may be obtained from a public database, for example, National Center for Biotechnology Information (NCBI) database. To obtain the calculated masses from the amino acid sequences, the excision of N-terminal methionine residue may desirably be taken into account as posttranslational modification. Specifically, a theoretical value may be calculated based on the assumption that N-terminal methionine is excised when the second amino acid residue to the last is Gly, Ala, Ser, Pro, Val, Thr, or Cys. Since it is proton-attached molecules that are observed in the MALDI-TOF MS, the calculated masses may desirably be obtained, with protons being included in the calculation (theoretical values of mass-to-charge ratios of ions obtained by analysis of the proteins using the MALDI-TOF MS).

Steps of an operation to identify bacteria of the genus *Campylobacter* using the microorganism identification method according to this embodiment are hereinafter described with reference to a flow chart.

First, a user prepares a sample containing components of a test target microorganism, sets the prepared sample in the mass spectrometric device 10, and prompts the mass spectrometric device 10 to start mass spectrometry. The sample prepared then may be a cell extract or a material prepared by refining cell components, such as ribosomal proteins, in the cell extract. Optionally, a bacteria or cell suspension may be directly used as the sample.

The spectrum generating program 32 obtains a detection signal from the detector 14 of the mass spectrometric device 10 through the interface 25, and then generates a mass spectrum of the microorganism based on the detection signal (Step S101).

The genus/species deciding program 33 collates the mass spectrum of the target microorganism with the mass lists of the known microorganisms stored in the first database 34, and then extracts the mass list of a known microorganism whose mass-to-charge ratio has a pattern similar to that of the mass spectrum of the target microorganism, for example, a mass list abundantly including peaks that are substantially consistent with peaks on the mass spectrum of the target microorganism within a predetermined error range (Step S102). Then, the genus/species deciding program 33 consults the taxonomic information stored in the first database 34 in connection with the mass list extracted in Step S102 and identifies species of the known microorganism corresponding to the extracted mass list (Step S103). In case the species is found to be none of bacteria of the genus *Campylobacter* (No in Step S104), the species is outputted to the display unit 23 as species of the target microorganism (Step S116), and the operation ends. In case the species is found to be one of bacteria of the genus *Campylobacter* (Yes in Step S104), the operation proceeds to steps executed by the subclassification deciding program 35. In case the presence of any bacteria of the genus *Campylobacter* is already determined and confirmed by any other means, the operation may skip the species deciding program using the mass spectrum and directly proceed to the steps of the subclassification deciding program 35.

In the subclassification deciding program 35, the subclassification determining section 39 reads, from the second database 36, the mass-to-charge ratio values of the following seven ribosomal proteins L23, L24, S14, L36, L32, L7/L12, and S11 which are marker proteins (Step S105). Then, the spectrum obtaining section 37 obtains the mass spectrum of the target microorganism generated in Step S101. The m/z reading section 38 selects, as peaks corresponding to the marker proteins, peaks that appear on the mass spectrum within a range of mass-to-charge ratios stored in the second database 36 in association with the marker proteins, and then reads their mass-to-charge ratios (Step S106). Then, cluster analysis is executed, with the read mass-to-charge ratios being used as indicator. Specifically, the subclassification determining section 39 compares these mass-to-charge ratios to the mass-to-charge ratios of the marker proteins read from the second database 36 and decides assignment of the proteins based on the read mass-to-charge ratios (Step S107). Then, species of the target microorganism is determined by cluster analysis executed based on the decided assignment (Step S108) and is outputted to the display unit 23 as the identification result of the target microorganism (Step S109).

While the embodiment of the present invention was described thus far with reference to the accompanying drawings, the present invention includes but is not limited to the embodiment and may be variously modified within the scope and spirit of the present invention.

EXAMPLE (1) Bacterial Strains Used

Bacteria of the genus *Campylobacter* used for analysis were obtained from the Collections of Bacterial Strains illustrated in FIG. 3; RIKEN, Japan, Bioresource Center, Microbe Division (JCM) (located in Tsukuba city, Japan), and American Type Culture Collection (Manassas, Va. USA). The serotypes of *Campylobacter jejuni* (Penner serotypes) were decided according to the *Campylobacter* antiserum "SEMEN" (DENKA SEIKEN Co., Ltd.).

(2) DNA Analysis

The inventors conducted DNA sequence analysis for ribosomal protein genes in S10-spc-alpha operons using primers illustrated in FIG. 4 which were designed based on upstream and downstream consensus sequences in a target region of genome-sequenced strain. Specifically, genomes were extracted from bacterial strains by a conventional means and used as template to perform the PCR using KOD plus and amplify a target gene region. The obtained PCR product was purified and used as template for sequence analysis. In the sequence analysis was used Big Dye ver. 3.1 Cycle Sequencing Kit (Applied Biosystems, Foster City, Calif., US). Subsequent to transformation into amino acid sequences of genes from their DNA sequences, mass-to-charge ratios were calculated based on masses of amino acids illustrated in FIG. 5 and used as theoretical mass values.

(3) Analysis Using MALDI-TOF MS

The sample prepared for analysis was bacteria grown in Trypticase Soy Agar with 5% sheep blood (Becton, Dickinson and Company, Tokyo, Japan) or EG MEDIUM culture medium. The prepared sample in an amount approximately equivalent to one colony was added to and stirred in 10 μL of a sinapic acid-containing matrix agent (20 mg/mL of sinapic acid added to a solution containing 50 v/v % of acetonitrile and 1 v/v % of trifluoroacetic acid (Wako Pure Chemical Industries, Ltd., Osaka, Japan)). Then, 1.2 μL of the resulting material was dropped on a sample plate and naturally dried. The AXIMA Microorganism Identification System (Shimadzu Corporation, Kyoto, Japan) was used for measurements using the MALDI-TOF MS, in which the sample was measured under the conditions; positive linear mode, and spectral range of 2,000 m/z to 35,000 m/z. The theoretical mass values calculated by the method described earlier were matched to the measured mass-to-charge ratios within the margin of error of 500 ppm, Which were then reviewed and corrected as appropriate. Colon bacillus DH5 α was used for calibration of a mass spectrometer, and mass spectrometry was carried out as directed in the instruction manual.

(4) Building a Database for Identifying Bacterial Strains of the Genus *Campylobacter*

Figure 6:
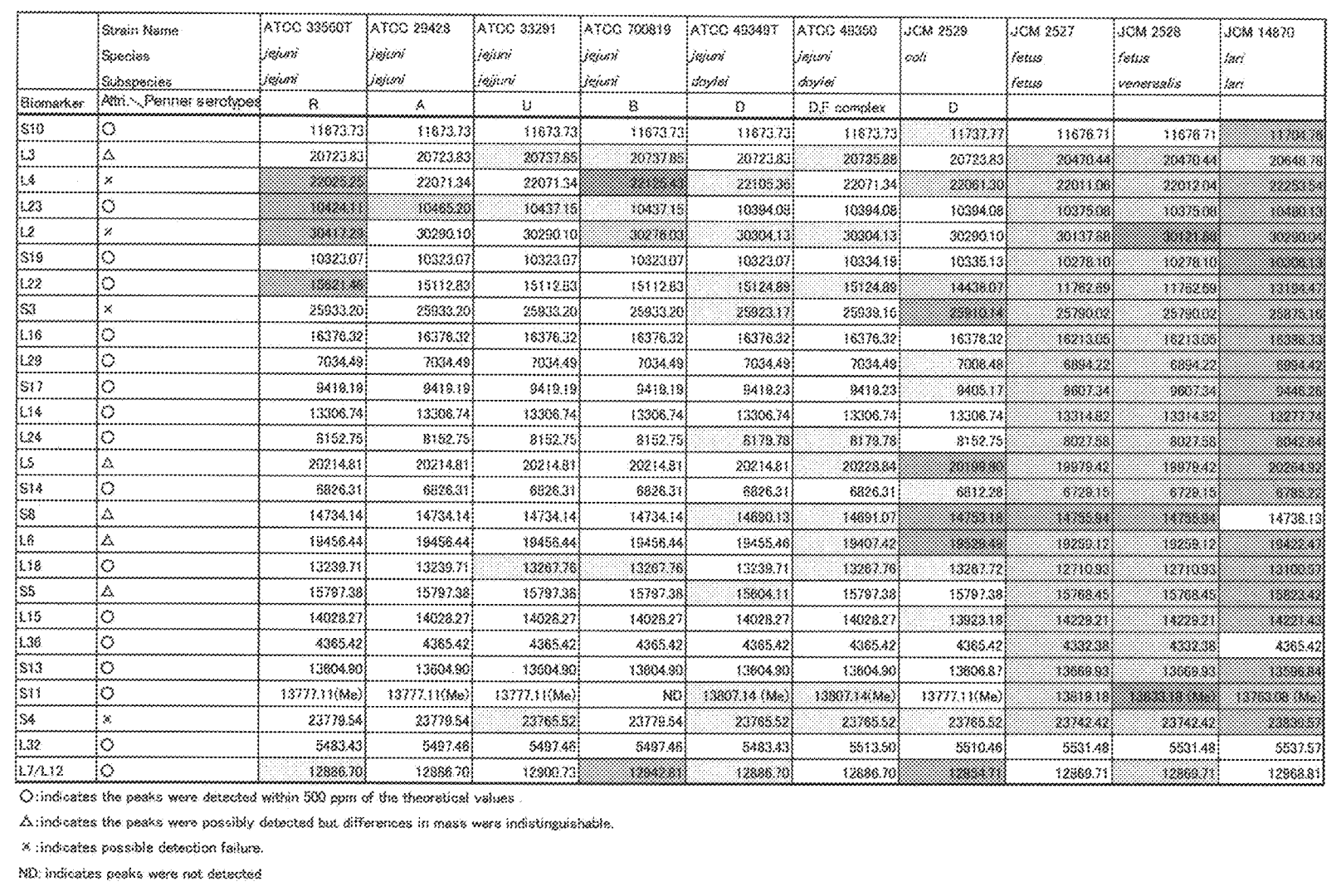

The theoretical mass values of the ribosomal proteins obtained as described in (2) were collated with the peak chart obtained by the MALDI-TOF MS in (3), which confirmed no difference between the measured values and the theoretical mass values calculated from gene sequences as for any proteins actually detected. Then, a test was conducted to look into a relationship between theoretical mass values and measured values of ribosomal proteins in S10-spc-α operons and other 26 ribosomal proteins as potential biomarkers Which differed in mass with different strains. FIG. 6 shows the result of this test.

FIG. 6 is a table showing theoretical mass values of mass-to-charge ratios (m/z) calculated from genes and actually measured mass peaks, marked with circle, triangle, and cross, of bacterial species of the genus *Campylobacter*. The peaks marked with circle were detected within 500 ppm of the theoretical values in default peak selling of the AXIMA Microorganism Identification System (Threshold offset: 0.015 mV, Threshold response: 1.200). The cross indicates possible detection failure, and the triangle indicates that differences to theoretical mass values in bacterial strains or peaks of the other proteins were less than or equal to 500 ppm, suggesting that peaks were possibly detected but differences in mass were indistinguishable. Among the 26 ribosomal proteins listed in FIG. 6, methylation occurred with S11 in some bacterial species, in which case the mass-to-charge ratios subsequent to the methylation were the theoretical mass values and collated with the measured values. In FIG. 6, the theoretical values with (Me) indicate the mass-to-charge ratios subsequent to the methylation used as theoretical mass value.

As is known from FIG. 6, theoretical mass values of the ribosomal proteins coded in S10-spc-alpha operons, S10, L23, L22, L16, L29, S17, L14, L24, S14, L18, L15, L36, S11, and S13 and other ribosomal proteins L32 and L7/L12 (16 ribosomal proteins in total) are variable with different bacterial strains of the genus *Campylobacter*. This may demonstrate that these ribosomal proteins are very useful protein markers for strain identification.

However, the ribosomal proteins, S10, L22, L16, L29, S17, L14, L18, L15, and S13, include admixture peaks, which may be considered unsuitable as biomarker. On the other hand, seven ribosomal proteins, L23, L24, S14, L36, S11, L32, and L7/L12, are expected to ensure detection stability irrespective of bacterial strains, and differences in mass with different bacterial strains were greater than or equal to 500 ppm. These seven ribosomal proteins were accordingly found to be useful biomarkers for identification of bacterial strains of the genus *Campylobacter* using the MALDI-TOF MS. In the test hereinafter described, these seven ribosomal proteins were used as biomarker.

(5) Software-Based Assignment of Measured Values by the MALDI-TOF MS

First, the theoretical mass values of the before-mentioned seven ribosomal proteins were registered in a software application described in Patent Literature 2.

Figures 7A, 7B, 7C:
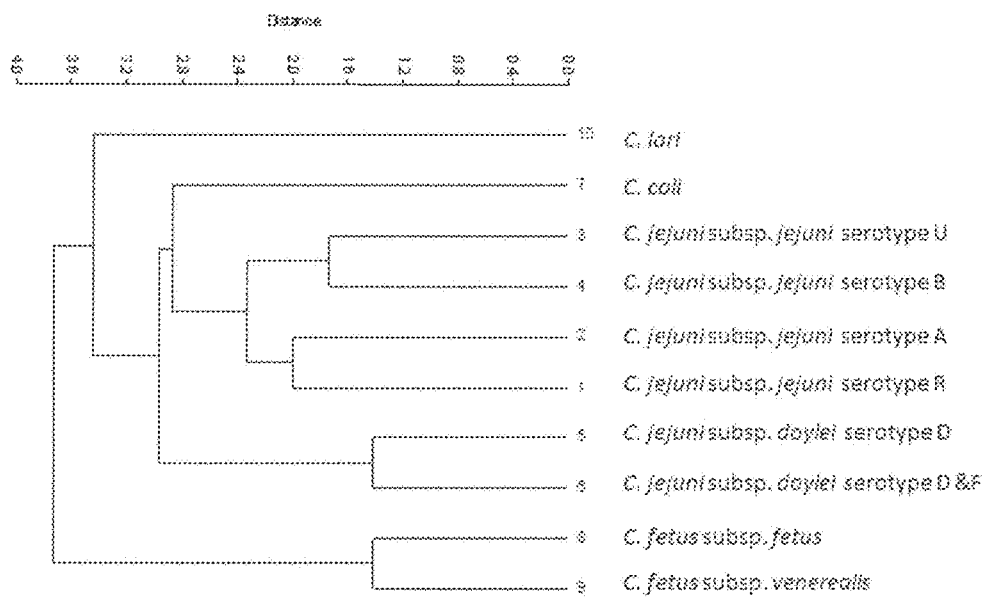
FIG. 7A is a table showing the assignment result of seven ribosomal proteins determined based on measured values.
FIG. 7B is a table showing a relationship between theoretical mass values and assignment numbers of FIG. 7A.
FIG. 7C is a dendrogram drawn by using four of the ribosomal proteins of FIG. 7A.

Measured values obtained by the MALDI-TOF MS were analyzed by the software to check whether the respective biomarkers were correctly assignable to the registered mass peaks, and the mass peaks of all of the biomarkers were consequently assigned to the registered mass numbers for all of the bacterial strains, as illustrated in FIG. 7A. FIG. 7B shows a relationship between the registered theoretical mass values and assignment numbers. In comparison to Penner serotypes, Penner serotypes of *Campylobacter jejuni* were respectively identified as A, B, D, DF complex, U, and R.

Further, mass patterns of *Campylobacter jejuni* (assignment result) were subjected to cluster analysis, the result of which was outputted in the form of a binary graph to generate a dendrogram using dendrogram generating software called Past (FIG. 7C). As a result, subspecies of *Campylobacter jejuni*; subsp. *jejuni*, and subsp. *doylei* were identified, which were all displayed in subtrees. Subspecies of *Campylobacter fetus*; subsp. *fetus*, and subsp. *venerealis*, were also successfully identified. Thus, the seven biomarkers were found to be useful for identifying species and subspecies of the genus *Campylobacter*.

The names of the biomarkers found to be useful in this example are the same as in the mass peaks, *C. coli* L7/L12: 12854Da and *C. jejuni* S13: 13735Da, reported in Non Patent Literature 13. In this example, accurate peaks were calculated from the gene information and collated with the measured values, and biomarkers including many admixture peaks, like L29 used in Non Patent Literature 15, were ruled out. Thus, a very reliable mass database may be available now for the first time.

(6) Comparison with Finger Print Method (SARAMIS)

Figures 8, 9:
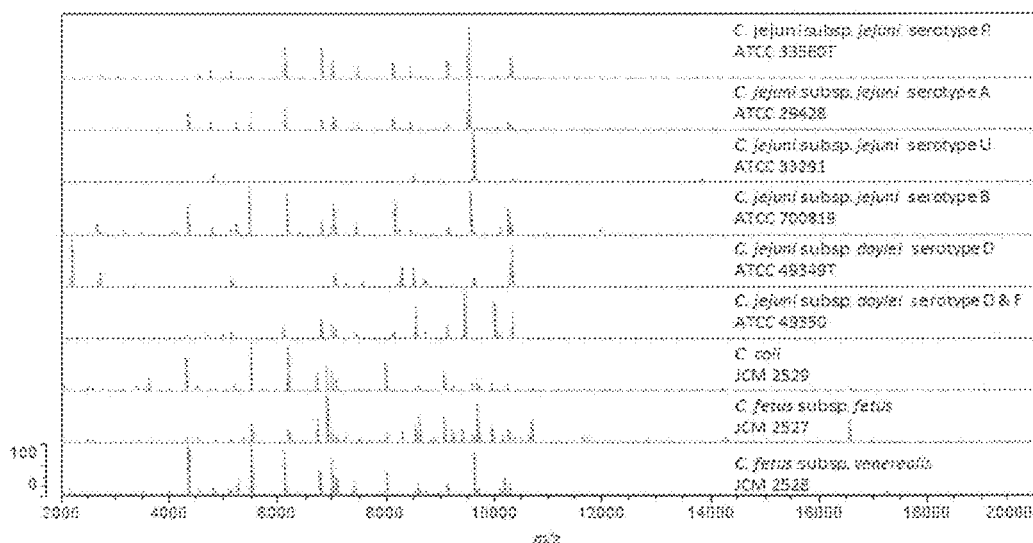
FIG. 8 is a chart obtained from measurements by the MALDI-TOF MS.
FIG. 9 is an identification result obtained by the SARAMIS.

The identification result using the theoretical mass values of biomarkers shown in Table 6 as indicator were compared with the identification result using the existing finger print method (SARAMIS). First, the chart illustrated in FIG. 8 was obtained from the MALDI-TOF MS measurements, the result of which was analyzed by the SARAMIS, as directed in the instruction manual of the AXIMA Microorganism Identification System. FIG. 9 is a table showing the result obtained by the analysis. *Campylobacter jejuni* subsp. *doylei* ATCC49350 was identified as *Campylobacter jejuni* by such a low percentage as 76%. As for *Campylobacter jejuni* subsp. *doylei* ATCC49349, its genus was not even identified probably because the SARAMIS has no database that can be consulted for matching. *Campylobacter coli*, *Campylobacter jejuni* subsp. *jejuni*, *Campylobacter fetus* subsp. *fetus*, *Campylobacter fetus* subsp. *venerealis*, and *Campylobacter lari* subsp. *lari* were accurately identified down to the level of species by 95% or more. None of these bacteria was identified to the level of subspecies.

Figure 10:
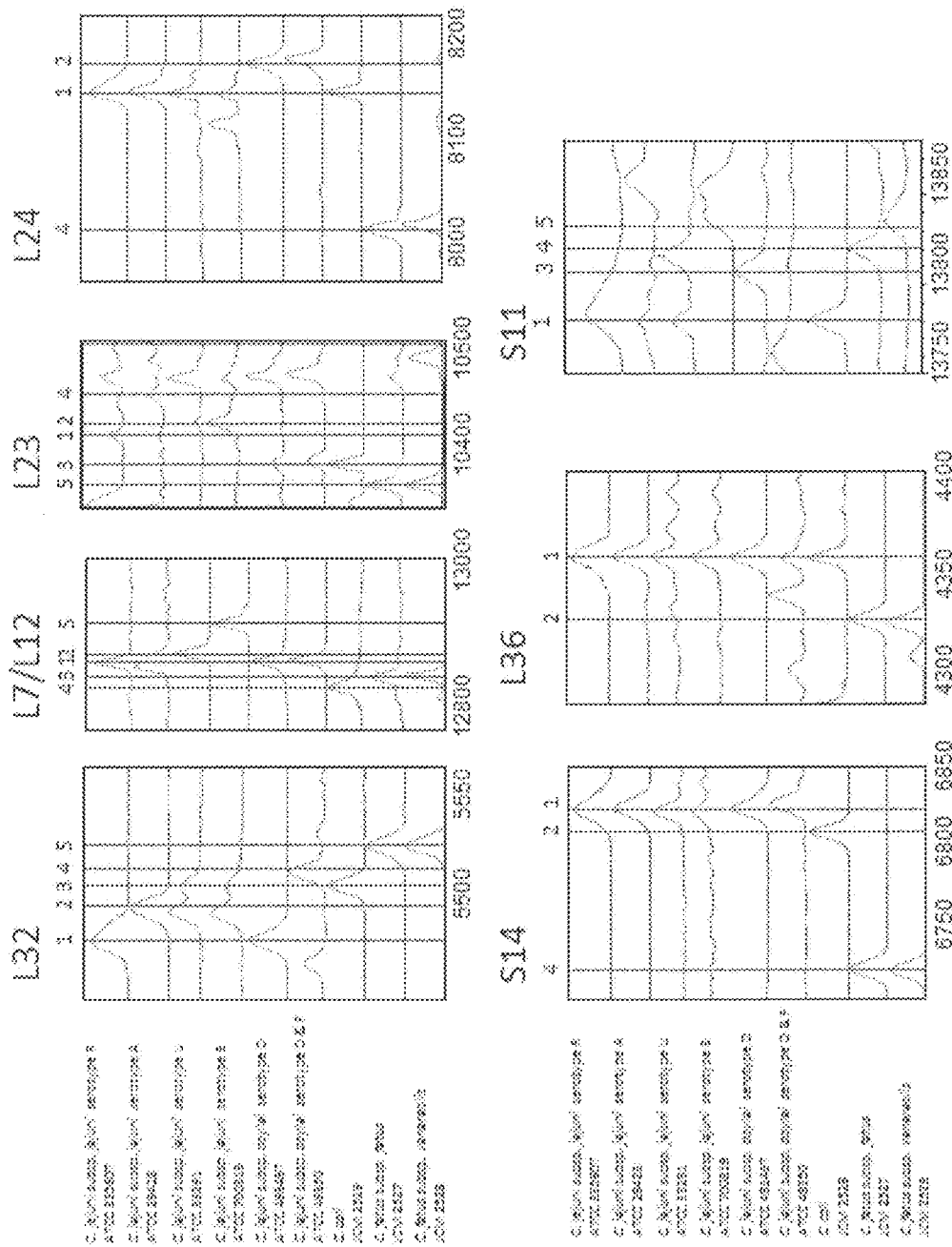
FIG. 10 is a drawing presenting peak charts obtained from measurements by the MALDI-TOF MS.

The inventors attempted to find out whether different subspecies strains are identifiable based on the database of theoretical mass values illustrated in FIG. 8A. FIG. 10 shows, in an enlarged view, peaks of seven of the biomarkers in the chart of FIG. 8. As is known from FIG. 10, the respective biomarker masses being shifted allow for clear distinction between the peaks. Comparison to measured values of the seven biomarkers and subsequent assignment resulted in the same outcome as shown in FIG. 7A.

While the example used the seven ribosomal proteins as marker protein to identify species and subspecies of the genus *Campylobacter*, marker proteins usable for this purpose include but are not limited to these ribosomal proteins. FIGS. 11A to 11C show results obtained from a dendrogram generated based on cluster analysis performed with the assignment result of six of the seven ribosomal biomarkers from which the ribosomal protein S11 has been excluded. According to this method, as illustrated in FIG. 11C, subspecies of *Campylobacter jejuni*; subsp. *jejuni*, and subsp. *doylei* were identified, which were all displayed in subtrees. Subspecies of *Campylobacter fetus*, on the other hand, failed to be identified, while species of *Campylobacter jejuni* and *Campylobacter fetus* were identified. This result may demonstrate that these six biomarkers are very useful for identifying bacterial species of the genus *Campylobacter* and identifying subspecies of *Campylobacter jejuni*.

Figures 12A, 12B, 12C:
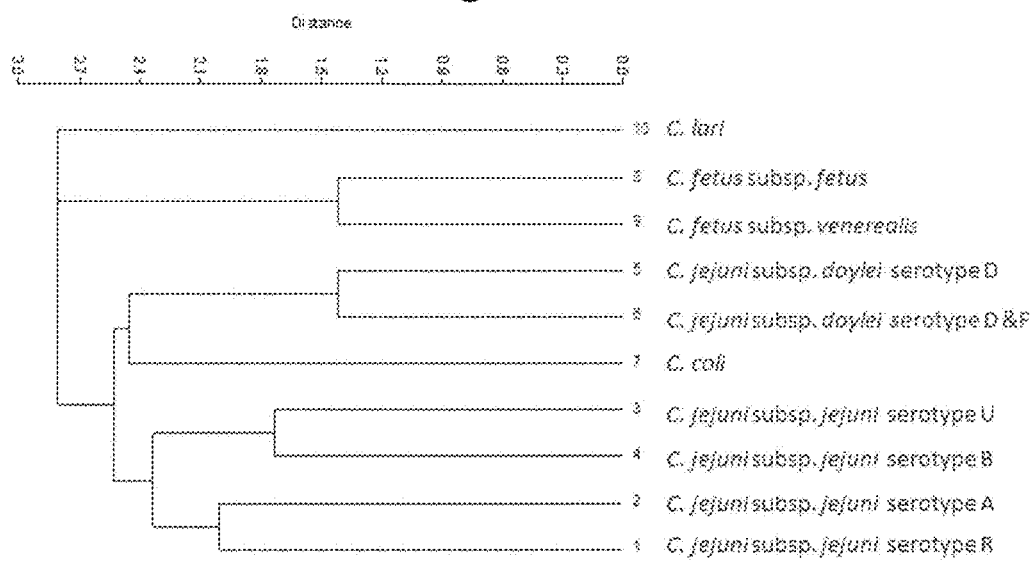
FIG. 12A is a table showing the assignment result of four ribosomal proteins determined based on measured values.
FIG. 12B is a table showing a relationship between theoretical mass values and assignment numbers of FIG. 12A.
FIG. 12C is a dendrogram drawn by using the four ribosomal proteins of FIG. 12A.

FIGS. 12A to 12C show results obtained from a dendrogram generated based on cluster analysis of four ribosomal proteins L32, L7/L12, L23, and S11 performed with the assignment result of marker proteins. According to this method, bacterial species and subspecies of the genus *Campylobacter* were identified, although in a manner slightly different from the result of the seven ribosomal biomarkers (result of FIG. 8C). Therefore, these four ribosomal proteins were also found to be useful for identifying bacterial species and subspecies of the genus *Campylobacter*.

Figures 13A, 13B, 13C:
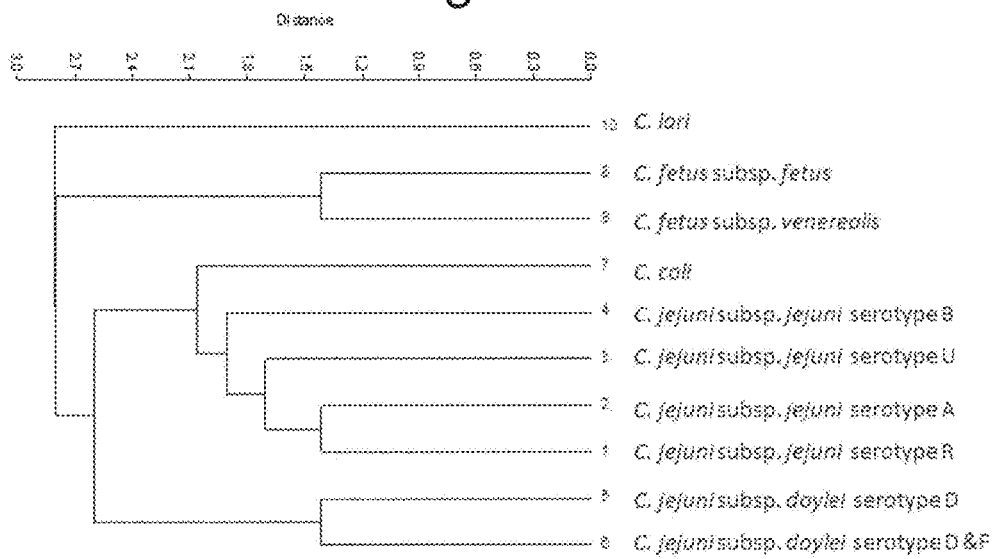
FIG. 13A is a table showing the assignment result of another combination of four ribosomal proteins determined based on measured values (serotyping).
FIG. 13B is a table showing a relationship between theoretical mass values and assignment numbers of FIG. 13A.
FIG. 13C is a dendrogram drawn by using the four ribosomal proteins of FIG. 13A.

FIGS. 13A to 13C show results obtained from a dendrogram generated based on cluster analysis of four ribosomal proteins L32, L7/L12, L24, and S11 performed with the assignment result of marker proteins. According to this method, bacterial species and subspecies of the genus *Campylobacter* were identified, although in a manner slightly different from the result of the seven ribosomal biomarkers (result of FIG. 8C). Therefore, these four ribosomal proteins were also found to be useful for identifying bacterial species and subspecies of the genus *Campylobacter*.

Figures 14A, 14B, 14C:
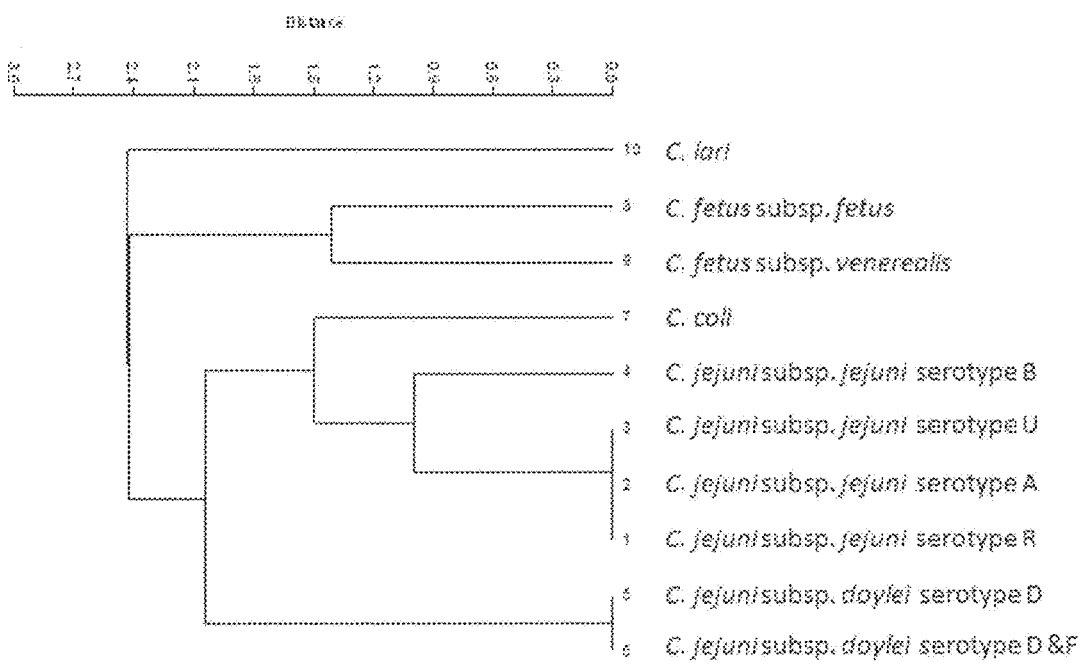
FIG. 14A is a table showing the assignment result of three ribosomal proteins determined based on measured values serotyping).
FIG. 14B is a table showing a relationship between theoretical mass values and assignment numbers of FIG. 14A.
FIG. 14C is a dendrogram drawn by using the three ribosomal proteins of FIG. 14A.

FIGS. 14A to 14C show results obtained from a dendrogram generated based on cluster analysis of three ribosomal proteins L24, S14, and S11 performed with the assignment result of marker proteins. This method succeeded in identifying bacteria of the genus *Campylobacter*, while failing to identify subspecies of *Campylobacter jejuni*.

FIGS. 15A to 15C show results obtained from a dendrogram generated based on cluster analysis of three ribosomal proteins L24, S14, and L36 performed with the assignment result of marker proteins. This method succeeded in identifying bacteria of the genus *Campylobacter*, while failing to identify subspecies of *Campylobacter jejuni* or subspecies of *Campylobacter fetus*.

(7) Amino Acid Sequences and Gene Sequences of Biomarkers

A list of sequence ID numbers show DNA sequences and amino acid sequences of six ribosomal proteins in different bacterial strains of the genus *Campylobacter* which showed theoretical mass values variable with the difference bacterial strains. These six ribosomal proteins include L23, L24, S14, and L36 coded in S10-spc-alpha operons, and L32 and L7/L12 coded outside of the S10-spc-alpha operons.

REFERENCE SIGNS LIST

10 . . . mass spectrometric device
11 . . . ionizing unit
12 . . . TOF
13 . . . feeder electrode
14 . . . detector
20 . . . microorganism discriminating device
21 . . . CPU
22 . . . memory
23 . . . display unit
24 . . . input unit
25 . . . I/F
30 . . . storage unit
31 . . . OS
32 . . . spectrum generating program
33 . . . genus/species deciding program
34 . . . first database
35 . . . subclassification deciding program
36 . . . second database
37 . . . spectrum obtaining section
38 . . . m/z reading section
39 . . . subclassification determining section
40 . . . cluster analysis section
41 . . . dendrogram generating section

The invention claimed is:

1. A microorganism identification method comprising steps of:
   a) obtaining a mass spectrum through mass spectrometry of a sample including microorganisms;
   b) reading, from the mass spectrum, a mass-to-charge ratio m/z of a peak associated with a marker protein; and
   c) identifying which bacterial species of the genus *Campylobacter* are included in the microorganisms in the sample based on the mass-to-charge ratio m/z, wherein
   the marker protein is at least one ribosomal protein selected from the group consisting of L23, S14, L36, S11 (Me), and L32.

2. The microorganism identification method according to claim 1, wherein
   the bacterial species of the genus *Campylobacter* is any one selected from the group consisting of *Campylobacter jejuni* subsp. *jejuni*, *Campylobacter jejuni* subsp. *doylei*, *Campylobacter coli*, *Campylobacter fetus*, and *Campylobacter lari*.

3. The microorganism identification method according to claim 2, wherein
   the bacterial species of the genus *Campylobacter* is *Campylobacter jejuni* subsp. *jejuni*, and
   the marker protein includes at least any one of L32, L23, and S14.

4. The microorganism identification method according to claim 2, wherein
   the bacterial species of the genus *Campylobacter* is *Campylobacter Coli*, and
   the marker protein includes at least any one selected from L32, S14, and L23.

5. The microorganism identification method according to claim 2, wherein
   the bacterial species of the genus *Campylobacter* is *Campylobacter fetus*.

6. The microorganism identification method according to claim 2, wherein
   the bacterial species of the genus *Campylobacter* is *Campylobacter lari*, and
   the marker protein includes at least one of L23, and L32.

7. The microorganism identification method according to claim 2, wherein
   when the bacterial species of the genus *Campylobacter* is *Campylobacter jejuni*, it is identified as having serotype R, and
   the marker protein includes at least L23.

8. The microorganism identification method according to claim 2, wherein
   when the bacterial species of the genus *Campylobacter* is *Campylobacter jejuni*, it is identified as having serotype A, and
   the marker protein includes at least L23 or L32.

9. The microorganism identification method according to claim 2, wherein
   when the bacterial species of the genus *Campylobacter* is *Campylobacter jejuni*, it is identified as having serotype B.

10. The microorganism identification method according to claim 2, wherein
    when the bacterial species of the genus *Campylobacter* is *Campylobacter jejuni*, it is identified as having serotype U.

11. The microorganism identification method according to claim 2, wherein
    when the bacterial species of the genus *Campylobacter* is *Campylobacter jejuni*, it is identified as having serotype D, and
    the marker protein includes at least L32 and L23.

12. The microorganism identification method according to claim 2, wherein
when the bacterial species of the genus *Campylobacter* is *Campylobacter jejuni*, it is identified as having serotype DF complex, and
the marker protein includes at least L32.

13. The microorganism identification method according to claim 2, wherein cluster analysis using, as indicator, at least mass-to-charge ratios m/z associated with S14, and S11 is employed to determine which bacterial species of the genus *Campylobacter* are included in the microorganisms in the sample.

14. The microorganism identification method according to claim 13, wherein the indicator further includes at least mass-to-charge ratios m/z associated with S14, and L36.

15. The microorganism identification method according to claim 13, further comprising a step of generating a dendrogram that shows an identification result obtained by the cluster analysis.

16. The microorganism identification method according to claim 2, wherein the serotype when the bacterial species of the genus *Campylobacter* is *Campylobacter jejuni* is determined by employing cluster analysis using, as indicator, at least mass-to-charge ratios m/z associated with L32, L23, and S11 or L32, and S11.

17. The microorganism identification method according to claim 16, wherein the indicator further includes mass-to-charge ratios m/z associated with L23, S14, and L32.

18. The microorganism identification method according to claim 16, wherein the indicator further includes m/z associated with L23, S14, L36, and L32.

* * * * *

```
                       SEQUENCE LISTING

<160> NUMBER OF SEQ ID NOS: 153

<210> SEQ ID NO 1
<211> LENGTH: 147
<212> TYPE: DNA
<213> ORGANISM: Campylobacter jejuni ATCC 33560T

<400> SEQUENCE: 1
atggcagtac caaagagaag agtaagtaaa actcgtgcag ctaaacgcag aactcactat      60
aaagttagtc ttcctatgcc tgtaaaagac aaagatggaa gctacaaaat gcctcaccgt    120
gcgaatccaa caactaagga atattaa                                        147

<210> SEQ ID NO 2
<211> LENGTH: 378
<212> TYPE: DNA
<213> ORGANISM: Campylobacter jejuni ATCC 33560T

<400> SEQUENCE: 2
atggcaattt ctaaagaaga tgtattagaa tatatttcaa atttaagtgt tcttgagtta      60
tcagaacttg taaaagaatt tgaagaaaaa tttggtgtgt ctgctgctcc tgtaatggta    120
gctggtggtg ctgcagctgg tggtgctgca gctgctgctg aagaaaaaac tgaatttgat    180
atcgttttaa ctgatggcgg tgctaaaaag attgaagtta ttaaaatcgt tcgtgctctt    240
acaggccttg gtcttaaaga agcaaaagat gcagttgagc aaactccttc aactctaaaa    300
gagggtgtgg ctaaagctga agctgaggaa gctaaaaaac aacttgaaga agctggtgct    360
aaagtagaac ttaagtaa                                                  378
```

<210> SEQ ID NO 3
<211> LENGTH: 282
<212> TYPE: DNA
<213> ORGANISM: Campylobacter jejuni ATCC 33560T

<400> SEQUENCE: 3

| | | | | | |
|---|---|---|---|---|---|
| atggcagata | ttactgatat | aaagactata | ctttacacag | aaaaaagttt | gaatttgcaa | 60 |
| gagcaaggtg | tcgtagttat | tcaaacttca | ccaaagatga | ctaaaacagg | cttaaaagcg | 120 |
| gttttaaaag | agtattttgg | tgtaactcca | aaaagcatca | attcattaag | aatggatgga | 180 |
| aaagttaagc | gttttagagg | tcgtttaggt | caaagaaacg | attacaaaaa | attctatgtt | 240 |
| aagctacctg | aaggtgttag | cttagaaaat | acggaggctt | aa | | 282 |

<210> SEQ ID NO 4
<211> LENGTH: 234
<212> TYPE: DNA
<213> ORGANISM: Campylobacter jejuni ATCC 33560T

<400> SEQUENCE: 4

| | | | | | |
|---|---|---|---|---|---|
| atggcggtta | aattaaaaat | caaaaaaggt | gatagcgtta | aggttatcac | aggcgatgat | 60 |
| aaaggtaaaa | caggtaaagt | tttagcggta | tatccaaaaa | cacttaaagt | ggtagttgaa | 120 |
| ggatgtaaaa | tcgctaaaaa | agctattaag | ccgagtgaga | aaaacccaaa | tggtggtttt | 180 |
| atcaataaag | aaatgccaat | ggatatttcc | aatgtggcaa | aagttcagga | gtaa | 234 |

<210> SEQ ID NO 5
<211> LENGTH: 186
<212> TYPE: DNA
<213> ORGANISM: Campylobacter jejuni ATCC 33560T

<400> SEQUENCE: 5

| | | | | | |
|---|---|---|---|---|---|
| atggctaaaa | aatcaatgat | tgcaaaagcg | gcacgcaagc | ctaaatttaa | agttagagct | 60 |
| tatacaagat | gccaaatttg | tgggcgtccg | cattcggttt | atagagattt | tggaatttgc | 120 |
| agagtttgct | taagaaaaat | gggcaacgaa | ggtttgattc | caggtcttaa | gaaagcaagt | 180 |
| tggtaa | | | | | | 186 |

<210> SEQ ID NO 6
<211> LENGTH: 357
<212> TYPE: DNA
<213> ORGANISM: Campylobacter jejuni ATCC 33560T

<400> SEQUENCE: 6

| | | | | | |
|---|---|---|---|---|---|
| atgagagcaa | atgtattaaa | aagaaaacta | actttaagaa | tcaaaagaaa | aaaagaatt | 60 |
| agagcgaaaa | tttcaggttg | tgaaaattttt | ccaagaattt | ctgtatttaa | atcaaacaga | 120 |
| actctatata | tccaagcgat | tgatgatgta | aaagctgtaa | ctttagcagc | agttgatgga | 180 |
| cgcaaacttg | gcgttaaagc | aaataaagaa | ggtgctaaaa | aatcgctgc | tgaatttgct | 240 |
| aaaactttaa | aagctaaaaa | gatagaacaa | gctgtttttg | ataaaatgg | ttatgtatat | 300 |
| catggtgtta | tcgcagcatt | ggctgaatct | ttaagagaaa | atggcattag | gctataa | 357 |

<210> SEQ ID NO 7
<211> LENGTH: 114
<212> TYPE: DNA
<213> ORGANISM: Campylobacter jejuni ATCC 33560T

<400> SEQUENCE: 7

| | | | | | |
|---|---|---|---|---|---|
| atgaaagtga | gaccatcggt | taaaaagatg | tgcgacaagt | gcaaagtagt | tcgccgtaaa | 60 |

```
ggcgtggttc gcattatttg cgaaaatcca aaacataaac aaagacaagg ataa        114
```

<210> SEQ ID NO 8
<211> LENGTH: 393
<212> TYPE: DNA
<213> ORGANISM: Campylobacter jejuni ATCC 33560T

<400> SEQUENCE: 8

```
atggcaaaaa gaaaaatcgt aaagaaaaaa gtagttaaaa aaaatatagc aaaaggtatt    60
gtttatatca gtgcgacttt taacaatact atggttacag tgactgatga atgggaaat    120
gctatcgctt ggagtagtgc aggtggttta ggatttaaag gttctaaaaa atcaactcct   180
tatgcagcac aacaagcagt agaagacgct ttaaataaag caaagaaaca cggaattaaa   240
gaagtaggca ttaaagtaca aggaccagga agcggtagaa aaactgctgt taagagtgta   300
ggtgctatgg aaggaatcaa agtaactttc ttaaaagata tcactccatt agctcacaat   360
ggttgcagac cgcctaagcg tcgtcgtgtc taa                                393
```

<210> SEQ ID NO 9
<211> LENGTH: 147
<212> TYPE: DNA
<213> ORGANISM: Campylobacter jejuni ATCC 29248=JCM 2013

<400> SEQUENCE: 9

```
atggcagtac caaagagaag agtgagcaaa actcgtgcag ctaaacgcag aactcactat    60
aaagttagtc ttcctatgcc tataaaagac aaagatggaa gctacaaaat gcctcaccgt   120
gcgaatccaa caactaagga atattaa                                       147
```

<210> SEQ ID NO 10
<211> LENGTH: 378
<212> TYPE: DNA
<213> ORGANISM: Campylobacter jejuni ATCC 29248=JCM 2013

<400> SEQUENCE: 10

```
atggcaattt ctaaagaaga tgtattagaa tatatttcaa atttaagtgt tcttgagtta    60
tcagaacttg taaagaatt tgaagaaaaa tttggtgtgt ctgctgctcc tgtaatggta   120
gctggtggtg ctgcagctgg tggtgctgca gctgctgctg aagaaaaaac tgaatttgat   180
atcgttttaa ctgatggcgg tgctaaaaag attgaagtta ttaaaatcgt tcgtgctctt   240
acaggccttg gtcttaaaga agcaaaagat gcagttgagc aaactccttc aactctaaaa   300
gagggtgtgg ctaaagctga agctgaggaa gctaaaaaac aacttgaaga agctggtgct   360
aaagtagaac ttaagtaa                                                 378
```

<210> SEQ ID NO 11
<211> LENGTH: 282
<212> TYPE: DNA
<213> ORGANISM: Campylobacter jejuni ATCC 29248=JCM 2013

<400> SEQUENCE: 11

```
atggcagata ttactgatat aaagactata ctttacacag aaaaaagttt gaatttgcaa    60
gagcaaggtg tcgtagttat tcaaacttcg ccaaaaatga ctaaaacagg cttaaaagtg   120
gttttaaaag agtattttgg tgtaactcca aaaagcatca attccttaag aatggatgga   180
aaaattaagc gttttagagg tcgtttaggt caaagaaaca attacaaaaa attctatgtt   240
aagctacctg aaggtgttag cttagaaaat acggaggctt aa                      282
```

<210> SEQ ID NO 12
<211> LENGTH: 234
<212> TYPE: DNA
<213> ORGANISM: Campylobacter jejuni ATCC 29248=JCM 2013

<400> SEQUENCE: 12

```
atggcggtta aattaaaaat caaaaaaggt gatagcgtta aggttatcac aggcgatgat    60
aaaggtaaaa caggtaaagt tttagcggta tatccaaaaa cacttaaagt ggtagttgaa   120
ggatgtaaaa tcgctaaaaa agctattaag ccgagtgaga aaaacccaaa tggtggtttt   180
atcaataaag aaatgccaat ggatatttcc aatgtggcaa agttcagga gtaa          234
```

<210> SEQ ID NO 13
<211> LENGTH: 186
<212> TYPE: DNA
<213> ORGANISM: Campylobacter jejuni ATCC 29248=JCM 2013

<400> SEQUENCE: 13

```
atggctaaaa aatcaatgat tgcaaaagcg gcacgcaagc ctaaatttaa ggttagagct    60
tatacaagat gccaaatttg tgggcgtccg cattcggttt atagagattt tggaatttgc   120
agagtttgct taagaaaaat gggcaatgaa ggtttgattc caggtcttaa gaaagcaagt   180
tggtaa                                                              186
```

<210> SEQ ID NO 14
<211> LENGTH: 357
<212> TYPE: DNA
<213> ORGANISM: Campylobacter jejuni ATCC 29248=JCM 2013

<400> SEQUENCE: 14

```
atgagagcaa atgtattaaa agaaaaacta actttaagaa tcaaaagaaa aaaagaatt     60
agagcgaaaa tttcaggttg tgaaaatttt ccaagaattt ctgtatttaa atcaaacaga   120
actctatata tccaagcgat tgatgatgta aaagctgtaa ctttagcagc agttgatgga   180
cgcaaacttg gcgttaaagc aaataaagaa ggtgctaaaa aaatcgctgc tgaatttgct   240
aaaactttaa aagttaaaaa gatagaacaa gctgttttg atagaaatgg ttatgtatat    300
catggtgtta tcgcagcatt ggctgaatct ttaagagaaa atggcattag gctataa      357
```

<210> SEQ ID NO 15
<211> LENGTH: 114
<212> TYPE: DNA
<213> ORGANISM: Campylobacter jejuni ATCC 29248=JCM 2013

<400> SEQUENCE: 15

```
atgaaagtga gaccatcggt taaaagatg tgcgacaaat gcaaagtagt tcgccgtaaa     60
ggcgtggttc gcattatttg cgaaaatcca aaacataaac aaagacaagg ataa         114
```

<210> SEQ ID NO 16
<211> LENGTH: 393
<212> TYPE: DNA
<213> ORGANISM: Campylobacter jejuni ATCC 29428

<400> SEQUENCE: 16

```
atggcaaaaa gaaaaatcgt aaagaaaaaa gtagttaaaa aaaatatagc aaaaggtatt    60
gtttatatca gtgcgacttt taacaatact atggttacag taactgatga aatgggaaat   120
gctatcgctt ggagtagtgc aggtggttta ggatttaaag gttctaaaaa atcaactcct   180
tatgcagcac aacaagcagt agaagacgct ttaaataaag caaagaaca cggaattaaa    240
```

```
gaagtaggca ttaaagtaca aggaccagga agcggtagag aaactgctgt taagagtgta    300
ggtgctatgg aaggaatcaa agtaactttc ttaaaagata tcactccatt agctcacaat    360
ggttgcagac cgcctaagcg tcgtcgtgtc taa                                 393
```

```
<210> SEQ ID NO 17
<211> LENGTH: 147
<212> TYPE: DNA
<213> ORGANISM: Campylobacter jejuni ATCC 33291

<400> SEQUENCE: 17
atggcagtac caaagagaag agtgagcaaa actcgtgcag ctaaacgcag aactcactat     60
aaagttagtc ttcctatgcc tataaaagac aaagatggaa gctacaaaat gcctcaccgt    120
gcgaatccaa caactaagga atattaa                                        147

<210> SEQ ID NO 18
<211> LENGTH: 378
<212> TYPE: DNA
<213> ORGANISM: Campylobacter jejuni ATCC 33291

<400> SEQUENCE: 18
atggcaatct ctaaagaaga tgtattagaa tatatttcaa atttaagtgt tcttgagtta     60
tcagaacttg taaagagtt tgaagaaaaa tttggtgtgt ctgctgctcc tgtaatgata    120
gctggtggtg ctgcagctgg tggtgctgca gctgctgctg aagaaaaaac tgaatttgat    180
atcgttttaa ctgatggcgg tgctaaaaag attgaagtta ttaaaatcgt tcgtgctctt    240
acaggccttg gtcttaaaga agcaaaagat gcagttgagc aaactccttc aactctaaaa    300
gagggtgtgg ctaaagctga agctgaggaa gctaaaaaac aacttgaaga agctggtgct    360
aaagtagaac ttaagtaa                                                  378

<210> SEQ ID NO 19
<211> LENGTH: 282
<212> TYPE: DNA
<213> ORGANISM: Campylobacter jejuni ATCC 33291

<400> SEQUENCE: 19
atggcagata ttactgatat aaagactata ctttacacag aaaaaagttt gaatttgcaa     60
gagcaaggtg tcgtagttat tcaaacttcg ccaaaaatga ctaaaacagg cttaaaagcg    120
gttttaaaag agtattttgg tgtaactcca aaaagcatca attccttaag aatggatgga    180
aaaattaagc gttttagagg tcgtttaggt caaagaaaca attacaaaaa attctatgtt    240
aagctacctg aaggtgttag cttagaaaat acggaggctt aa                       282

<210> SEQ ID NO 20
<211> LENGTH: 234
<212> TYPE: DNA
<213> ORGANISM: Campylobacter jejuni ATCC 33291

<400> SEQUENCE: 20
atggcggtta aattaaaaat caaaaaaggt gatagcgtta aggttatcac aggcgatgat     60
aaaggtaaaa caggtaaagt tttagcggta tatccaaaaa cacttaaagt ggtagttgaa    120
ggatgtaaaa tcgctaaaaa agctattaag ccgagtgaga aaaacccaaa tggtggtttt    180
atcaataaag aaatgccaat ggatatttcc aatgtggcaa aagttcagga gtaa          234

<210> SEQ ID NO 21
```

<211> LENGTH: 186
<212> TYPE: DNA
<213> ORGANISM: Campylobacter jejuni ATCC 33291

<400> SEQUENCE: 21

```
atggctaaaa aatcaatgat tgcaaaagcg gcacgcaagc ctaaatttaa ggttagagct    60
tatacaagat gccaaatttg tgggcgtccg cattcggttt atagagattt tggaatttgc   120
agagtttgct taagaaaaat gggcaatgaa ggtttgattc caggtcttaa gaaagcaagt   180
tggtaa                                                              186
```

<210> SEQ ID NO 22
<211> LENGTH: 357
<212> TYPE: DNA
<213> ORGANISM: Campylobacter jejuni ATCC 33291

<400> SEQUENCE: 22

```
atgagagcaa atgtattaaa aagaaaacta actttaagaa tcaaaagaaa aaaagaatt    60
agagcgaaaa tttcaggttg tgaaaatttt ccaagaattt ctgtatttaa atcaaacaga   120
actctatata tccaagcgat tgatgatgta aaagctgtaa ctttagcagc agttgatgga   180
cgcaaacttg gcgttaaagc aaataaagaa ggtgctaaaa aaatcgctgc tgaatttgct   240
aaaactttaa agttaaaaa gatagaacaa gctgttttg atagaaatgg ttatgtatat   300
catggtgtta tcgcagcatt ggctgaatct ttaagagaaa atggcattag gctataa     357
```

<210> SEQ ID NO 23
<211> LENGTH: 114
<212> TYPE: DNA
<213> ORGANISM: Campylobacter jejuni ATCC 33291

<400> SEQUENCE: 23

```
atgaaagtga gaccatcggt taaaaagatg tgcgacaaat gcaaagtagt tcgccgtaaa    60
ggcgtggttc gcattatttg cgaaaatcca aacataaac aaagacaagg ataa          114
```

<210> SEQ ID NO 24
<211> LENGTH: 393
<212> TYPE: DNA
<213> ORGANISM: Campylobacter jejuni ATCC 33291

<400> SEQUENCE: 24

```
atggcaaaaa gaaaaatcgt aagaaaaaaa gtagttaaaa aaaatatagc aaaaggtatt    60
gtttatatca gtgcgacttt taacaatact atggttacag taactgatga atgggaaat   120
gctatcgctt ggagtagtgc aggtggttta ggatttaaag gttctaaaaa atcaactcct   180
tatgcagcac aacaagcagt agaagacgct ttaaataaag caaagaaca cggaattaaa   240
gaagtaggca ttaaagtaca aggaccagga agcggtagag aaactgctgt taagagtgta   300
ggtgctatgg aaggaatcaa agtaactttc ttaaaagata tcactccatt agctcacaat   360
ggttgcagac cgcctaagcg tcgtcgtgtc taa                                393
```

<210> SEQ ID NO 25
<211> LENGTH: 147
<212> TYPE: DNA
<213> ORGANISM: Campylobacter jejuni ATCC 700819

<400> SEQUENCE: 25

```
atggcagtac caaagagaag agtgagcaaa actcgtgcag ctaaacgcag aactcactat    60
aaagttagtc ttcctatgcc tataaaagac aaagatggaa gctacaaaat gcctcaccgt   120
```

-continued gcgaatccaa caactaagga atattaa           147

<210> SEQ ID NO 26
<211> LENGTH: 378
<212> TYPE: DNA
<213> ORGANISM: Campylobacter jejuni ATCC 700819

<400> SEQUENCE: 26
atggcaatct ctaaagaaga tgtattagaa tatatttcaa atttaagtgt tcttgagtta      60
tcagaacttg taaaggaatt tgaagaaaaa tttggtgtgt ctgctgctcc tgtaatggta     120
gctggtggtg ctgtagctgg tggtgctgta gctgctgctg aagaaaaaac tgaatttgat     180
atcgttttaa ctgatggcgg tgctaaaaag attgaagtta ttaaaatcgt tcgtgctctt     240
acaggccttg gtcttaaaga agcaaaagat gcagttgagc aaactccttc aactctaaaa     300
gagggtgtgg ctaaagctga agctgaggaa gctaaaaaac aacttgaaga agctggtgct     360
aaagtagaac ttaagtaa                                                  378

<210> SEQ ID NO 27
<211> LENGTH: 282
<212> TYPE: DNA
<213> ORGANISM: Campylobacter jejuni ATCC 700819

<400> SEQUENCE: 27
atggcagata ttactgatat aaagactata cttacacag aaaaaagttt gaatttgcaa       60
gagcaaggtg tcgtagttat tcaaacttcg ccaaaaatga ctaaaacagg cttaaaagcg     120
gttttaaaag agtattttgg tgtaactcca aaaagcatca attccttaag aatggatgga     180
aaaattaagc gttttagagg tcgtttaggt caaagaaaca attacaaaaa attctatgtt     240
aagctacctg aaggtgttag cttagaaaat acggaggctt aa                       282

<210> SEQ ID NO 28
<211> LENGTH: 234
<212> TYPE: DNA
<213> ORGANISM: Campylobacter jejuni ATCC 700819

<400> SEQUENCE: 28
atggcggtta aattaaaaat caaaaaaggt gatagcgtta aggttatcac aggcgatgat      60
aaaggtaaaa caggtaaagt tttagcggta tatccaaaaa cacttaaagt ggtagttgaa     120
ggatgtaaaa tcgctaaaaa agctattaag ccgagtgaga aaacccaaa tggtggtttt      180 atcaataaag aaatgccaat ggatatttcc aatgtggcaa agttcagga gtaa            234

<210> SEQ ID NO 29
<211> LENGTH: 186
<212> TYPE: DNA
<213> ORGANISM: Campylobacter jejuni ATCC 700819

<400> SEQUENCE: 29
atggctaaaa aatcaatgat tgcaaaagcg gcacgcaagc ctaaatttaa ggttagagct      60
tatacaagat gccaaatttg tgggcgtccg cattcggttt atagagattt tggaatttgc     120
agagtttgct taagaaaaat gggcaatgaa ggtttgattc aggtcttaa gaaagcaagt      180 tggtaa                                                               186

<210> SEQ ID NO 30
<211> LENGTH: 357
<212> TYPE: DNA

<213> ORGANISM: Campylobacter jejuni ATCC 700819

<400> SEQUENCE: 30

```
atgagagcaa atgtattaaa aagaaaacta actttaagaa tcaaagaaa aaaagaatt      60
agagcgaaaa tttcaggttg tgaaaatttt ccaagaattt ctgtatttaa atcaaacaga   120
actctatata tccaagcgat tgatgatgta aaagctgtaa ctttagcagc agttgatgga   180
cgcaaacttg gcgttaaagc aaataaagaa ggtgctaaaa aatcgctgc tgaatttgct    240
aaaactttaa aagttaaaaa gatagaacaa gctgttttg atagaaatgg ttatgtatat    300
catggtgtta tcgcagcatt ggctgaatct ttaagagaaa atggcattag gctataa      357
```

<210> SEQ ID NO 31
<211> LENGTH: 114
<212> TYPE: DNA
<213> ORGANISM: Campylobacter jejuni ATCC 700819

<400> SEQUENCE: 31

```
atgaaagtga gaccatcggt taaaaagatg tgcgacaaat gcaaagtagt tcgccgtaaa    60
ggcgtggttc gcattatttg cgaaaatcca aacataaac aaagacaagg ataa          114
```

<210> SEQ ID NO 32
<211> LENGTH: 393
<212> TYPE: DNA
<213> ORGANISM: Campylobacter jejuni ATCC 700819

<400> SEQUENCE: 32

```
atggcaaaaa gaaaaatcgt aaagaaaaaa gtagttaaaa aaatatagc aaaggtatt      60
gtttatatca gtgcgacttt taacaatact atggttacag taactgatga atgggaaat   120
gctatcgctt ggagtagtgc aggtagttta ggatttaaag gttctaaaaa atcaactcct   180
tatgcagcac aacaagcagt agaagacgct ttaaataaag caaagaaaca cggaattaaa   240
gaagtaggca ttaaagtaca aggaccagga agcggtagaa aaactgctgt taaagtgta    300
ggcgctatgg aaggaatcaa agtaactttc ttaaaagata ttactccatt agctcacaat   360
ggttgcagac cgcctaagcg tcgtcgtgtc taa                                 393
```

<210> SEQ ID NO 33
<211> LENGTH: 147
<212> TYPE: DNA
<213> ORGANISM: Campylobacter jejuni doylei ATCC 49349T

<400> SEQUENCE: 33

```
atggcagtac caaagagaag agtaagtaaa actcgtgcag ctaaacgcag aactcactat    60
aaagttagtc ttcctatgcc tgtaaaagac aaagatggaa gctacaaaat gcctcaccgt   120
gcgaatccaa caactaagga atattaa                                        147
```

<210> SEQ ID NO 34
<211> LENGTH: 378
<212> TYPE: DNA
<213> ORGANISM: Campylobacter jejuni doylei ATCC 49349T

<400> SEQUENCE: 34

```
atggcaattt ctaagaagaga tgtattagaa tatatttcaa atttaagtgt tcttgagtta    60
tcagaacttg taaagaatt tgaagaaaaa tttggcgtgt ctgctgctcc tgtaatggta   120
gctggtggtg ctgcagctgg tggtgctgca gcagctgctg aagaaaaaac tgaatttgat   180
atcgttttaa ctgatggcgg tgctaaaaag attgaagtta ttaaaatcgt tcgtgctctt   240
```

```
acaggccttg gtcttaaaga agcaaaagat gcagttgagc aaactccttc aactctaaaa      300
gagggtgtag ctaaagctga agctgaggaa gctaaaaaac aacttgaaga agctggtgct      360
aaagtagaac ttaagtaa                                                   378

<210> SEQ ID NO 35
<211> LENGTH: 282
<212> TYPE: DNA
<213> ORGANISM: Campylobacter jejuni doylei ATCC 49349T

<400> SEQUENCE: 35
atggcagata ttactgatat aaagactata ctttacacag aaaaaagttt gaatttgcaa       60
gagcaaggtg tcgtagttat tcaaacttca ccaaagatga ctaaaacagg cttaaaagcg      120
gttttaaaag agtattttgg tgtaactcca aaaagcatca attctttaag aatggatgga      180
aaagttaagc gttttagagg tcgtttaggt caaagaaacg attataaaaa attctatgtt      240
aagctacctg aaggtgttag cttagaaaat gcggaggctt aa                         282

<210> SEQ ID NO 36
<211> LENGTH: 234
<212> TYPE: DNA
<213> ORGANISM: Campylobacter jejuni doylei ATCC 49349T

<400> SEQUENCE: 36
atggcggtta aattaaaaat caaaaaaggt gataacgtta aggttatcac aggcgatgat       60
aaaggtaaaa caggtaaagt tttagcggta tatccaaaaa cacttaaagt ggtagttgaa      120
ggatgtaaaa tcgctaaaaa agctattaag cctagcgaga aaaacccaaa tggtggtttt      180
atcaataaag aaatgccaat ggatatttcc aatgtggcaa aagttcagga gtaa            234

<210> SEQ ID NO 37
<211> LENGTH: 186
<212> TYPE: DNA
<213> ORGANISM: Campylobacter jejuni doylei ATCC 49349T

<400> SEQUENCE: 37
atggctaaaa aatcaatgat tgcaaaagcg gcacgcaagc ctaaatttaa agttagagct       60
tatacaagat gccaaatttg tgggcgtccg cattcggttt atagagattt tggaatttgc      120
agagtttgct taagaaaaat gggcaatgaa ggtttaattc aggtcttaa gaaagcaagt      180 tggtaa                                                                186

<210> SEQ ID NO 38
<211> LENGTH: 357
<212> TYPE: DNA
<213> ORGANISM: Campylobacter jejuni doylei ATCC 49349T

<400> SEQUENCE: 38
atgagagcaa atgtattaaa aagaaaacta actttaagaa tcaaaagaaa aaaaagaatt       60
agagcgaaaa tttcaggttg tgaaaatttt ccaagaattt ctgtatttaa atcgaacaga      120
actctatata tccaagcgat tgatgatgta aaagctgtaa ctttagcagc agttgatgga      180
cgcaaacttg gcgttaaagc aaataaagaa ggcgctaaaa aaatcgctgc tgaatttgct      240
aaaactttaa aagctaaaaa gatagaacaa gctgttttg atagaaatgg ttatgtatat      300
catggtgtta tcgcagcatt ggctgaatct ttaagagaaa atggcattag gctataa         357

<210> SEQ ID NO 39
```

```
<211> LENGTH: 114
<212> TYPE: DNA
<213> ORGANISM: Campylobacter jejuni doylei ATCC 49349T

<400> SEQUENCE: 39
atgaaagtga gaccatcggt taaaaagatg tgcgacaagt gcaaagtagt tcgccgtaaa      60
ggcgtggttc gcattatttg cgaaaatcca aacataaac aaagacaagg ataa            114

<210> SEQ ID NO 40
<211> LENGTH: 393
<212> TYPE: DNA
<213> ORGANISM: Campylobacter jejuni doylei ATCC 49349T

<400> SEQUENCE: 40
atggcaaaaa gaaaaatcgt aaagaaaaaa gtagttaaaa aaaatatagc aaaaggtatt      60
gtttatatca gtgcgacttt taacaatact atggttacag taactgatga atgggaaat     120 gctatcgctt ggagtagtgc aggtagttta ggatttaaag gttctaaaaa atcaactcct     180
tatgcagcac aacaagcagt agaagacgct ttaaataaag caaagaaaca cggaattaaa     240
gaagtaggca ttaaagtaca aggaccagga agcggtagag aaactgctgt taaagtgta     300 ggcgctatgg aaggaatcaa agtaacttc ttaaaagata ttactccatt agctcacaat     360
ggttgcagac cgcctaagcg tcgtcgtgtc taa                                  393

<210> SEQ ID NO 41
<211> LENGTH: 147
<212> TYPE: DNA
<213> ORGANISM: Campylobacter jejuni doylei ATCC 49350

<400> SEQUENCE: 41
atggcagtac caaagagaag agtgagcaaa actcgtgcag ctaaacgcag aactcactat      60
aaagttagtc ttcctatgcc tataaaagac aaagatggaa gctacaaaat gcctcaccgt    120
gcgaatctaa caactaagga atattaa                                         147

<210> SEQ ID NO 42
<211> LENGTH: 378
<212> TYPE: DNA
<213> ORGANISM: Campylobacter jejuni doylei ATCC 49350

<400> SEQUENCE: 42
atggcaattt ctaaagaaga tgtattagaa tatatttcaa atttaagtgt tcttgagtta      60
tcagaacttg taaagaatt tgaagaaaaa tttggcgtgt ctgctgctcc tgtaatggta    120
gctggtggtg ctgcagctgg tggtgctgca gcagctgctg aagaaaaaac tgaatttgat    180
atcgttttaa ctgatggcgg tgctaaaaag attgaagtta ttaaaatcgt tcgtgctctt    240
acaggccttg gtcttaaaga agcaaaagat gcagttgagc aaactccttc aactctaaaa    300
gagggtgtag ctaagctga gctgaggaa gctaaaaaac aacttgaaga agctggtgct    360
aaagtagaac ttaagtaa                                                   378

<210> SEQ ID NO 43
<211> LENGTH: 282
<212> TYPE: DNA
<213> ORGANISM: Campylobacter jejuni doylei ATCC 49350

<400> SEQUENCE: 43
atggcagata ttactgatat aaagactata ctttacacag aaaaaagttt gaatttgcaa      60
gagcaaggtg tcgtagttat tcaaacttca ccaaagatga ctaaaacagg cttaaaagcg    120
```

```
gttttaaaag agtatttgg tgtaactcca aaaagcatca attctttaag aatggatgga    180
aaagttaagc gttttagagg tcgtttaggt caaagaaacg attataaaaa attctatgtt    240
aagctacctg aaggtgttag cttagaaaat gcggaggctt aa                      282
```

<210> SEQ ID NO 44
<211> LENGTH: 234
<212> TYPE: DNA
<213> ORGANISM: Campylobacter jejuni doylei ATCC 49350

<400> SEQUENCE: 44

```
atggcggtta aattaaaaat caaaaaaggt gataacgtta aggttatcac aggcgatgat    60
aaaggtaaaa caggtaaagt tttagcggta tatccaaaaa cactcaaagt ggtagttgaa    120
ggatgtaaaa tcgctaaaaa agctattaag cctagcgaga aaaacccaaa tggtggtttt    180
attaataaag aaatgccaat ggatatttcc aatgtggcaa aagttcagga gtaa          234
```

<210> SEQ ID NO 45
<211> LENGTH: 186
<212> TYPE: DNA
<213> ORGANISM: Campylobacter jejuni doylei ATCC 49350

<400> SEQUENCE: 45

```
atggctaaaa aatcaatgat tgcaaaagcg gcacgcaagc ctaaatttaa agttagagct    60 tatcaagat gccaaatttg tgggcgtccg cattcggttt atagagattt tggaatttgc    120
agagtttgct taagaaaaat gggcaatgaa ggtttaattc caggtcttaa gaaagcaagt    180
tggtaa                                                              186
```

<210> SEQ ID NO 46
<211> LENGTH: 357
<212> TYPE: DNA
<213> ORGANISM: Campylobacter jejuni doylei ATCC 49350

<400> SEQUENCE: 46

```
atgagagcaa atgtattaaa aagaaaacta actttaagaa tcaaaagaaa aaaagaatt    60 agagcgaaaa tttcaggttg tgaaaatttt ccaagaattt ctgtatttaa atcgaacaga    120
actctatata tccaagcgat cgatgatgta aaagccgtaa cttttagcag cagttgatgga   180 cgcaaacttg gcgttaaagc aaataaagaa ggcgctaaaa aaatcgctgc tgaatttgct    240
aaaactttaa agctaaaaa gatagaacaa gctgtttttg atagaaatgg ttatgtatat    300
catggcgtta ttgcagtgtt agctgaatct ttaagagaaa atggcattag gctataa       357
```

<210> SEQ ID NO 47
<211> LENGTH: 114
<212> TYPE: DNA
<213> ORGANISM: Campylobacter jejuni doylei ATCC 49350

<400> SEQUENCE: 47

```
atgaaagtga gaccatcggt taaaaagatg tgcgacaagt gcaaagtagt tcgccgtaaa    60
ggcgtggttc gcattatttg cgaaaatcca aaacataaac aaagacaagg ataa          114
```

<210> SEQ ID NO 48
<211> LENGTH: 393
<212> TYPE: DNA
<213> ORGANISM: Campylobacter jejuni doylei ATCC 49350

<400> SEQUENCE: 48

| | |
|---|---|
| atggcaaaaa gaaaaatcgt aaagaaaaaa gtagttaaaa aaaatatagc aaaaggtatt | 60 |
| gtttatatca gtgcgacttt taacaatact atggttacag taactgatga atgggaaat | 120 |
| gctatcgctt ggagtagtgc aggtagttta ggatttaaag gttctaaaaa atcaactcct | 180 |
| tatgcagcac aacaagcagt agaagacgct ttaaataaag caaagaaca cggaattaaa | 240 |
| gaagtaggca ttaaagtaca aggaccagga agcggtagag aaactgctgt taaaagtgta | 300 |
| ggcgctatgg aaggaatcaa agtaactttc ttaaaagata ttactccatt agctcacaat | 360 |
| ggttgcagac cgcctaagcg tcgtcgtgtc taa | 393 |

<210> SEQ ID NO 49
<211> LENGTH: 147
<212> TYPE: DNA
<213> ORGANISM: Campylobacter coli

<400> SEQUENCE: 49

| | |
|---|---|
| atggcagtac ctaagagaag agtgagtaaa actcgtgcag caaaacgcag aactcactat | 60 |
| aaagtaagtc ttcctatgcc tataaaagac aaagatggaa gctacaaaat gcctcatcgt | 120 |
| gcaaatccaa atactaagga atactaa | 147 |

<210> SEQ ID NO 50
<211> LENGTH: 378
<212> TYPE: DNA
<213> ORGANISM: Campylobacter coli

<400> SEQUENCE: 50

| | |
|---|---|
| atggcaattt ctaaagaaga gtgtattagaa tttatttcaa atttaagtgt tcttgagctt | 60 |
| tctgagcttg taaaagaatt tgaagaaaaa tttggtgtat ctgctgctcc tgtaatggta | 120 |
| gcaggtggtg cagcagcagg tggtgcagca gctgcagctg aagaaaaaac tgaatttgat | 180 |
| atcgttttag ttgatggtgg tgctaaaaag atcgaagtaa ttaaaatcgt tcgtgcttta | 240 |
| actggtcttg gacttaaaga agcaaaagat gcagtagagc aaacaccttc aaccttaaaa | 300 |
| gaaggcgtgg ctaaagctga tgcagaagaa gctaaaaaac aacttgaaga agctggtgct | 360 |
| aaagtagaac ttaagtaa | 378 |

<210> SEQ ID NO 51
<211> LENGTH: 282
<212> TYPE: DNA
<213> ORGANISM: Campylobacter coli

<400> SEQUENCE: 51

| | |
|---|---|
| atggcagata ttactgatat aaagactata cttacacag aaaaaagttt gaatttgcaa | 60 |
| gagcaaggtg tcgtagttat tcaaacttcg ccaaaaatga ctaaaacagg cttaaaagcg | 120 |
| gttttaaaag agtattttgg tgtaactcca aaaagcatca attctttaag aatggatgga | 180 |
| aaagttaagc gttttagagg tcgtttaggt caaagaaacg attataaaaa attctatgtt | 240 |
| aagctacctg aaggtgttag cttagaaaat gcggaggctt aa | 282 |

<210> SEQ ID NO 52
<211> LENGTH: 234
<212> TYPE: DNA
<213> ORGANISM: Campylobacter coli

<400> SEQUENCE: 52

| | |
|---|---|
| atggcggtta aattaaaaat caaaaaaggt gatagcgtta aggttatcac aggcgatgat | 60 |
| aaaggtaaaa caggtaaagt tttagcggta tatccaaaaa cacttaaagt ggtagttgaa | 120 |

```
ggatgtaaaa tcgctaaaaa agctattaag ccgagtgaga aaaacccaaa tggtggtttt      180
atcaataaag aaatgccaat ggatatttcc aatgtggcaa agttcagga gtaa            234

<210> SEQ ID NO 53
<211> LENGTH: 186
<212> TYPE: DNA
<213> ORGANISM: Campylobacter coli

<400> SEQUENCE: 53
atggctaaaa aatcaatgat tgcaaaagcg gcacgcaaac ctaaattcaa agtaagaggc      60
tatacaagat gccaaatttg tgggcgtccg cattcggttt atagagattt tggaatttgt     120
agagtttgcc taagaaaaat gggtaatgaa ggcttgattc caggtcttaa aaaagcaagc     180
tggtaa                                                                186

<210> SEQ ID NO 54
<211> LENGTH: 357
<212> TYPE: DNA
<213> ORGANISM: Campylobacter coli

<400> SEQUENCE: 54
atgagagcaa atgtactaaa aagaaaacta actttaagaa ttaaaagaaa aaaaagaatt      60
agagcaaaaa tttcaggatg tgaaaacttc ccaagaattt ctgttttta atcaaataga     120 actctttata tccaagcgat tgatgatgtt aaagctgtaa ctttagcagc agtagatgga     180
cgcaaacttg gcgttaaagc aaacaaagaa ggtgctaaaa aatcgctac tgaatttgct     240 aaagttttaa agctaagca aatagaacaa gctgtgtttg atagaaatgg ttatgtatat     300
cacggagtaa ttgcagcatt agctgaatct ttaagagaaa atggtattag gctataa       357

<210> SEQ ID NO 55
<211> LENGTH: 114
<212> TYPE: DNA
<213> ORGANISM: Campylobacter coli

<400> SEQUENCE: 55
atgaaagtga gaccatcagt taaaaagatg tgcgacaagt gcaaagtagt tcgccgtaaa      60
ggcgtagttc gcattatttg cgaaaatcca aaacataaac aaagacaagg ataa           114

<210> SEQ ID NO 56
<211> LENGTH: 393
<212> TYPE: DNA
<213> ORGANISM: Campylobacter coli

<400> SEQUENCE: 56
atggcaaaaa gaaaaatcgt aaagaaaaaa gtagttaaaa aaaatatagc aaaaggtatt      60
gtttatatca gtgcaacttt taacaatacc atggtaactg ttacagatga atgggaaat     120 gctatcgctt ggagcagtgc aggcggttta ggatttaaag gttctaaaaa atcaactcct     180
tatgcagcac aacaagcagt agaagacgct ttaaataaag caaagaaca cggaatcaaa     240 gaagtaggca ttaaagtaca aggaccagga agcggtagag aaactgctgt taaaagtgta     300
ggtgctatgg aaggaatcaa agtaactttc ttaaagata ttactccatt agctcataat     360
ggttgcagac cgcctaagcg tcgtcgtgtc taa                                  393

<210> SEQ ID NO 57
<211> LENGTH: 147
<212> TYPE: DNA
```

<213> ORGANISM: Campylobacter lari

<400> SEQUENCE: 57

| atggcagtac | ctaagagaag | agtgagcaaa | actcgtgcag | caaaacgcag | aactcattat | 60 |
| aaagttaccc | tacctatgcc | tataaaagac | aaagatggta | gctataaaat | gcctcaccgt | 120 |
| gtaaatccag | taactaagga | atattaa | | | | 147 |

<210> SEQ ID NO 58
<211> LENGTH: 378
<212> TYPE: DNA
<213> ORGANISM: Campylobacter lari

<400> SEQUENCE: 58

| atggcaatta | ctaaagaaga | tgtattagaa | tttatttcta | acctaagtgt | tcttgagctt | 60 |
| tcagaattag | taaaagaatt | tgaagaaaaa | tttggtgttt | ctgctgctcc | agttatggtt | 120 |
| gcaggtgctg | ctgttgcagg | tgctgctggc | ggtgctgctg | aggaaaaaac | tgaatttgat | 180 |
| attgtattac | aagatggtgg | tgataaaaaa | atcaacgtaa | ttaaagttgt | tcgtgcatta | 240 |
| actggtcttg | gattaaaaga | agcaaaagac | gcagttgagc | aaactccatc | agttcttaaa | 300 |
| gaaggtgtta | gcaaagctga | agctgaagaa | gctaaaaagc | aacttgaaga | agctggcgct | 360 |
| aaggttgagc | ttaaataa | | | | | 378 |

<210> SEQ ID NO 59
<211> LENGTH: 282
<212> TYPE: DNA
<213> ORGANISM: Campylobacter lari

<400> SEQUENCE: 59

| atggcagata | ttactgatat | aaaaacaata | ctttacactg | aaaaaagtct | aaaccttcaa | 60 |
| gagcaaggtg | ttgtagtaat | tcaaacatca | ccaaaaatga | ctaaaaatgg | tctaaaagaa | 120 |
| gtattaagag | aatattttgg | tgtaactcca | gtaagaatta | ttctttaaa | aatggatgga | 180 |
| aaaataaagc | gttttagagg | tcgtgaaggt | caaagaaata | gctttaaaaa | attctatgtt | 240 |
| aagctaccag | aaggtgttag | cttagaaagt | tcggaggcat | aa | | 282 |

<210> SEQ ID NO 60
<211> LENGTH: 228
<212> TYPE: DNA
<213> ORGANISM: Campylobacter lari

<400> SEQUENCE: 60

| atgaaattaa | aaatcaaaaa | aaatgatatg | gtaaaagtta | tcgcaggtga | tgacaaaggt | 60 |
| aaaacaggta | agttttagc | agttttcct | aaaacaaata | aagtaattgt | tgagggttgt | 120 |
| aaaattgcta | aaaaagctgt | aaaaccaagt | gataaaaatc | caaatggtgg | ttttgtaaat | 180 |
| aaagaaatgc | caatggatat | ttcaaatgta | gcaaaggcag | gtgagtaa | | 228 |

<210> SEQ ID NO 61
<211> LENGTH: 186
<212> TYPE: DNA
<213> ORGANISM: Campylobacter lari

<400> SEQUENCE: 61

| atggctaaaa | aatcaatgat | tgcaaaagct | gcccgcaaac | ctaaatttag | cgttagaggg | 60 |
| tatactagat | gccaaatttg | tggaagacca | cattcagttt | atagagattt | tggaatttgt | 120 |
| agagtttgct | taagaaaaat | ggcaaatgag | ggtttaattc | ctggtcttaa | aaaagcaagt | 180 | tggtaa                                                                    186

<210> SEQ ID NO 62
<211> LENGTH: 357
<212> TYPE: DNA
<213> ORGANISM: Campylobacter lari

<400> SEQUENCE: 62
atgagagcaa atgtattaaa aagaaaatta tctttaagaa ttaaaagaaa aaaaagaatt      60
agagcaaaaa tttcaggaac acaagctctt ccaagaatct ctgttttaa atcaaacaga      120 actttatata tccaagctat tgatgatgtt aaagcagtta ctttagcagc tgttgatggt      180
agaaaaattg gtgtaaaagc aaataaagaa ggtgctaaaa aaatagcagc tgaatttgca      240
aaagctttaa aagcaaaaaa tattgaagaa gcagtgtttg atagaaatgg ttatttatac      300
catggtgtga ttgcggtttt agctgaagca ctaagagaaa atggaatcaa actataa        357

<210> SEQ ID NO 63
<211> LENGTH: 114
<212> TYPE: DNA
<213> ORGANISM: Campylobacter lari

<400> SEQUENCE: 63
atgaaagtta gaccatctgt taaaaagatg tgtgacaagt gcaaagtagt tcgccgtaaa      60
ggcgtagttc gcattatttg cgaaaatcca aacacaaac aaagacaagg ataa            114

<210> SEQ ID NO 64
<211> LENGTH: 393
<212> TYPE: DNA
<213> ORGANISM: Campylobacter lari

<400> SEQUENCE: 64
atggcaaaaa gaaaagtagt taagaaaaaa gtagttaaga aaatattgc aaaaggtata      60 gtttatatca gcgcaacatt taacaatact atggtaacag ttacagatga atgggaaat      120 gctatagctt ggagtagtgc aggtggttta ggatttaaag gttctaaaaa atcaactcct      180
tatgcagcac aacaagcagt tgaagatgct ttaaacaaag caaagaaca tggcattaaa      240 gaagtaggga ttaaagttca aggaccagga agtggtcgtg agacagcggt aaaaagtgta      300
ggtgctatgg aagtattaa agtaactttc ttaaagata taactccatt agctcataat      360
ggttgtagac caccaaaacg tcgtcgtgtc taa                                  393

<210> SEQ ID NO 65
<211> LENGTH: 48
<212> TYPE: PRT
<213> ORGANISM: Campylobacter jejuni ATCC 33560T

<400> SEQUENCE: 65

Met Ala Val Pro Lys Arg Arg Val Ser Lys Thr Arg Ala Ala Lys Arg
1               5                   10                  15

Arg Thr His Tyr Lys Val Ser Leu Pro Met Pro Val Lys Asp Lys Asp
                20                  25                  30

Gly Ser Tyr Lys Met Pro His Arg Ala Asn Pro Thr Thr Lys Glu Tyr
        35                  40                  45

<210> SEQ ID NO 66
<211> LENGTH: 125
<212> TYPE: PRT
<213> ORGANISM: Campylobacter jejuni ATCC 33560T

<400> SEQUENCE: 66

Met Ala Ile Ser Lys Glu Asp Val Leu Glu Tyr Ile Ser Asn Leu Ser
1               5                   10                  15

Val Leu Glu Leu Ser Glu Leu Val Lys Glu Phe Glu Glu Lys Phe Gly
            20                  25                  30

Val Ser Ala Ala Pro Val Met Val Ala Gly Ala Ala Ala Gly Gly
        35                  40                  45

Ala Ala Ala Ala Glu Glu Lys Thr Glu Phe Asp Ile Val Leu Thr
    50                  55                  60

Asp Gly Gly Ala Lys Lys Ile Glu Val Ile Lys Ile Val Arg Ala Leu
65                  70                  75                  80

Thr Gly Leu Gly Leu Lys Glu Ala Lys Asp Ala Val Glu Gln Thr Pro
                85                  90                  95

Ser Thr Leu Lys Glu Gly Val Ala Lys Ala Glu Ala Glu Glu Ala Lys
            100                 105                 110

Lys Gln Leu Glu Glu Ala Gly Ala Lys Val Glu Leu Lys
        115                 120                 125

<210> SEQ ID NO 67
<211> LENGTH: 93
<212> TYPE: PRT
<213> ORGANISM: Campylobacter jejuni ATCC 33560T

<400> SEQUENCE: 67

Met Ala Asp Ile Thr Asp Ile Lys Thr Ile Leu Tyr Thr Glu Lys Ser
1               5                   10                  15

Leu Asn Leu Gln Glu Gln Gly Val Val Val Ile Gln Thr Ser Pro Lys
            20                  25                  30

Met Thr Lys Thr Gly Leu Lys Ala Val Leu Lys Glu Tyr Phe Gly Val
        35                  40                  45

Thr Pro Lys Ser Ile Asn Ser Leu Arg Met Asp Gly Lys Val Lys Arg
    50                  55                  60

Phe Arg Gly Arg Leu Gly Gln Arg Asn Asp Tyr Lys Lys Phe Tyr Val
65                  70                  75                  80

Lys Leu Pro Glu Gly Val Ser Leu Glu Asn Thr Glu Ala
                85                  90

<210> SEQ ID NO 68
<211> LENGTH: 77
<212> TYPE: PRT
<213> ORGANISM: Campylobacter jejuni ATCC 33560T

<400> SEQUENCE: 68

Met Ala Val Lys Leu Lys Ile Lys Lys Gly Asp Ser Val Lys Val Ile
1               5                   10                  15

Thr Gly Asp Asp Lys Gly Lys Thr Gly Lys Val Leu Ala Val Tyr Pro
            20                  25                  30

Lys Thr Leu Lys Val Val Val Glu Gly Cys Lys Ile Ala Lys Lys Ala
        35                  40                  45

Ile Lys Pro Ser Glu Lys Asn Pro Asn Gly Gly Phe Ile Asn Lys Glu
    50                  55                  60

Met Pro Met Asp Ile Ser Asn Val Ala Lys Val Gln Glu
65                  70                  75

<210> SEQ ID NO 69
<211> LENGTH: 61

```
<212> TYPE: PRT
<213> ORGANISM: Campylobacter jejuni ATCC 33560T

<400> SEQUENCE: 69

Met Ala Lys Lys Ser Met Ile Ala Lys Ala Arg Lys Pro Lys Phe
1               5                   10                  15

Lys Val Arg Ala Tyr Thr Arg Cys Gln Ile Cys Gly Arg Pro His Ser
            20                  25                  30

Val Tyr Arg Asp Phe Gly Ile Cys Arg Val Cys Leu Arg Lys Met Gly
        35                  40                  45

Asn Glu Gly Leu Ile Pro Gly Leu Lys Lys Ala Ser Trp
    50                  55                  60

<210> SEQ ID NO 70
<211> LENGTH: 118
<212> TYPE: PRT
<213> ORGANISM: Campylobacter jejuni ATCC 33560T

<400> SEQUENCE: 70

Met Arg Ala Asn Val Leu Lys Arg Lys Leu Thr Leu Arg Ile Lys Arg
1               5                   10                  15

Lys Lys Arg Ile Arg Ala Lys Ile Ser Gly Cys Glu Asn Phe Pro Arg
            20                  25                  30

Ile Ser Val Phe Lys Ser Asn Arg Thr Leu Tyr Ile Gln Ala Ile Asp
        35                  40                  45

Asp Val Lys Ala Val Thr Leu Ala Ala Val Asp Gly Arg Lys Leu Gly
    50                  55                  60

Val Lys Ala Asn Lys Glu Gly Ala Lys Lys Ile Ala Ala Glu Phe Ala
65                  70                  75                  80

Lys Thr Leu Lys Ala Lys Lys Ile Glu Gln Ala Val Phe Asp Arg Asn
                85                  90                  95

Gly Tyr Val Tyr His Gly Val Ile Ala Ala Leu Ala Glu Ser Leu Arg
            100                 105                 110

Glu Asn Gly Ile Arg Leu
        115

<210> SEQ ID NO 71
<211> LENGTH: 37
<212> TYPE: PRT
<213> ORGANISM: Campylobacter jejuni ATCC 33560T

<400> SEQUENCE: 71

Met Lys Val Arg Pro Ser Val Lys Met Cys Asp Lys Cys Lys Val
1               5                   10                  15

Val Arg Arg Lys Gly Val Val Arg Ile Ile Cys Glu Asn Pro Lys His
            20                  25                  30

Lys Gln Arg Gln Gly
        35

<210> SEQ ID NO 72
<211> LENGTH: 130
<212> TYPE: PRT
<213> ORGANISM: Campylobacter jejuni ATCC_1 33560T

<400> SEQUENCE: 72

Met Ala Lys Arg Lys Ile Val Lys Lys Val Val Lys Asn Ile
1               5                   10                  15

Ala Lys Gly Ile Val Tyr Ile Ser Ala Thr Phe Asn Asn Thr Met Val
            20                  25                  30
```

```
Thr Val Thr Asp Glu Met Gly Asn Ala Ile Ala Trp Ser Ser Ala Gly
         35                  40                  45

Gly Leu Gly Phe Lys Gly Ser Lys Lys Ser Thr Pro Tyr Ala Ala Gln
     50                  55                  60

Gln Ala Val Glu Asp Ala Leu Asn Lys Ala Lys Glu His Gly Ile Lys
 65                  70                  75                  80

Glu Val Gly Ile Lys Val Gln Gly Pro Gly Ser Gly Arg Glu Thr Ala
                 85                  90                  95

Val Lys Ser Val Gly Ala Met Glu Gly Ile Lys Val Thr Phe Leu Lys
             100                 105                 110

Asp Ile Thr Pro Leu Ala His Asn Gly Cys Arg Pro Pro Lys Arg Arg
         115                 120                 125

Arg Val
    130

<210> SEQ ID NO 73
<211> LENGTH: 48
<212> TYPE: PRT
<213> ORGANISM: Campylobacter jejuni ATCC 29248=JCM 2013

<400> SEQUENCE: 73

Met Ala Val Pro Lys Arg Arg Val Ser Lys Thr Arg Ala Ala Lys Arg
1               5                   10                  15

Arg Thr His Tyr Lys Val Ser Leu Pro Met Pro Ile Lys Asp Lys Asp
            20                  25                  30

Gly Ser Tyr Lys Met Pro His Arg Ala Asn Pro Thr Thr Lys Glu Tyr
        35                  40                  45

<210> SEQ ID NO 74
<211> LENGTH: 125
<212> TYPE: PRT
<213> ORGANISM: Campylobacter jejuni ATCC 29248=JCM 2013

<400> SEQUENCE: 74

Met Ala Ile Ser Lys Glu Asp Val Leu Glu Tyr Ile Ser Asn Leu Ser
1               5                   10                  15

Val Leu Glu Leu Ser Glu Leu Val Lys Glu Phe Glu Lys Phe Gly
            20                  25                  30

Val Ser Ala Ala Pro Val Met Val Ala Gly Gly Ala Ala Gly Gly
         35                  40                  45

Ala Ala Ala Ala Ala Glu Glu Lys Thr Glu Phe Asp Ile Val Leu Thr
 50                  55                  60

Asp Gly Gly Ala Lys Lys Ile Glu Val Ile Lys Ile Val Arg Ala Leu
 65                  70                  75                  80

Thr Gly Leu Gly Leu Lys Glu Ala Lys Asp Ala Val Glu Gln Thr Pro
             85                  90                  95

Ser Thr Leu Lys Glu Gly Val Ala Lys Ala Glu Ala Glu Ala Lys
            100                 105                 110

Lys Gln Leu Glu Glu Ala Gly Ala Lys Val Glu Leu Lys
        115                 120                 125

<210> SEQ ID NO 75
<211> LENGTH: 93
<212> TYPE: PRT
<213> ORGANISM: Campylobacter jejuni ATCC 29248=JCM 2013

<400> SEQUENCE: 75
```

```
Met Ala Asp Ile Thr Asp Ile Lys Thr Ile Leu Tyr Thr Glu Lys Ser
1               5                   10                  15

Leu Asn Leu Gln Glu Gln Gly Val Val Ile Gln Thr Ser Pro Lys
            20                  25                  30

Met Thr Lys Thr Gly Leu Lys Val Val Leu Lys Glu Tyr Phe Gly Val
                35                  40                  45

Thr Pro Lys Ser Ile Asn Ser Leu Arg Met Asp Gly Lys Ile Lys Arg
        50                  55                  60

Phe Arg Gly Arg Leu Gly Gln Arg Asn Asn Tyr Lys Lys Phe Tyr Val
65                  70                  75                  80

Lys Leu Pro Glu Gly Val Ser Leu Glu Asn Thr Glu Ala
                85                  90
```

<210> SEQ ID NO 76
<211> LENGTH: 77
<212> TYPE: PRT
<213> ORGANISM: Campylobacter jejuni ATCC 29248=JCM 2013

<400> SEQUENCE: 76

```
Met Ala Val Lys Leu Lys Ile Lys Lys Gly Asp Ser Val Lys Val Ile
1               5                   10                  15

Thr Gly Asp Asp Lys Gly Lys Thr Gly Lys Val Leu Ala Val Tyr Pro
            20                  25                  30

Lys Thr Leu Lys Val Val Glu Gly Cys Lys Ile Ala Lys Lys Ala
                35                  40                  45

Ile Lys Pro Ser Glu Lys Asn Pro Asn Gly Gly Phe Ile Asn Lys Glu
        50                  55                  60

Met Pro Met Asp Ile Ser Asn Val Ala Lys Val Gln Glu
65                  70                  75
```

<210> SEQ ID NO 77
<211> LENGTH: 61
<212> TYPE: PRT
<213> ORGANISM: Campylobacter jejuni ATCC 29248=JCM 2013

<400> SEQUENCE: 77

```
Met Ala Lys Lys Ser Met Ile Ala Lys Ala Arg Lys Pro Lys Phe
1               5                   10                  15

Lys Val Arg Ala Tyr Thr Arg Cys Gln Ile Cys Gly Arg Pro His Ser
            20                  25                  30

Val Tyr Arg Asp Phe Gly Ile Cys Arg Val Cys Leu Arg Lys Met Gly
        35                  40                  45

Asn Glu Gly Leu Ile Pro Gly Leu Lys Lys Ala Ser Trp
        50                  55                  60
```

<210> SEQ ID NO 78
<211> LENGTH: 118
<212> TYPE: PRT
<213> ORGANISM: Campylobacter jejuni ATCC 29248=JCM 2013

<400> SEQUENCE: 78

```
Met Arg Ala Asn Val Leu Lys Arg Lys Leu Thr Leu Arg Ile Lys Arg
1               5                   10                  15

Lys Lys Arg Ile Arg Ala Lys Ile Ser Gly Cys Glu Asn Phe Pro Arg
            20                  25                  30

Ile Ser Val Phe Lys Ser Asn Arg Thr Leu Tyr Ile Gln Ala Ile Asp
        35                  40                  45

Asp Val Lys Ala Val Thr Leu Ala Ala Val Asp Gly Arg Lys Leu Gly
```

```
                    50                  55                  60
Val Lys Ala Asn Lys Glu Gly Ala Lys Ile Ala Ala Glu Phe Ala
 65                  70                  75                  80

Lys Thr Leu Lys Ala Lys Ile Glu Gln Ala Val Phe Asp Arg Asn
                 85                  90                  95

Gly Tyr Val Tyr His Gly Val Ile Ala Leu Ala Glu Ser Leu Arg
            100                 105                 110

Glu Asn Gly Ile Arg Leu
            115

<210> SEQ ID NO 79
<211> LENGTH: 37
<212> TYPE: PRT
<213> ORGANISM: Campylobacter jejuni ATCC 29248=JCM 2013

<400> SEQUENCE: 79

Met Lys Val Arg Pro Ser Val Lys Lys Met Cys Asp Lys Cys Lys Val
 1               5                  10                  15

Val Arg Arg Lys Gly Val Val Arg Ile Ile Cys Glu Asn Pro Lys His
                 20                  25                  30

Lys Gln Arg Gln Gly
            35

<210> SEQ ID NO 80
<211> LENGTH: 130
<212> TYPE: PRT
<213> ORGANISM: Campylobacter jejuni ATCC_1 29428

<400> SEQUENCE: 80

Met Ala Lys Arg Lys Ile Val Lys Lys Val Val Lys Lys Asn Ile
 1               5                  10                  15

Ala Lys Gly Ile Val Tyr Ile Ser Ala Thr Phe Asn Asn Thr Met Val
                 20                  25                  30

Thr Val Thr Asp Glu Met Gly Asn Ala Ile Ala Trp Ser Ser Ala Gly
            35                  40                  45

Gly Leu Gly Phe Lys Gly Ser Lys Lys Ser Thr Pro Tyr Ala Ala Gln
 50                  55                  60

Gln Ala Val Glu Asp Ala Leu Asn Lys Ala Lys Glu His Gly Ile Lys
 65                  70                  75                  80

Glu Val Gly Ile Lys Val Gln Gly Pro Gly Ser Gly Arg Glu Thr Ala
                 85                  90                  95

Val Lys Ser Val Gly Ala Met Glu Gly Ile Lys Val Thr Phe Leu Lys
            100                 105                 110

Asp Ile Thr Pro Leu Ala His Asn Gly Cys Arg Pro Pro Lys Arg Arg
            115                 120                 125

Arg Val
    130

<210> SEQ ID NO 81
<211> LENGTH: 48
<212> TYPE: PRT
<213> ORGANISM: Campylobacter jejuni ATCC 33291

<400> SEQUENCE: 81

Met Ala Val Pro Lys Arg Arg Val Ser Lys Thr Arg Ala Ala Lys Arg
 1               5                  10                  15

Arg Thr His Tyr Lys Val Ser Leu Pro Met Pro Ile Lys Asp Lys Asp
                 20                  25                  30
```

-continued

Gly Ser Tyr Lys Met Pro His Arg Ala Asn Pro Thr Thr Lys Glu Tyr
            35                  40                  45

<210> SEQ ID NO 82
<211> LENGTH: 125
<212> TYPE: PRT
<213> ORGANISM: Campylobacter jejuni ATCC 33291

<400> SEQUENCE: 82

Met Ala Ile Ser Lys Glu Asp Val Leu Glu Tyr Ile Ser Asn Leu Ser
1               5                   10                  15

Val Leu Glu Leu Ser Glu Leu Val Lys Glu Phe Glu Glu Lys Phe Gly
            20                  25                  30

Val Ser Ala Ala Pro Val Met Ile Ala Gly Ala Ala Gly Gly
        35                  40                  45

Ala Ala Ala Ala Glu Glu Lys Thr Glu Phe Asp Ile Val Leu Thr
    50                  55                  60

Asp Gly Gly Ala Lys Lys Ile Glu Val Ile Lys Ile Val Arg Ala Leu
65                  70                  75                  80

Thr Gly Leu Gly Leu Lys Glu Ala Lys Asp Ala Val Glu Gln Thr Pro
                85                  90                  95

Ser Thr Leu Lys Glu Gly Val Ala Lys Ala Glu Ala Glu Ala Lys
            100                 105                 110

Lys Gln Leu Glu Glu Ala Gly Ala Lys Val Glu Leu Lys
        115                 120                 125

<210> SEQ ID NO 83
<211> LENGTH: 93
<212> TYPE: PRT
<213> ORGANISM: Campylobacter jejuni ATCC 33291

<400> SEQUENCE: 83

Met Ala Asp Ile Thr Asp Ile Lys Thr Ile Leu Tyr Thr Glu Lys Ser
1               5                   10                  15

Leu Asn Leu Gln Glu Gln Gly Val Val Val Ile Gln Thr Ser Pro Lys
            20                  25                  30

Met Thr Lys Thr Gly Leu Lys Ala Val Leu Lys Glu Tyr Phe Gly Val
        35                  40                  45

Thr Pro Lys Ser Ile Asn Ser Leu Arg Met Asp Gly Lys Ile Lys Arg
    50                  55                  60

Phe Arg Gly Arg Leu Gly Gln Arg Asn Asn Tyr Lys Lys Phe Tyr Val
65                  70                  75                  80

Lys Leu Pro Glu Gly Val Ser Leu Glu Asn Thr Glu Ala
                85                  90

<210> SEQ ID NO 84
<211> LENGTH: 77
<212> TYPE: PRT
<213> ORGANISM: Campylobacter jejuni ATCC 33291

<400> SEQUENCE: 84

Met Ala Val Lys Leu Lys Ile Lys Lys Gly Asp Ser Val Lys Val Ile
1               5                   10                  15

Thr Gly Asp Asp Lys Gly Lys Thr Gly Lys Val Leu Ala Val Tyr Pro
            20                  25                  30

Lys Thr Leu Lys Val Val Glu Gly Cys Lys Ile Ala Lys Lys Ala
        35                  40                  45

Ile Lys Pro Ser Glu Lys Asn Pro Asn Gly Gly Phe Ile Asn Lys Glu
    50                  55                  60

Met Pro Met Asp Ile Ser Asn Val Ala Lys Val Gln Glu
65                  70                  75

<210> SEQ ID NO 85
<211> LENGTH: 61
<212> TYPE: PRT
<213> ORGANISM: Campylobacter jejuniATCC 33291

<400> SEQUENCE: 85

Met Ala Lys Lys Ser Met Ile Ala Lys Ala Ala Arg Lys Pro Lys Phe
1               5                   10                  15

Lys Val Arg Ala Tyr Thr Arg Cys Gln Ile Cys Gly Arg Pro His Ser
                20                  25                  30

Val Tyr Arg Asp Phe Gly Ile Cys Arg Val Cys Leu Arg Lys Met Gly
            35                  40                  45

Asn Glu Gly Leu Ile Pro Gly Leu Lys Lys Ala Ser Trp
        50                  55                  60

<210> SEQ ID NO 86
<211> LENGTH: 118
<212> TYPE: PRT
<213> ORGANISM: Campylobacter jejuni ATCC 33291

<400> SEQUENCE: 86

Met Arg Ala Asn Val Leu Lys Arg Lys Leu Thr Leu Arg Ile Lys Arg
1               5                   10                  15

Lys Lys Arg Ile Arg Ala Lys Ile Ser Gly Cys Glu Asn Phe Pro Arg
                20                  25                  30

Ile Ser Val Phe Lys Ser Asn Arg Thr Leu Tyr Ile Gln Ala Ile Asp
            35                  40                  45

Asp Val Lys Ala Val Thr Leu Ala Ala Val Asp Gly Arg Lys Leu Gly
        50                  55                  60

Val Lys Ala Asn Lys Glu Gly Ala Lys Lys Ile Ala Ala Glu Phe Ala
65                  70                  75                  80

Lys Thr Leu Lys Val Lys Lys Ile Glu Gln Ala Val Phe Asp Arg Asn
                85                  90                  95

Gly Tyr Val Tyr His Gly Val Ile Ala Ala Leu Ala Glu Ser Leu Arg
            100                 105                 110

Glu Asn Gly Ile Arg Leu
        115

<210> SEQ ID NO 87
<211> LENGTH: 37
<212> TYPE: PRT
<213> ORGANISM: Campylobacter jejuni

<400> SEQUENCE: 87

Met Lys Val Arg Pro Ser Val Lys Met Cys Asp Lys Cys Lys Val
1               5                   10                  15

Val Arg Arg Lys Gly Val Val Arg Ile Ile Cys Glu Asn Pro Lys His
                20                  25                  30

Lys Gln Arg Gln Gly
        35

<210> SEQ ID NO 88
<211> LENGTH: 130
<212> TYPE: PRT

<213> ORGANISM: Campylobacter jejuni ATCC_1 33291

<400> SEQUENCE: 88

Met Ala Lys Arg Lys Ile Val Lys Lys Val Val Lys Asn Ile
1               5                   10                  15

Ala Lys Gly Ile Val Tyr Ile Ser Ala Thr Phe Asn Asn Thr Met Val
            20                  25                  30

Thr Val Thr Asp Glu Met Gly Asn Ala Ile Ala Trp Ser Ser Ala Gly
        35                  40                  45

Gly Leu Gly Phe Lys Gly Ser Lys Ser Thr Pro Tyr Ala Ala Gln
    50                  55                  60

Gln Ala Val Glu Asp Ala Leu Asn Lys Ala Lys Glu His Gly Ile Lys
65                  70                  75                  80

Glu Val Gly Ile Lys Val Gln Gly Pro Gly Ser Gly Arg Glu Thr Ala
                85                  90                  95

Val Lys Ser Val Gly Ala Met Glu Gly Ile Lys Val Thr Phe Leu Lys
            100                 105                 110

Asp Ile Thr Pro Leu Ala His Asn Gly Cys Arg Pro Lys Arg Arg
        115                 120                 125

Arg Val
    130

<210> SEQ ID NO 89
<211> LENGTH: 48
<212> TYPE: PRT
<213> ORGANISM: Campylobacter jejuni ATCC 700819

<400> SEQUENCE: 89

Met Ala Val Pro Lys Arg Arg Val Ser Lys Thr Arg Ala Ala Lys Arg
1               5                   10                  15

Arg Thr His Tyr Lys Val Ser Leu Pro Met Pro Ile Lys Asp Lys Asp
            20                  25                  30

Gly Ser Tyr Lys Met Pro His Arg Ala Asn Pro Thr Thr Lys Glu Tyr
        35                  40                  45

<210> SEQ ID NO 90
<211> LENGTH: 125
<212> TYPE: PRT
<213> ORGANISM: Campylobacter jejuni ATCC 700819

<400> SEQUENCE: 90

Met Ala Ile Ser Lys Glu Asp Val Leu Glu Tyr Ile Ser Asn Leu Ser
1               5                   10                  15

Val Leu Glu Leu Ser Glu Leu Val Lys Glu Phe Glu Glu Lys Phe Gly
            20                  25                  30

Val Ser Ala Ala Pro Val Met Val Ala Gly Gly Ala Val Ala Gly Gly
        35                  40                  45

Ala Val Ala Ala Ala Glu Glu Lys Thr Glu Phe Asp Ile Val Leu Thr
    50                  55                  60

Asp Gly Gly Ala Lys Lys Ile Glu Val Ile Lys Ile Val Arg Ala Leu
65                  70                  75                  80

Thr Gly Leu Gly Leu Lys Glu Ala Lys Asp Ala Val Glu Gln Thr Pro
                85                  90                  95

Ser Thr Leu Lys Glu Gly Val Ala Lys Ala Glu Ala Glu Ala Lys
            100                 105                 110

Lys Gln Leu Glu Glu Ala Gly Ala Lys Val Glu Leu Lys
        115                 120                 125

<210> SEQ ID NO 91
<211> LENGTH: 93
<212> TYPE: PRT
<213> ORGANISM: Campylobacter jejuni ATCC 700819

<400> SEQUENCE: 91

Met Ala Asp Ile Thr Asp Ile Lys Thr Ile Leu Tyr Thr Glu Lys Ser
1               5                   10                  15

Leu Asn Leu Gln Glu Gln Gly Val Val Ile Gln Thr Ser Pro Lys
            20                  25                  30

Met Thr Lys Thr Gly Leu Lys Ala Val Leu Lys Glu Tyr Phe Gly Val
        35                  40                  45

Thr Pro Lys Ser Ile Asn Ser Leu Arg Met Asp Gly Lys Ile Lys Arg
    50                  55                  60

Phe Arg Gly Arg Leu Gly Gln Arg Asn Asn Tyr Lys Lys Phe Tyr Val
65                  70                  75                  80

Lys Leu Pro Glu Gly Val Ser Leu Glu Asn Thr Glu Ala
                85                  90

<210> SEQ ID NO 92
<211> LENGTH: 77
<212> TYPE: PRT
<213> ORGANISM: Campylobacter jejuni ATCC 700819

<400> SEQUENCE: 92

Met Ala Val Lys Leu Lys Ile Lys Lys Gly Asp Ser Val Lys Val Ile
1               5                   10                  15

Thr Gly Asp Asp Lys Gly Lys Thr Gly Lys Val Leu Ala Val Tyr Pro
            20                  25                  30

Lys Thr Leu Lys Val Val Val Glu Gly Cys Lys Ile Ala Lys Lys Ala
        35                  40                  45

Ile Lys Pro Ser Glu Lys Asn Pro Asn Gly Gly Phe Ile Asn Lys Glu
    50                  55                  60

Met Pro Met Asp Ile Ser Asn Val Ala Lys Val Gln Glu
65                  70                  75

<210> SEQ ID NO 93
<211> LENGTH: 61
<212> TYPE: PRT
<213> ORGANISM: Campylobacter jejuni ATCC 700819

<400> SEQUENCE: 93

Met Ala Lys Lys Ser Met Ile Ala Lys Ala Ala Arg Lys Pro Lys Phe
1               5                   10                  15

Lys Val Arg Ala Tyr Thr Arg Cys Gln Ile Cys Gly Arg Pro His Ser
            20                  25                  30

Val Tyr Arg Asp Phe Gly Ile Cys Arg Val Cys Leu Arg Lys Met Gly
        35                  40                  45

Asn Glu Gly Leu Ile Pro Gly Leu Lys Lys Ala Ser Trp
    50                  55                  60

<210> SEQ ID NO 94
<211> LENGTH: 118
<212> TYPE: PRT
<213> ORGANISM: Campylobacter jejuni ATCC 700819

<400> SEQUENCE: 94

Met Arg Ala Asn Val Leu Lys Arg Lys Leu Thr Leu Arg Ile Lys Arg

```
               1               5                  10                 15
Lys Lys Arg Ile Arg Ala Lys Ile Ser Gly Cys Glu Asn Phe Pro Arg
               20                 25                 30

Ile Ser Val Phe Lys Ser Asn Arg Thr Leu Tyr Ile Gln Ala Ile Asp
               35                 40                 45

Asp Val Lys Ala Val Thr Leu Ala Ala Val Asp Gly Arg Lys Leu Gly
               50                 55                 60

Val Lys Ala Asn Lys Glu Gly Ala Lys Ile Ala Ala Glu Phe Ala
 65                70                 75                 80

Lys Thr Leu Lys Val Lys Lys Ile Glu Gln Ala Val Phe Asp Arg Asn
               85                 90                 95

Gly Tyr Val Tyr His Gly Val Ile Ala Ala Leu Ala Glu Ser Leu Arg
              100                105                110

Glu Asn Gly Ile Arg Leu
              115
```

<210> SEQ ID NO 95
<211> LENGTH: 37
<212> TYPE: PRT
<213> ORGANISM: Campylobacter jejuni ATCC 700819

<400> SEQUENCE: 95

```
Met Lys Val Arg Pro Ser Val Lys Lys Met Cys Asp Lys Cys Lys Val
 1               5                  10                 15

Val Arg Arg Lys Gly Val Val Arg Ile Ile Cys Glu Asn Pro Lys His
               20                 25                 30

Lys Gln Arg Gln Gly
               35
```

<210> SEQ ID NO 96
<211> LENGTH: 130
<212> TYPE: PRT
<213> ORGANISM: Campylobacter jejuni ATCC_1 700819

<400> SEQUENCE: 96

```
Met Ala Lys Arg Lys Ile Val Lys Lys Val Val Lys Lys Asn Ile
 1               5                  10                 15

Ala Lys Gly Ile Val Tyr Ile Ser Ala Thr Phe Asn Asn Thr Met Val
               20                 25                 30

Thr Val Thr Asp Glu Met Gly Asn Ala Ile Ala Trp Ser Ser Ala Gly
               35                 40                 45

Gly Leu Gly Phe Lys Gly Ser Lys Ser Thr Pro Tyr Ala Ala Gln
 50                55                 60

Gln Ala Val Glu Asp Ala Leu Asn Lys Ala Lys Glu His Gly Ile Lys
 65                70                 75                 80

Glu Val Gly Ile Lys Val Gln Gly Pro Gly Ser Gly Arg Glu Thr Ala
               85                 90                 95

Val Lys Ser Val Gly Ala Met Glu Gly Ile Lys Val Thr Phe Leu Lys
              100                105                110

Asp Ile Thr Pro Leu Ala His Asn Gly Cys Arg Pro Pro Lys Arg Arg
              115                120                125

Arg Val
     130
```

<210> SEQ ID NO 97
<211> LENGTH: 48
<212> TYPE: PRT

<213> ORGANISM: Campylobacter jejuni doylei ATCC 49349T

<400> SEQUENCE: 97

Met Ala Val Pro Lys Arg Arg Val Ser Lys Thr Arg Ala Ala Lys Arg
1               5                   10                  15

Arg Thr His Tyr Lys Val Ser Leu Pro Met Pro Val Lys Asp Lys Asp
            20                  25                  30

Gly Ser Tyr Lys Met Pro His Arg Ala Asn Pro Thr Thr Lys Glu Tyr
        35                  40                  45

<210> SEQ ID NO 98
<211> LENGTH: 125
<212> TYPE: PRT
<213> ORGANISM: Campylobacter jejuni doylie ATCC 49349T

<400> SEQUENCE: 98

Met Ala Ile Ser Lys Glu Asp Val Leu Glu Tyr Ile Ser Asn Leu Ser
1               5                   10                  15

Val Leu Glu Leu Ser Glu Leu Val Lys Glu Phe Glu Glu Lys Phe Gly
            20                  25                  30

Val Ser Ala Ala Pro Val Met Val Ala Gly Gly Ala Ala Ala Gly Gly
        35                  40                  45

Ala Ala Ala Ala Glu Glu Lys Thr Glu Phe Asp Ile Val Leu Thr
    50                  55                  60

Asp Gly Gly Ala Lys Lys Ile Glu Val Ile Lys Ile Val Arg Ala Leu
65                  70                  75                  80

Thr Gly Leu Gly Leu Lys Glu Ala Lys Asp Ala Val Glu Gln Thr Pro
                85                  90                  95

Ser Thr Leu Lys Glu Gly Val Ala Lys Ala Glu Ala Glu Ala Lys
            100                 105                 110

Lys Gln Leu Glu Glu Ala Gly Ala Lys Val Glu Leu Lys
        115                 120                 125

<210> SEQ ID NO 99
<211> LENGTH: 93
<212> TYPE: PRT
<213> ORGANISM: Campylobacter jejuni doylei ATCC 49349T

<400> SEQUENCE: 99

Met Ala Asp Ile Thr Asp Ile Lys Thr Ile Leu Tyr Thr Glu Lys Ser
1               5                   10                  15

Leu Asn Leu Gln Glu Gln Gly Val Val Ile Gln Thr Ser Pro Lys
            20                  25                  30

Met Thr Lys Thr Gly Leu Lys Ala Val Leu Lys Glu Tyr Phe Gly Val
        35                  40                  45

Thr Pro Lys Ser Ile Asn Ser Leu Arg Met Asp Gly Lys Val Lys Arg
    50                  55                  60

Phe Arg Gly Arg Leu Gly Gln Arg Asn Asp Tyr Lys Lys Phe Tyr Val
65                  70                  75                  80

Lys Leu Pro Glu Gly Val Ser Leu Glu Asn Ala Glu Ala
                85                  90

<210> SEQ ID NO 100
<211> LENGTH: 77
<212> TYPE: PRT
<213> ORGANISM: Campylobacter jejuni doylei ATCC 49349T

<400> SEQUENCE: 100

```
Met Ala Val Lys Leu Lys Ile Lys Lys Gly Asp Asn Val Lys Val Ile
1               5                   10                  15

Thr Gly Asp Asp Lys Gly Lys Thr Gly Lys Val Leu Ala Val Tyr Pro
            20                  25                  30

Lys Thr Leu Lys Val Val Glu Gly Cys Lys Ile Ala Lys Lys Ala
        35                  40                  45

Ile Lys Pro Ser Glu Lys Asn Pro Asn Gly Gly Phe Ile Asn Lys Glu
    50                  55                  60

Met Pro Met Asp Ile Ser Asn Val Ala Lys Val Gln Glu
65                  70                  75
```

<210> SEQ ID NO 101
<211> LENGTH: 61
<212> TYPE: PRT
<213> ORGANISM: Campylobacter jejuni ATCC 49349T

<400> SEQUENCE: 101

```
Met Ala Lys Lys Ser Met Ile Ala Lys Ala Ala Arg Lys Pro Lys Phe
1               5                   10                  15

Lys Val Arg Ala Tyr Thr Arg Cys Gln Ile Cys Gly Arg Pro His Ser
            20                  25                  30

Val Tyr Arg Asp Phe Gly Ile Cys Arg Val Cys Leu Arg Lys Met Gly
        35                  40                  45

Asn Glu Gly Leu Ile Pro Gly Leu Lys Lys Ala Ser Trp
    50                  55                  60
```

<210> SEQ ID NO 102
<211> LENGTH: 118
<212> TYPE: PRT
<213> ORGANISM: Campylobacter jejuni doylei ATCC 49349T

<400> SEQUENCE: 102

```
Met Arg Ala Asn Val Leu Lys Arg Lys Leu Thr Leu Arg Ile Lys Arg
1               5                   10                  15

Lys Lys Arg Ile Arg Ala Lys Ile Ser Gly Cys Glu Asn Phe Pro Arg
            20                  25                  30

Ile Ser Val Phe Lys Ser Asn Arg Thr Leu Tyr Ile Gln Ala Ile Asp
        35                  40                  45

Asp Val Lys Ala Val Thr Leu Ala Ala Val Asp Gly Arg Lys Leu Gly
    50                  55                  60

Val Lys Ala Asn Lys Glu Gly Ala Lys Lys Ile Ala Ala Glu Phe Ala
65                  70                  75                  80

Lys Thr Leu Lys Ala Lys Lys Ile Glu Gln Ala Val Phe Asp Arg Asn
            85                  90                  95

Gly Tyr Val Tyr His Gly Val Ile Ala Ala Leu Ala Glu Ser Leu Arg
        100                 105                 110

Glu Asn Gly Ile Arg Leu
        115
```

<210> SEQ ID NO 103
<211> LENGTH: 37
<212> TYPE: PRT
<213> ORGANISM: Campylobacter jejuni ATCC 49349T

<400> SEQUENCE: 103

```
Met Lys Val Arg Pro Ser Val Lys Lys Met Cys Asp Lys Cys Lys Val
1               5                   10                  15

Val Arg Arg Lys Gly Val Val Arg Ile Ile Cys Glu Asn Pro Lys His
```

```
                    20                  25                  30

Lys Gln Arg Gln Gly
        35

<210> SEQ ID NO 104
<211> LENGTH: 130
<212> TYPE: PRT
<213> ORGANISM: Campylobacter jejuni doylei ATCC_1 49349T

<400> SEQUENCE: 104

Met Ala Lys Arg Lys Ile Val Lys Lys Val Val Lys Lys Asn Ile
1               5                   10                  15

Ala Lys Gly Ile Val Tyr Ile Ser Ala Thr Phe Asn Asn Thr Met Val
                20                  25                  30

Thr Val Thr Asp Glu Met Gly Asn Ala Ile Ala Trp Ser Ser Ala Gly
            35                  40                  45

Ser Leu Gly Phe Lys Gly Ser Lys Ser Thr Pro Tyr Ala Ala Gln
    50                  55                  60

Gln Ala Val Glu Asp Ala Leu Asn Lys Ala Lys Glu His Gly Ile Lys
65                  70                  75                  80

Glu Val Gly Ile Lys Val Gln Gly Pro Gly Ser Gly Arg Glu Thr Ala
                85                  90                  95

Val Lys Ser Val Gly Ala Met Glu Gly Ile Lys Val Thr Phe Leu Lys
            100                 105                 110

Asp Ile Thr Pro Leu Ala His Asn Gly Cys Arg Pro Pro Lys Arg Arg
        115                 120                 125

Arg Val
    130

<210> SEQ ID NO 105
<211> LENGTH: 48
<212> TYPE: PRT
<213> ORGANISM: Campylobacter jejuni doylei ATCC 49350

<400> SEQUENCE: 105

Met Ala Val Pro Lys Arg Arg Val Ser Lys Thr Arg Ala Ala Lys Arg
1               5                   10                  15

Arg Thr His Tyr Lys Val Ser Leu Pro Met Pro Ile Lys Asp Lys Asp
                20                  25                  30

Gly Ser Tyr Lys Met Pro His Arg Ala Asn Leu Thr Thr Lys Glu Tyr
            35                  40                  45

<210> SEQ ID NO 106
<211> LENGTH: 125
<212> TYPE: PRT
<213> ORGANISM: Campylobacter jejuni doylei ATCC 49350

<400> SEQUENCE: 106

Met Ala Ile Ser Lys Glu Asp Val Leu Glu Tyr Ile Ser Asn Leu Ser
1               5                   10                  15

Val Leu Glu Leu Ser Glu Leu Val Lys Glu Phe Glu Glu Lys Phe Gly
                20                  25                  30

Val Ser Ala Ala Pro Val Met Val Ala Gly Gly Ala Ala Ala Gly Gly
            35                  40                  45

Ala Ala Ala Ala Ala Glu Glu Lys Thr Glu Phe Asp Ile Val Leu Thr
    50                  55                  60

Asp Gly Gly Ala Lys Lys Ile Glu Val Ile Lys Ile Val Arg Ala Leu
65                  70                  75                  80
```

```
Thr Gly Leu Gly Leu Lys Glu Ala Lys Asp Ala Val Glu Gln Thr Pro
                85                  90                  95

Ser Thr Leu Lys Glu Gly Val Ala Ala Glu Ala Glu Ala Lys
            100                 105                 110

Lys Gln Leu Glu Glu Ala Gly Ala Lys Val Glu Leu Lys
        115                 120                 125

<210> SEQ ID NO 107
<211> LENGTH: 93
<212> TYPE: PRT
<213> ORGANISM: Campylobacter jejuni doylei ATCC 49350

<400> SEQUENCE: 107

Met Ala Asp Ile Thr Asp Ile Lys Thr Ile Leu Tyr Thr Glu Lys Ser
1               5                   10                  15

Leu Asn Leu Gln Glu Gln Gly Val Val Ile Gln Thr Ser Pro Lys
            20                  25                  30

Met Thr Lys Thr Gly Leu Lys Ala Val Leu Lys Glu Tyr Phe Gly Val
            35                  40                  45

Thr Pro Lys Ser Ile Asn Ser Leu Arg Met Asp Gly Lys Val Lys Arg
50                  55                  60

Phe Arg Gly Arg Leu Gly Gln Arg Asn Asp Tyr Lys Lys Phe Tyr Val
65                  70                  75                  80

Lys Leu Pro Glu Gly Val Ser Leu Glu Asn Ala Glu Ala
                85                  90

<210> SEQ ID NO 108
<211> LENGTH: 77
<212> TYPE: PRT
<213> ORGANISM: Campylobacter jejuni doylei ATCC 49350

<400> SEQUENCE: 108

Met Ala Val Lys Leu Lys Ile Lys Lys Gly Asp Asn Val Lys Val Ile
1               5                   10                  15

Thr Gly Asp Asp Lys Gly Lys Thr Gly Lys Val Leu Ala Val Tyr Pro
            20                  25                  30

Lys Thr Leu Lys Val Val Val Glu Gly Cys Lys Ile Ala Lys Lys Ala
        35                  40                  45

Ile Lys Pro Ser Glu Lys Asn Pro Asn Gly Gly Phe Ile Asn Lys Glu
50                  55                  60

Met Pro Met Asp Ile Ser Asn Val Ala Lys Val Gln Glu
65                  70                  75

<210> SEQ ID NO 109
<211> LENGTH: 61
<212> TYPE: PRT
<213> ORGANISM: Campylobacter jejuni doylei ATCC 49350

<400> SEQUENCE: 109

Met Ala Lys Lys Ser Met Ile Ala Lys Ala Arg Lys Pro Lys Phe
1               5                   10                  15

Lys Val Arg Ala Tyr Thr Arg Cys Gln Ile Cys Gly Arg Pro His Ser
            20                  25                  30

Val Tyr Arg Asp Phe Gly Ile Cys Arg Val Cys Leu Arg Lys Met Gly
        35                  40                  45

Asn Glu Gly Leu Ile Pro Gly Leu Lys Lys Ala Ser Trp
50                  55                  60
```

<210> SEQ ID NO 110
<211> LENGTH: 118
<212> TYPE: PRT
<213> ORGANISM: Campylobacter jejuni doylei ATCC 49350

<400> SEQUENCE: 110

Met Arg Ala Asn Val Leu Lys Arg Lys Leu Thr Leu Arg Ile Lys Arg
1               5                   10                  15

Lys Lys Arg Ile Arg Ala Lys Ile Ser Gly Cys Glu Asn Phe Pro Arg
                20                  25                  30

Ile Ser Val Phe Lys Ser Asn Arg Thr Leu Tyr Ile Gln Ala Ile Asp
            35                  40                  45

Asp Val Lys Ala Val Thr Leu Ala Ala Val Asp Gly Arg Lys Leu Gly
        50                  55                  60

Val Lys Ala Asn Lys Glu Gly Ala Lys Ile Ala Ala Glu Phe Ala
65                  70                  75                  80

Lys Thr Leu Lys Ala Lys Lys Ile Glu Gln Ala Val Phe Asp Arg Asn
                85                  90                  95

Gly Tyr Val Tyr His Gly Val Ile Ala Val Leu Ala Glu Ser Leu Arg
            100                 105                 110

Glu Asn Gly Ile Arg Leu
        115

<210> SEQ ID NO 111
<211> LENGTH: 37
<212> TYPE: PRT
<213> ORGANISM: Campylobacter jejuni doylei ATCC 49350

<400> SEQUENCE: 111

Met Lys Val Arg Pro Ser Val Lys Lys Met Cys Asp Lys Cys Lys Val
1               5                   10                  15

Val Arg Arg Lys Gly Val Val Arg Ile Ile Cys Glu Asn Pro Lys His
                20                  25                  30

Lys Gln Arg Gln Gly
        35

<210> SEQ ID NO 112
<211> LENGTH: 130
<212> TYPE: PRT
<213> ORGANISM: Campylobacter jejuni doylei ATCC_1 49350

<400> SEQUENCE: 112

Met Ala Lys Arg Lys Ile Val Lys Lys Val Val Lys Asn Ile
1               5                   10                  15

Ala Lys Gly Ile Val Tyr Ile Ser Ala Thr Phe Asn Asn Thr Met Val
                20                  25                  30

Thr Val Thr Asp Glu Met Gly Asn Ala Ile Ala Trp Ser Ser Ala Gly
            35                  40                  45

Ser Leu Gly Phe Lys Gly Ser Lys Ser Thr Pro Tyr Ala Ala Gln
        50                  55                  60

Gln Ala Val Glu Asp Ala Leu Asn Lys Ala Lys Glu His Gly Ile Lys
65                  70                  75                  80

Glu Val Gly Ile Lys Val Gln Gly Pro Gly Ser Gly Arg Glu Thr Ala
                85                  90                  95

Val Lys Ser Val Gly Ala Met Glu Gly Ile Lys Val Thr Phe Leu Lys
            100                 105                 110

Asp Ile Thr Pro Leu Ala His Asn Gly Cys Arg Pro Pro Lys Arg Arg

```
            115                 120                 125

Arg Val
    130

<210> SEQ ID NO 113
<211> LENGTH: 48
<212> TYPE: PRT
<213> ORGANISM: Campylobacter coli

<400> SEQUENCE: 113

Met Ala Val Pro Lys Arg Arg Val Ser Lys Thr Arg Ala Ala Lys Arg
1               5                   10                  15

Arg Thr His Tyr Lys Val Ser Leu Pro Met Pro Ile Lys Asp Lys Asp
            20                  25                  30

Gly Ser Tyr Lys Met Pro His Arg Ala Asn Pro Asn Thr Lys Glu Tyr
        35                  40                  45

<210> SEQ ID NO 114
<211> LENGTH: 125
<212> TYPE: PRT
<213> ORGANISM: Campylobacter coli

<400> SEQUENCE: 114

Met Ala Ile Ser Lys Glu Asp Val Leu Glu Phe Ile Ser Asn Leu Ser
1               5                   10                  15

Val Leu Glu Leu Ser Glu Leu Val Lys Glu Phe Glu Glu Lys Phe Gly
            20                  25                  30

Val Ser Ala Ala Pro Val Met Val Ala Gly Gly Ala Ala Ala Gly Gly
        35                  40                  45

Ala Ala Ala Ala Glu Glu Lys Thr Glu Phe Asp Ile Val Leu Val
    50                  55                  60

Asp Gly Gly Ala Lys Lys Ile Glu Val Ile Lys Ile Val Arg Ala Leu
65                  70                  75                  80

Thr Gly Leu Gly Leu Lys Glu Ala Lys Asp Ala Val Glu Gln Thr Pro
                85                  90                  95

Ser Thr Leu Lys Glu Gly Val Ser Lys Ala Asp Ala Glu Glu Ala Lys
            100                 105                 110

Lys Gln Leu Glu Glu Ala Gly Ala Lys Val Glu Leu Lys
        115                 120                 125

<210> SEQ ID NO 115
<211> LENGTH: 93
<212> TYPE: PRT
<213> ORGANISM: Campylobacter coli

<400> SEQUENCE: 115

Met Ala Asp Ile Thr Asp Ile Lys Thr Ile Leu Tyr Thr Glu Lys Ser
1               5                   10                  15

Leu Asn Leu Gln Glu Gln Gly Val Val Ile Gln Thr Ser Pro Lys
            20                  25                  30

Met Thr Lys Thr Gly Leu Lys Ala Val Leu Lys Glu Tyr Phe Gly Val
        35                  40                  45

Thr Pro Lys Ser Ile Asn Ser Leu Arg Met Asp Gly Val Lys Arg
    50                  55                  60

Phe Arg Gly Arg Leu Gly Gln Arg Asn Asp Tyr Lys Lys Phe Tyr Val
65                  70                  75                  80

Lys Leu Pro Glu Gly Val Ser Leu Glu Asn Ala Glu Ala
                85                  90
```

<210> SEQ ID NO 116
<211> LENGTH: 77
<212> TYPE: PRT
<213> ORGANISM: Campylobacter coli

<400> SEQUENCE: 116

Met Ala Val Lys Leu Lys Ile Lys Lys Gly Asp Ser Val Lys Val Ile
1               5                   10                  15

Thr Gly Asp Asp Lys Gly Lys Thr Gly Lys Val Leu Ala Val Tyr Pro
            20                  25                  30

Lys Thr Leu Lys Val Val Val Glu Gly Cys Lys Ile Ala Lys Lys Ala
        35                  40                  45

Ile Lys Pro Ser Glu Lys Asn Pro Asn Gly Gly Phe Ile Asn Lys Glu
    50                  55                  60

Met Pro Met Asp Ile Ser Asn Val Ala Lys Val Gln Glu
65                  70                  75

<210> SEQ ID NO 117
<211> LENGTH: 61
<212> TYPE: PRT
<213> ORGANISM: Campylobacter coli

<400> SEQUENCE: 117

Met Ala Lys Lys Ser Met Ile Ala Lys Ala Arg Lys Pro Lys Phe
1               5                   10                  15

Lys Val Arg Gly Tyr Thr Arg Cys Gln Ile Cys Gly Arg Pro His Ser
            20                  25                  30

Val Tyr Arg Asp Phe Gly Ile Cys Arg Val Cys Leu Arg Lys Met Gly
        35                  40                  45

Asn Glu Gly Leu Ile Pro Gly Leu Lys Lys Ala Ser Trp
    50                  55                  60

<210> SEQ ID NO 118
<211> LENGTH: 118
<212> TYPE: PRT
<213> ORGANISM: Campylobacter coli

<400> SEQUENCE: 118

Met Arg Ala Asn Val Leu Lys Arg Lys Leu Thr Leu Arg Ile Lys Arg
1               5                   10                  15

Lys Lys Arg Ile Arg Ala Lys Ile Ser Gly Cys Glu Asn Phe Pro Arg
            20                  25                  30

Ile Ser Val Phe Lys Ser Asn Arg Thr Leu Tyr Ile Gln Ala Ile Asp
        35                  40                  45

Asp Val Lys Ala Val Thr Leu Ala Ala Val Asp Gly Arg Lys Leu Gly
    50                  55                  60

Val Lys Ala Asn Lys Glu Gly Ala Lys Ile Ala Thr Glu Phe Ala
65                  70                  75                  80

Lys Val Leu Lys Ala Lys Gln Ile Glu Gln Ala Val Phe Asp Arg Asn
            85                  90                  95

Gly Tyr Val Tyr His Gly Val Ile Ala Ala Leu Ala Glu Ser Leu Arg
        100                 105                 110

Glu Asn Gly Ile Arg Leu
        115

<210> SEQ ID NO 119
<211> LENGTH: 37

```
<212> TYPE: PRT
<213> ORGANISM: Campylobacter coli

<400> SEQUENCE: 119

Met Lys Val Arg Pro Ser Val Lys Met Cys Asp Lys Cys Lys Val
1               5                   10                  15

Val Arg Arg Lys Gly Val Val Arg Ile Ile Cys Glu Asn Pro Lys His
            20                  25                  30

Lys Gln Arg Gln Gly
        35

<210> SEQ ID NO 120
<211> LENGTH: 130
<212> TYPE: PRT
<213> ORGANISM: Campylobacter coli

<400> SEQUENCE: 120

Met Ala Lys Arg Lys Ile Val Lys Lys Val Val Lys Lys Asn Ile
1               5                   10                  15

Ala Lys Gly Ile Val Tyr Ile Ser Ala Thr Phe Asn Asn Thr Met Val
            20                  25                  30

Thr Val Thr Asp Glu Met Gly Asn Ala Ile Ala Trp Ser Ser Ala Gly
        35                  40                  45

Gly Leu Gly Phe Lys Gly Ser Lys Lys Ser Thr Pro Tyr Ala Ala Gln
    50                  55                  60

Gln Ala Val Glu Asp Ala Leu Asn Lys Ala Lys Glu His Gly Ile Lys
65                  70                  75                  80

Glu Val Gly Ile Lys Val Gln Gly Pro Gly Ser Gly Arg Glu Thr Ala
                85                  90                  95

Val Lys Ser Val Gly Ala Met Glu Gly Ile Lys Val Thr Phe Leu Lys
            100                 105                 110

Asp Ile Thr Pro Leu Ala His Asn Gly Cys Arg Pro Lys Arg Arg
        115                 120                 125

Arg Val
    130

<210> SEQ ID NO 121
<211> LENGTH: 48
<212> TYPE: PRT
<213> ORGANISM: Campylobacter lari

<400> SEQUENCE: 121

Met Ala Val Pro Lys Arg Arg Val Ser Lys Thr Arg Ala Ala Lys Arg
1               5                   10                  15

Arg Thr His Tyr Lys Val Thr Leu Pro Met Pro Ile Lys Asp Lys Asp
            20                  25                  30

Gly Ser Tyr Lys Met Pro His Arg Val Asn Pro Val Thr Lys Glu Tyr
        35                  40                  45

<210> SEQ ID NO 122
<211> LENGTH: 125
<212> TYPE: PRT
<213> ORGANISM: Campylobacter lari

<400> SEQUENCE: 122

Met Ala Ile Thr Lys Glu Asp Val Leu Glu Phe Ile Ser Asn Leu Ser
1               5                   10                  15

Val Leu Glu Leu Ser Glu Leu Val Lys Glu Phe Glu Glu Lys Phe Gly
            20                  25                  30
```

Val Ser Ala Ala Pro Val Met Val Gly Ala Ala Val Gly Ala
        35                  40                  45

Ala Gly Gly Ala Ala Glu Glu Lys Thr Glu Phe Asp Ile Val Leu Gln
 50                  55                  60

Asp Gly Gly Asp Lys Lys Ile Asn Val Ile Lys Val Arg Ala Leu
 65                  70                  75                  80

Thr Gly Leu Gly Leu Lys Glu Ala Lys Asp Ala Val Glu Gln Thr Pro
                 85                  90                  95

Ser Val Leu Lys Glu Gly Val Ser Lys Ala Glu Ala Glu Glu Ala Lys
            100                 105                 110

Lys Gln Leu Glu Glu Ala Gly Ala Lys Val Glu Leu Lys
            115                 120                 125

<210> SEQ ID NO 123
<211> LENGTH: 93
<212> TYPE: PRT
<213> ORGANISM: Campylobacter lari

<400> SEQUENCE: 123

Met Ala Asp Ile Thr Asp Ile Lys Thr Ile Leu Tyr Thr Glu Lys Ser
1               5                   10                  15

Leu Asn Leu Gln Glu Gln Gly Val Val Ile Gln Thr Ser Pro Lys
             20                  25                  30

Met Thr Lys Asn Gly Leu Lys Glu Val Leu Arg Glu Tyr Phe Gly Val
             35                  40                  45

Thr Pro Val Arg Ile Asn Ser Leu Lys Met Asp Gly Lys Ile Lys Arg
 50                  55                  60

Phe Arg Gly Arg Glu Gly Gln Arg Asn Ser Phe Lys Lys Phe Tyr Val
 65                  70                  75                  80

Lys Leu Pro Glu Gly Val Ser Leu Glu Ser Ser Glu Ala
                 85                  90

<210> SEQ ID NO 124
<211> LENGTH: 75
<212> TYPE: PRT
<213> ORGANISM: Campylobacter lari

<400> SEQUENCE: 124

Met Lys Leu Lys Ile Lys Lys Asn Asp Met Val Lys Val Ile Ala Gly
1               5                   10                  15

Asp Asp Lys Gly Lys Thr Gly Lys Val Leu Ala Val Phe Pro Lys Thr
             20                  25                  30

Asn Lys Val Ile Val Glu Gly Cys Lys Ile Ala Lys Lys Ala Val Lys
             35                  40                  45

Pro Ser Asp Lys Asn Pro Asn Gly Gly Phe Val Asn Lys Glu Met Pro
 50                  55                  60

Met Asp Ile Ser Asn Val Ala Lys Ala Gly Glu
 65                  70                  75

<210> SEQ ID NO 125
<211> LENGTH: 61
<212> TYPE: PRT
<213> ORGANISM: Campylobacter lari

<400> SEQUENCE: 125

Met Ala Lys Lys Ser Met Ile Ala Lys Ala Ala Arg Lys Pro Lys Phe
1               5                   10                  15

Ser Val Arg Gly Tyr Thr Arg Cys Gln Ile Cys Gly Arg Pro His Ser
            20                  25                  30

Val Tyr Arg Asp Phe Gly Ile Cys Arg Val Cys Leu Arg Lys Met Ala
            35                  40                  45

Asn Glu Gly Leu Ile Pro Gly Leu Lys Lys Ala Ser Trp
50                  55                  60

<210> SEQ ID NO 126
<211> LENGTH: 118
<212> TYPE: PRT
<213> ORGANISM: Campylobacter lari

<400> SEQUENCE: 126

Met Arg Ala Asn Val Leu Lys Arg Lys Leu Ser Leu Arg Ile Lys Arg
1               5                   10                  15

Lys Lys Arg Ile Arg Ala Lys Ile Ser Gly Thr Gln Ala Leu Pro Arg
            20                  25                  30

Ile Ser Val Phe Lys Ser Asn Arg Thr Leu Tyr Ile Gln Ala Ile Asp
            35                  40                  45

Asp Val Lys Ala Val Thr Leu Ala Ala Val Asp Gly Arg Lys Ile Gly
            50                  55                  60

Val Lys Ala Asn Lys Glu Gly Ala Lys Lys Ile Ala Ala Glu Phe Ala
65                  70                  75                  80

Lys Ala Leu Lys Ala Lys Asn Ile Glu Glu Ala Val Phe Asp Arg Asn
                85                  90                  95

Gly Tyr Leu Tyr His Gly Val Ile Ala Val Leu Ala Glu Ala Leu Arg
            100                 105                 110

Glu Asn Gly Ile Lys Leu
            115

<210> SEQ ID NO 127
<211> LENGTH: 37
<212> TYPE: PRT
<213> ORGANISM: Campylobacter lari

<400> SEQUENCE: 127

Met Lys Val Arg Pro Ser Val Lys Met Cys Asp Lys Cys Lys Val
1               5                   10                  15

Val Arg Arg Lys Gly Val Val Arg Ile Ile Cys Glu Asn Pro Lys His
            20                  25                  30

Lys Gln Arg Gln Gly
            35

<210> SEQ ID NO 128
<211> LENGTH: 130
<212> TYPE: PRT
<213> ORGANISM: Campylobacter lari

<400> SEQUENCE: 128

Met Ala Lys Arg Lys Val Val Lys Lys Val Val Lys Asn Ile
1               5                   10                  15

Ala Lys Gly Ile Val Tyr Ile Ser Ala Thr Phe Asn Asn Thr Met Val
            20                  25                  30

Thr Val Thr Asp Glu Met Gly Asn Ala Ile Ala Trp Ser Ala Gly
            35                  40                  45

Gly Leu Gly Phe Lys Gly Ser Lys Lys Ser Thr Pro Tyr Ala Ala Gln
            50                  55                  60

Gln Ala Val Glu Asp Ala Leu Asn Lys Ala Lys Glu His Gly Ile Lys

```
                65                  70                  75                  80
Glu Val Gly Ile Lys Val Gln Gly Pro Gly Ser Gly Arg Glu Thr Ala
                    85                  90                  95

Val Lys Ser Val Gly Ala Met Glu Gly Ile Lys Val Thr Phe Leu Lys
                100                 105                 110

Asp Ile Thr Pro Leu Ala His Asn Gly Cys Arg Pro Pro Lys Arg Arg
            115                 120                 125

Arg Val
    130

<210> SEQ ID NO 129
<211> LENGTH: 30
<212> TYPE: DNA
<213> ORGANISM: Artificial Sequence
<220> FEATURE:
<223> OTHER INFORMATION: Cam-S10-F primer
<220> FEATURE:
<221> NAME/KEY: misc_feature
<222> LOCATION: (10)..(10)
<223> OTHER INFORMATION: y is t/u or c

<400> SEQUENCE: 129
ggaaagaaty aggcttaagc taaaagctta                                      30

<210> SEQ ID NO 130
<211> LENGTH: 27
<212> TYPE: DNA
<213> ORGANISM: Artificial Sequence
<220> FEATURE:
<223> OTHER INFORMATION: Cam-S10-R primer
<220> FEATURE:
<221> NAME/KEY: misc_feature
<222> LOCATION: (9)..(9)
<223> OTHER INFORMATION: w is a or t/u
<220> FEATURE:
<221> NAME/KEY: misc_feature
<222> LOCATION: (12)..(12)
<223> OTHER INFORMATION: w is a or t/u
<220> FEATURE:
<221> NAME/KEY: misc_feature
<222> LOCATION: (15)..(15)
<223> OTHER INFORMATION: w is a or t
<220> FEATURE:
<221> NAME/KEY: misc_feature
<222> LOCATION: (18)..(18)
<223> OTHER INFORMATION: r is g or a
<220> FEATURE:
<221> NAME/KEY: misc_feature
<222> LOCATION: (21)..(21)
<223> OTHER INFORMATION: y is t/u or c

<400> SEQUENCE: 130
tccggtgcwa gwgawacrat yttcata                                         27

<210> SEQ ID NO 131
<211> LENGTH: 30
<212> TYPE: DNA
<213> ORGANISM: Artificial Sequence
<220> FEATURE:
<223> OTHER INFORMATION: Cam-S10-1 primer
<220> FEATURE:
<221> NAME/KEY: misc_feature
<222> LOCATION: (7)..(7)
<223> OTHER INFORMATION: y is t/u or c
<220> FEATURE:
<221> NAME/KEY: misc_feature
<222> LOCATION: (10)..(10)
<223> OTHER INFORMATION: y is t/u or c
<220> FEATURE:
<221> NAME/KEY: misc_feature
```

```
<222> LOCATION: (22)..(22)
<223> OTHER INFORMATION: h is a or c or t/u
<220> FEATURE:
<221> NAME/KEY: misc_feature
<222> LOCATION: (25)..(25)
<223> OTHER INFORMATION: h is a or c or t/u

<400> SEQUENCE: 131
ggaatayaty gtagaaaaaa thgghatgag                                    30

<210> SEQ ID NO 132
<211> LENGTH: 21
<212> TYPE: DNA
<213> ORGANISM: Artificial Sequence
<220> FEATURE:
<223> OTHER INFORMATION: Cam-S10-2r primer
<220> FEATURE:
<221> NAME/KEY: misc_feature
<222> LOCATION: (8)..(8)
<223> OTHER INFORMATION: y is t/u or c
<220> FEATURE:
<221> NAME/KEY: misc_feature
<222> LOCATION: (13)..(13)
<223> OTHER INFORMATION: r is a or g

<400> SEQUENCE: 132
tacctggytg aacrcgacct g                                             21

<210> SEQ ID NO 133
<211> LENGTH: 25
<212> TYPE: DNA
<213> ORGANISM: Artificial Sequence
<220> FEATURE:
<223> OTHER INFORMATION: Cam-S10-3 primer
<220> FEATURE:
<221> NAME/KEY: misc_feature
<222> LOCATION: (14)..(14)
<223> OTHER INFORMATION: r is a or g
<220> FEATURE:
<221> NAME/KEY: misc_feature
<222> LOCATION: (17)..(17)
<223> OTHER INFORMATION: w is a or t/u

<400> SEQUENCE: 133
gtggtggtaa aaarccwgga gacaa                                         25

<210> SEQ ID NO 134
<211> LENGTH: 20
<212> TYPE: DNA
<213> ORGANISM: Artificial Sequence
<220> FEATURE:
<223> OTHER INFORMATION: Cam-S10-4 primer
<220> FEATURE:
<221> NAME/KEY: misc_feature
<222> LOCATION: (9)..(9)
<223> OTHER INFORMATION: d is a or g or t/u
<220> FEATURE:
<221> NAME/KEY: misc_feature
<222> LOCATION: (12)..(12)
<223> OTHER INFORMATION: w is a or t/u
<220> FEATURE:
<221> NAME/KEY: misc_feature
<222> LOCATION: (15)..(15)
<223> OTHER INFORMATION: h is a or c or t/u
<220> FEATURE:
<221> NAME/KEY: misc_feature
<222> LOCATION: (18)..(18)
<223> OTHER INFORMATION: r is g or a

<400> SEQUENCE: 134
ggaccaaadg cwachgcrcc                                               20
```

```
<210> SEQ ID NO 135
<211> LENGTH: 30
<212> TYPE: DNA
<213> ORGANISM: Artificial Sequence
<220> FEATURE:
<223> OTHER INFORMATION: Cam-S10-5 primer
<220> FEATURE:
<221> NAME/KEY: misc_feature
<222> LOCATION: (13)..(13)
<223> OTHER INFORMATION: y is t/u or c
<220> FEATURE:
<221> NAME/KEY: misc_feature
<222> LOCATION: (21)..(21)
<223> OTHER INFORMATION: w is a or t/u
<220> FEATURE:
<221> NAME/KEY: misc_feature
<222> LOCATION: (25)..(25)
<223> OTHER INFORMATION: b is g or c or t/u

<400> SEQUENCE: 135
atatactcca agyagaagat wtatbacagg                                30

<210> SEQ ID NO 136
<211> LENGTH: 29
<212> TYPE: DNA
<213> ORGANISM: Artificial Sequence
<220> FEATURE:
<223> OTHER INFORMATION: Cam-S10-6 primer
<220> FEATURE:
<221> NAME/KEY: misc_feature
<222> LOCATION: (3)..(3)
<223> OTHER INFORMATION: v is a or g or c
<220> FEATURE:
<221> NAME/KEY: misc_feature
<222> LOCATION: (10)..(10)
<223> OTHER INFORMATION: r is g or a
<220> FEATURE:
<221> NAME/KEY: misc_feature
<222> LOCATION: (12)..(12)
<223> OTHER INFORMATION: h is a or c or t/u
<220> FEATURE:
<221> NAME/KEY: misc_feature
<222> LOCATION: (15)..(15)
<223> OTHER INFORMATION: w is a or t/u
<220> FEATURE:
<221> NAME/KEY: misc_feature
<222> LOCATION: (24)..(24)
<223> OTHER INFORMATION: y is t/u or c
<220> FEATURE:
<221> NAME/KEY: misc_feature
<222> LOCATION: (27)..(27)
<223> OTHER INFORMATION: m is a or c

<400> SEQUENCE: 136
ccvgtttatr thacwgaaaa tcayatmgg                                 29

<210> SEQ ID NO 137
<211> LENGTH: 30
<212> TYPE: DNA
<213> ORGANISM: Artificial Sequence
<220> FEATURE:
<223> OTHER INFORMATION: Cam-S10-7r primer
<220> FEATURE:
<221> NAME/KEY: misc_feature
<222> LOCATION: (4)..(5)
<223> OTHER INFORMATION: v is a or g or c
<220> FEATURE:
<221> NAME/KEY: misc_feature
<222> LOCATION: (8)..(8)
<223> OTHER INFORMATION: y is t/u or c
<220> FEATURE:
<221> NAME/KEY: misc_feature
<222> LOCATION: (11)..(11)
<223> OTHER INFORMATION: w is a or t/u
```

<220> FEATURE:
<221> NAME/KEY: misc_feature
<222> LOCATION: (22)..(22)
<223> OTHER INFORMATION: r is g or a

<400> SEQUENCE: 137
tctwgcyttw gttggagata rtcttatgaa          30

<210> SEQ ID NO 138
<211> LENGTH: 28
<212> TYPE: DNA
<213> ORGANISM: Artificial Sequence
<220> FEATURE:
<223> OTHER INFORMATION: Cam-S10-8 primer
<220> FEATURE:
<221> NAME/KEY: misc_feature
<222> LOCATION: (8)..(8)
<223> OTHER INFORMATION: y is t/u or c
<220> FEATURE:
<221> NAME/KEY: misc_feature
<222> LOCATION: (14)..(14)
<223> OTHER INFORMATION: r is g or a
<220> FEATURE:
<221> NAME/KEY: misc_feature
<222> LOCATION: (17)..(17)
<223> OTHER INFORMATION: w is a or t/u

<400> SEQUENCE: 138
atagaaaytg ggartcwaga tggtttcc          28

<210> SEQ ID NO 139
<211> LENGTH: 31
<212> TYPE: DNA
<213> ORGANISM: Artificial Sequence
<220> FEATURE:
<223> OTHER INFORMATION: Cam-S10-9 primer
<220> FEATURE:
<221> NAME/KEY: misc_feature
<222> LOCATION: (8)..(8)
<223> OTHER INFORMATION: h is a or c or t/u
<220> FEATURE:
<221> NAME/KEY: misc_feature
<222> LOCATION: (11)..(11)
<223> OTHER INFORMATION: y is t/u or c
<220> FEATURE:
<221> NAME/KEY: misc_feature
<222> LOCATION: (17)..(17)
<223> OTHER INFORMATION: d is a or g or t/u
<220> FEATURE:
<221> NAME/KEY: misc_feature
<222> LOCATION: (18)..(18)
<223> OTHER INFORMATION: r is g or a
<220> FEATURE:
<221> NAME/KEY: misc_feature
<222> LOCATION: (20)..(20)
<223> OTHER INFORMATION: w is a or t/u
<220> FEATURE:
<221> NAME/KEY: misc_feature
<222> LOCATION: (26)..(26)
<223> OTHER INFORMATION: d is a or g or t/u

<400> SEQUENCE: 139
cttatgghaa yataggdrtw aaagtdtgga t          31

<210> SEQ ID NO 140
<211> LENGTH: 31
<212> TYPE: DNA
<213> ORGANISM: Artificial Sequence
<220> FEATURE:
<223> OTHER INFORMATION: Cam-S10-10 primer
<220> FEATURE:
<221> NAME/KEY: misc_feature
<222> LOCATION: (14)..(14)

```
<223> OTHER INFORMATION: w is a or t/u
<220> FEATURE:
<221> NAME/KEY: misc_feature
<222> LOCATION: (20)..(20)
<223> OTHER INFORMATION: r is g or a
<220> FEATURE:
<221> NAME/KEY: misc_feature
<222> LOCATION: (23)..(23)
<223> OTHER INFORMATION: w is a or t/u
<220> FEATURE:
<221> NAME/KEY: misc_feature
<222> LOCATION: (29)..(29)
<223> OTHER INFORMATION: y is t/u or c

<400> SEQUENCE: 140
aaaagctaaa aacwatgcar ctwactaayc c                              31

<210> SEQ ID NO 141
<211> LENGTH: 30
<212> TYPE: DNA
<213> ORGANISM: Artificial Sequence
<220> FEATURE:
<223> OTHER INFORMATION: Cam-spc-F primer
<220> FEATURE:
<221> NAME/KEY: misc_feature
<222> LOCATION: (9)..(9)
<223> OTHER INFORMATION: y is t/u or c
<220> FEATURE:
<221> NAME/KEY: misc_feature
<222> LOCATION: (12)..(12)
<223> OTHER INFORMATION: r is g or a
<220> FEATURE:
<221> NAME/KEY: misc_feature
<222> LOCATION: (21)..(21)
<223> OTHER INFORMATION: b is g or c or t/u
<220> FEATURE:
<221> NAME/KEY: misc_feature
<222> LOCATION: (27)..(27)
<223> OTHER INFORMATION: y is t/u or c

<400> SEQUENCE: 141
atgtgtatya argttttagg bggtagyaaa                                30

<210> SEQ ID NO 142
<211> LENGTH: 30
<212> TYPE: DNA
<213> ORGANISM: Artificial Sequence
<220> FEATURE:
<223> OTHER INFORMATION: Cam-spc-R primer
<220> FEATURE:
<221> NAME/KEY: misc_feature
<222> LOCATION: (10)..(10)
<223> OTHER INFORMATION: y is t/u or c
<220> FEATURE:
<221> NAME/KEY: misc_feature
<222> LOCATION: (13)..(13)
<223> OTHER INFORMATION: d is a or g or t/u
<220> FEATURE:
<221> NAME/KEY: misc_feature
<222> LOCATION: (16)..(16)
<223> OTHER INFORMATION: y is t/u or c
<220> FEATURE:
<221> NAME/KEY: misc_feature
<222> LOCATION: (25)..(25)
<223> OTHER INFORMATION: y is t/u or c
<220> FEATURE:
<221> NAME/KEY: misc_feature
<222> LOCATION: (28)..(28)
<223> OTHER INFORMATION: r is g or a

<400> SEQUENCE: 142
aatttgagcy tcdatytttc tcatygtrtc                                30
```

```
<210> SEQ ID NO 143
<211> LENGTH: 32
<212> TYPE: DNA
<213> ORGANISM: Artificial Sequence
<220> FEATURE:
<223> OTHER INFORMATION: Cam-spc-1 primer
<220> FEATURE:
<221> NAME/KEY: misc_feature
<222> LOCATION: (3)..(3)
<223> OTHER INFORMATION: r is g or a
<220> FEATURE:
<221> NAME/KEY: misc_feature
<222> LOCATION: (12)..(12)
<223> OTHER INFORMATION: h is a or c or t/u
<220> FEATURE:
<221> NAME/KEY: misc_feature
<222> LOCATION: (18)..(18)
<223> OTHER INFORMATION: y is t/u or c
<220> FEATURE:
<221> NAME/KEY: misc_feature
<222> LOCATION: (30)..(30)
<223> OTHER INFORMATION: m is a or c

<400> SEQUENCE: 143
gartttgata thaaaaaycc tatgcttatm cc                                   32

<210> SEQ ID NO 144
<211> LENGTH: 25
<212> TYPE: DNA
<213> ORGANISM: Artificial Sequence
<220> FEATURE:
<223> OTHER INFORMATION: Cam-spc-2 primer
<220> FEATURE:
<221> NAME/KEY: misc_feature
<222> LOCATION: (8)..(8)
<223> OTHER INFORMATION: w is a or t/u
<220> FEATURE:
<221> NAME/KEY: misc_feature
<222> LOCATION: (17)..(17)
<223> OTHER INFORMATION: d is a or g or t/u
<220> FEATURE:
<221> NAME/KEY: misc_feature
<222> LOCATION: (20)..(20)
<223> OTHER INFORMATION: m is a or c

<400> SEQUENCE: 144
caatgatwgc aaaagcdgcm cgcaa                                           25

<210> SEQ ID NO 145
<211> LENGTH: 27
<212> TYPE: DNA
<213> ORGANISM: Artificial Sequence
<220> FEATURE:
<223> OTHER INFORMATION: Cam-spc-3 primer
<220> FEATURE:
<221> NAME/KEY: misc_feature
<222> LOCATION: (3)..(4)
<223> OTHER INFORMATION: v is a or g or c
<220> FEATURE:
<221> NAME/KEY: misc_feature
<222> LOCATION: (19)..(19)
<223> OTHER INFORMATION: y is t/u or c

<400> SEQUENCE: 145
gcwtattggg gaacttayag agcttta                                         27

<210> SEQ ID NO 146
<211> LENGTH: 26
<212> TYPE: DNA
<213> ORGANISM: Artificial Sequence
<220> FEATURE:
<223> OTHER INFORMATION: Cam-spc-4r primer
<220> FEATURE:
```

```
<221> NAME/KEY: misc_feature
<222> LOCATION: (9)..(9)
<223> OTHER INFORMATION: y is t/u or c
<220> FEATURE:
<221> NAME/KEY: misc_feature
<222> LOCATION: (12)..(12)
<223> OTHER INFORMATION: r is g or a
<220> FEATURE:
<221> NAME/KEY: misc_feature
<222> LOCATION: (15)..(15)
<223> OTHER INFORMATION: r is g or a
<220> FEATURE:
<221> NAME/KEY: misc_feature
<222> LOCATION: (24)..(24)
<223> OTHER INFORMATION: k is g or t/u

<400> SEQUENCE: 146
ttagatgtyt trccrgcttt gcgkat                                          26

<210> SEQ ID NO 147
<211> LENGTH: 28
<212> TYPE: DNA
<213> ORGANISM: Artificial Sequence
<220> FEATURE:
<223> OTHER INFORMATION: Cam-spc-5 primer
<220> FEATURE:
<221> NAME/KEY: misc_feature
<222> LOCATION: (23)..(23)
<223> OTHER INFORMATION: y is t/u or c

<400> SEQUENCE: 147
aatttgaaga agtaatcgtc gayatcgg                                        28

<210> SEQ ID NO 148
<211> LENGTH: 25
<212> TYPE: DNA
<213> ORGANISM: Artificial Sequence
<220> FEATURE:
<223> OTHER INFORMATION: Cam-spc-6r primer
<220> FEATURE:
<221> NAME/KEY: misc_feature
<222> LOCATION: (4)..(4)
<223> OTHER INFORMATION: r is g or a
<220> FEATURE:
<221> NAME/KEY: misc_feature
<222> LOCATION: (7)..(7)
<223> OTHER INFORMATION: s is g or c
<220> FEATURE:
<221> NAME/KEY: misc_feature
<222> LOCATION: (10)..(10)
<223> OTHER INFORMATION: m is a or c
<220> FEATURE:
<221> NAME/KEY: misc_feature
<222> LOCATION: (13)..(13)
<223> OTHER INFORMATION: w is a or t/u
<220> FEATURE:
<221> NAME/KEY: misc_feature
<222> LOCATION: (19)..(19)
<223> OTHER INFORMATION: m is a or c

<400> SEQUENCE: 148
attracsccm ggwactggma cataa                                           25

<210> SEQ ID NO 149
<211> LENGTH: 29
<212> TYPE: DNA
<213> ORGANISM: Artificial Sequence
<220> FEATURE:
<223> OTHER INFORMATION: Cam-alpha-F primer
<220> FEATURE:
<221> NAME/KEY: misc_feature
<222> LOCATION: (6)..(6)
<223> OTHER INFORMATION: h is a or c or t/u
```

```
<220> FEATURE:
<221> NAME/KEY: misc_feature
<222> LOCATION: (12)..(12)
<223> OTHER INFORMATION: h is a or c or t/u
<220> FEATURE:
<221> NAME/KEY: misc_feature
<222> LOCATION: (15)..(15)
<223> OTHER INFORMATION: r is g or a
<220> FEATURE:
<221> NAME/KEY: misc_feature
<222> LOCATION: (18)..(18)
<223> OTHER INFORMATION: h is a or c or t/u
<220> FEATURE:
<221> NAME/KEY: misc_feature
<222> LOCATION: (24)..(24)
<223> OTHER INFORMATION: y is t/u or c

<400> SEQUENCE: 149
aaagthgaac thacrcchta tagycttga                                              29

<210> SEQ ID NO 150
<211> LENGTH: 25
<212> TYPE: DNA
<213> ORGANISM: Artificial Sequence
<220> FEATURE:
<223> OTHER INFORMATION: Cam-alpha-R primer
<220> FEATURE:
<221> NAME/KEY: misc_feature
<222> LOCATION: (5)..(5)
<223> OTHER INFORMATION: r is g or a
<220> FEATURE:
<221> NAME/KEY: misc_feature
<222> LOCATION: (11)..(11)
<223> OTHER INFORMATION: r is g or a
<220> FEATURE:
<221> NAME/KEY: misc_feature
<222> LOCATION: (17)..(17)
<223> OTHER INFORMATION: r is g or a

<400> SEQUENCE: 150
agccrcgcat rctatcraat tcatg                                                  25

<210> SEQ ID NO 151
<211> LENGTH: 25
<212> TYPE: DNA
<213> ORGANISM: Artificial Sequence
<220> FEATURE:
<223> OTHER INFORMATION: Cam-alpha-1 primer
<220> FEATURE:
<221> NAME/KEY: misc_feature
<222> LOCATION: (5)..(5)
<223> OTHER INFORMATION: y is t/u or c
<220> FEATURE:
<221> NAME/KEY: misc_feature
<222> LOCATION: (14)..(14)
<223> OTHER INFORMATION: r is g or a
<220> FEATURE:
<221> NAME/KEY: misc_feature
<222> LOCATION: (17)..(17)
<223> OTHER INFORMATION: h is a or c or t/u
<220> FEATURE:
<221> NAME/KEY: misc_feature
<222> LOCATION: (20)..(20)
<223> OTHER INFORMATION: d is a or g or t/u

<400> SEQUENCE: 151
taagygaaga tgargchgcd gctat                                                  25

<210> SEQ ID NO 152
<211> LENGTH: 28
<212> TYPE: DNA
<213> ORGANISM: Artificial Sequence
<220> FEATURE:
```

```
<223> OTHER INFORMATION: Camp-alpha-2r primer
<220> FEATURE:
<221> NAME/KEY: misc_feature
<222> LOCATION: (9)..(9)
<223> OTHER INFORMATION: r is g or a
<220> FEATURE:
<221> NAME/KEY: misc_feature
<222> LOCATION: (25)..(25)
<223> OTHER INFORMATION: w is a or t/u

<400> SEQUENCE: 152 cctttctrt gtcttaagcc tctawagc                                              28

<210> SEQ ID NO 153
<211> LENGTH: 28
<212> TYPE: DNA
<213> ORGANISM: Artificial Sequence
<220> FEATURE:
<223> OTHER INFORMATION: Camp-alpha-3 primer
<220> FEATURE:
<221> NAME/KEY: misc_feature
<222> LOCATION: (11)..(11)
<223> OTHER INFORMATION: w is a or t/u
<220> FEATURE:
<221> NAME/KEY: misc_feature
<222> LOCATION: (14)..(14)
<223> OTHER INFORMATION: r is g or a

<400> SEQUENCE: 153
gaggaccagt wgaraaatta gaaagacg                                             28
```